US012747287B2

(12) United States Patent
Wipperman et al.

(10) Patent No.: US 12,747,287 B2
(45) Date of Patent: Sep. 29, 2026

(54) METHODS OF IDENTIFYING AND EVALUATING CAT ALLERGY GENE SIGNATURES IN A SUBJECT BY DETERMINING A STRATIFIED SCORE BASED ON GENE EXPRESSION

(71) Applicant: Regeneron Pharmaceuticals, Inc., Tarrytown, NY (US)

(72) Inventors: Matthew F. Wipperman, Tarrytown, NY (US); Kaitlyn Gayvert, Tarrytown, NY (US); Wei Keat Lim, Tarrytown, NY (US); Jennifer D. Hamilton, Tarrytown, NY (US); Sara C. Hamon, Tarrytown, NY (US); Meagan O'Brien, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 601 days.

(21) Appl. No.: 18/339,557

(22) Filed: Jun. 22, 2023

(65) Prior Publication Data

US 2023/0416349 A1 Dec. 28, 2023

Related U.S. Application Data

(60) Provisional application No. 63/354,769, filed on Jun. 23, 2022, provisional application No. 63/355,051, filed on Jun. 23, 2022.

(51) Int. Cl.

| | |
|---|---|
| ***C07K 16/18*** | (2006.01) |
| ***A61K 39/00*** | (2006.01) |
| ***A61P 11/00*** | (2006.01) |
| ***A61P 11/06*** | (2006.01) |
| ***C12N 15/10*** | (2006.01) |
| ***C12Q 1/6809*** | (2018.01) |
| ***C12Q 1/6869*** | (2018.01) |
| ***C12Q 1/6883*** | (2018.01) |

(52) U.S. Cl.

CPC .............. *C07K 16/18* (2013.01); *A61P 11/00* (2018.01); *A61P 11/06* (2018.01); *C12N 15/10* (2013.01); *C12Q 1/6809* (2013.01); *C12Q 1/6869* (2013.01); *C12Q 1/6883* (2013.01); *A61K 2039/505* (2013.01); *A61K 2039/507* (2013.01); *C12Q 2600/106* (2013.01); *C12Q 2600/158* (2013.01)

(58) Field of Classification Search

None

See application file for complete search history.

(56) References Cited

U.S. PATENT DOCUMENTS

| | | | |
|---|---|---|---|
| 9,079,948 | B2 | 7/2015 | Orengo et al. |
| 10,047,153 | B2 | 8/2018 | Orengo et al. |
| 11,352,417 | B2 | 6/2022 | Orengo et al. |

FOREIGN PATENT DOCUMENTS

| | | |
|---|---|---|
| WO | 2008091814 | 7/2008 |
| WO | 2011051402 | 5/2011 |
| WO | 2018118713 | 6/2018 |

OTHER PUBLICATIONS

Kleine-Tebbe et al., "Role of the major allergen (Fel d I) in patients sensitized to cat allergens", Int Arch Allergy Immunol, 1993, 100, pp. 256-262.

Gronlund et al., "The Major Cat Allergen, Fel d 1, in Diagnosis and Therapy", Int Arch Allergy Immunol, 2010, 151, pp. 265-274.

Charpin et al., "Fel d I allergen distribution in cat fur and skin", J Allergy Clin Immunol, 1991, 88, pp. 77-82.

Van Ree et al., "Purified natural and recombinant Fel d 1 and cat albumin in in vitro diagnostics for cat allergy", J Allergy Clin Immunol, 1999, 104, pp. 1223-1230.

Custovic et al., "Distribution, aerodynamic characteristics, and removal of the major cat allergen Fel d 1 in British homes", Thorax, 1998, 53, pp. 33-38.

Bollinger et al., "Cat antigen in homes with and without cats may induce allergic symptoms", J Allergy Clin Immunol, 1996, 97, pp. 907-914.

Bollinger et al., "Measurement of cat allergen levels in the home by use of an amplified ELISA", J Allergy Clin Immunol, 1998, 101, pp. 124-125.

Arbes et al., "Asthma Cases Attributable to Atopy: Results from the Third National Health and Nutrition Examination Survey", J Allergy Clin Immunol, 2007, 120, pp. 1139-1145.

Giavina-Bianchi et al., "United airway disease: current perspectives", J Asthma Allergy, 2016, 9, pp. 93-100.

Sataraj et al., "Keep the cat, change the care pathway: A transformational approach to managing Fel d 1, the major cat allergen", Allergy, 2019, 74, pp. 5-17.

Durham et al., "SQ-standardized sublingual grass immunotherapy: confirmation of disease modification 2 years after 3 years of treatment in a randomized trial", J Allergy Clin Immunol, 2012, 129, pp. 717-725.

Durham et al., "Long-term clinical efficacy of grass-pollen immunotherapy", N Engl J Med, 1999, 341, pp. 468-475.

De Blay De Gaix et al., "A Single-Dose of REGN1908-1909 Reduced Bronchoconstriction in Cat-Allergic Subjects with Mild Asthma for up to 3 months following a controlled cat allergen challenge: a Phase 2, Randomized, Double-Blind, Placebo-Controlled Study", J Allergy Clin Immunol, 2021, 147(2), pp. 1.

(Continued)

*Primary Examiner* — Nora M Rooney

(74) *Attorney, Agent, or Firm* — Armstrong Teasdale LLP

(57) ABSTRACT

The present disclosure provides methods of identifying a subject as suitable for the treatment or prevention of asthma exacerbation induced by a cat allergen with at least one antibody to the cat allergen. The present disclosure also provides methods of treating a subject having asthma exacerbation induced by a cat allergen or preventing a subject from developing asthma exacerbation induced by a cat allergen by administering at least one antibody to the cat allergen to the subject.

10 Claims, 11 Drawing Sheets

(11 of 11 Drawing Sheet(s) Filed in Color)

(56) References Cited

OTHER PUBLICATIONS

Shamji et al., "Passive Prophylactic Administration with a Single Dose of Anti-Fel d 1 Monoclonal Antibodies REGN1908-1909 in Cat Allergen-induced Allergic Rhinitis: A Randomized, Double-Blind, Placebo-controlled Clinical Trial", American J Resp and Crit Care Med, 2021, 204(1), pp. 23-33.
Larson et al., "Nasal allergen challenge and environmental exposure chamber challenge: A randomized trial comparing clinical and biological responses to cat allergen", J Allergy Clin Immunol, 2020, 145(6), pp. 1585-1597.
Yang et al., "Cat allergen exposure in a naturalistic exposure chamber: A prospective observational study in cat-allergic subjects", Clin Exp Allergy, 2022, 52(2), pp. 265-275.

AR, asthmatic response; D, day; EAR, early asthmatic response; EEU, environmental exposure unit; FEV1, forced expiratory volume in 1 second; LAR, late asthmatic response; R, randomisation; SC, subcutaneous; W, week.

C)

A)

B)

A)

B)

C)

A)

B)

C)

METHODS OF IDENTIFYING AND EVALUATING CAT ALLERGY GENE SIGNATURES IN A SUBJECT BY DETERMINING A STRATIFIED SCORE BASED ON GENE EXPRESSION

FIELD

The present disclosure provides methods of identifying a subject as suitable for the treatment or prevention of asthma exacerbation induced by a cat allergen with at least one antibody to the cat allergen, and methods of treating a subject having asthma exacerbation induced by a cat allergen or preventing a subject from developing asthma exacerbation induced by a cat allergen by administering at least one antibody to the cat allergen to the subject.

BACKGROUND

Cat allergens are a common cause of Type 1 (IgE-mediated) allergic disease worldwide. *Felis domesticus* allergen 1 (Fel d 1) is produced by the sebaceous, anal, salivary, and lacrimal glands of the cat (Kleine-Tebbe et al., Int. Arch. Allergy Immunol., 1993, 100, 256-262; Grönlund et al., Int, Arch, Allergy Immunol, 2010, 151, 265-274; and Charpin et al., J. Allergy Clin. Immunol., 1991, 88, 77-82). Up to 95% of cat-allergic individuals have been found to have specific IgE to Fel d 1 (van Ree et al., J. Allergy Clin. Immunol., 1999, 104, 1223-1230) and accounts for 60-90% of the total allergenic activity in cat dander (Kleine-Tebbe et al., Int. Arch. Allergy Immunol., 1993, 100, 256-62). Forty (40) ng/$m^3$ Fel d 1 is the equivalent concentration that patients experience upon live cat exposure in homes where cats live (Custovic et al., Thorax., 1998, 53, 33-38; Bollinger et al., J. Allergy Clin. Immunol., 1996, 97, 907-914; and Bollinger et al., J. Allergy Clin. Immunol., 1998, 101, 124-125). Allergies to cats are a major risk factor in the development of asthma. Many cat-sensitized patients have a diagnosis of comorbid asthma, and approximately 30% of allergic asthmatics report a concomitant allergy to cats (Arbes et al., J. Allergy Clin. Immunol., 2007, 120, 1139-1145; Giavina-Bianchi et al., J. Asthma Allergy, 2016, 9, 93-100; and Sataraj et al., Allergy, 2019, 74, 5-17).

Allergen-specific immunotherapy (SIT) is a treatment option for patients with allergies (such as pollen, animal dander, or dust) when pharmacological therapies, such as antihistamines, are insufficient. SIT is an active immunization process whereby patients are administered increasing doses of the offending allergen, followed by a maintenance dose for up to several years. The goal of SIT is to induce immunological changes that result in symptom amelioration and sustained tolerance and desensitization. Although SIT can provide long-lasting protection from allergic disease, it carries a risk of adverse reactions due to administration of native allergen, has variable efficacy between patients, and can take 3 to 5 years to induce tolerance (Durham et al., J. Allergy Clin. Immunol., 2012, 129, 717-725; and Durham et al., N. Engl. J. Med., 1999, 341, 468-475).

There are three primary existing strategies for the treatment of cat allergy and associated asthma. A first strategy is allergen avoidance and preventive pharmacotherapies, such as antihistamines and intranasal corticosteroids. Often patients experience the persistence of moderate-to-severe symptoms. A second strategy is SIT, including both subcutaneous immunotherapy (SCIT) and sublingual immunotherapy (SLIT), as a possible treatment strategy. SCIT is associated with a risk of systemic allergic reactions, warranting administration in specialized settings with access to resuscitative methods. In the USA, SLIT requires co-prescription of an epinephrine autoinjector due to the uncommon risk of anaphylaxis and concern for severe allergic reactions affecting the mouth and throat. A third strategy is treatment with omalizumab, a monoclonal antibody against IgE39, which has demonstrated efficacy in reducing allergic symptoms, including for cat-allergic patients. Total IgE cutoff specified in the prescribing information makes some patients ineligible. Thus, new modalities are needed: i) a more convenient therapeutic approach with less frequent dosing than SCIT and SLIT, and without the associated risk of allergic reactions; and ii) a new treatment strategy for patients who are unable to receive omalizumab. Therefore, new modalities are needed to complement existing allergy treatment strategies.

SUMMARY

The present disclosure provides methods of identifying a subject as suitable for the treatment or prevention of asthma exacerbation induced by a cat allergen with at least one antibody to the cat allergen, the methods comprising: a) generating or having generated a first transcriptome for the subject; b) exposing the subject to at least one cat allergen; c) generating or having generated a second transcriptome for the subject after exposure to the at least one cat allergen; and d) screening the second transcriptome against the first transcriptome to generate a cat allergen exposure transcriptome; wherein the subject is suitable for the treatment or prevention of asthma exacerbation induced by a cat allergen with at least one antibody to the cat allergen when the cat allergen exposure transcriptome comprises: a downregulation of at least ten of the following genes: CCDC33, ADH6, IFLTD1, DLGAP1-AS5, DNAJB13, C2orf62, CCDC81, PIH1D3, NHLRC4, TMEM190, AK090700, KIF6, BBOX1, PTGFR, SEC14L3, BC022056, CASC2, PPP1R36, CNTN5, KLHDC8A, FHOD3, CAPS, UBD, TP73, BC023516, IFI44L, FAM86B1, CX3CL1, ACY3, MPDZ, IGFBP5, AK097288, IF16, ABCC6, GAS1, and PLCH1; and an upregulation of at least twenty of the following genes: ESPL1, NMU, CTSL2, CLIC3, CRABP2, AX746775, TMPRSS11A, NCCRP1, MSX2, HSP90AB4P, AIM1L, SERPINB2, IL1RN, KLK10, PXDN, HSPB8, CLCA4, KRT10, ZBED2, DSC2, LY6G6C, ADAMTSL4, OTOP3, FGFBP1, GPR115, TRPV3, CRISP3, SPRR3, PRSS3, A2ML1, SPINK7, LYPD3, RHCG, SPRR1A, MAP2, S100A8, RPTN, PRSS27, KRT6B, PPP2R2C, IL1RL1, CAMK2N1, CPA4, KLK13, SERPINB13, ALOX12, SLC39A2, KRT4, HOPX, FAM25A, EMP1, CNFN, KLK12, APOBEC3A, CAPN14, IVL, KLK8, SPRR1B, IGFBP6, IL36G, KLK7, EGR3, KRT78, CRNN, MAL, LINC00707, KRT24, KRT6A, TMPRSS11B, KRT14, PRB3, KRT13, LOC731424, and BCL2L2-PABPN1.

The present disclosure also provides methods of identifying a subject as suitable for the treatment or prevention of asthma exacerbation induced by a cat allergen with at least one antibody to the cat allergen, the method comprising: a) generating or having generated a first transcriptome for the subject before exposure to at least one cat allergen; b) exposing the subject to the at least one cat allergen; c) treating the subject with at least one antibody to the cat allergen; d) generating or having generated a second transcriptome for the subject after treatment with at least one antibody to the cat allergen; and e) screening the second transcriptome against the first transcriptome to generate a cat allergen exposure/treatment transcriptome; wherein the subject is suitable for the treatment or prevention of asthma exacerbation induced by a cat allergen with at least one antibody to the cat allergen when the cat allergen exposure/treatment transcriptome comprises: a downregulation of at least any five of the following genes: BC007880, BC080587, BX537909, NGS-17, LOC100862671, AX747215, P2RX1, SDS, S1PR4, RPPH1, ARPC4-TTLL3, and SERPING1; and an upregulation of at least any twenty-five of the following genes: C6orf165, ARHGEF33, LOC157381, ARHGEF26-AS1, IQUB, WDR78, CNTD1, TEX21P, REEP1, RBM24, TMEM212, TEX9, DIO1, ECT2L, GCNT4, FSD1L, MAMDC2, LOC100499484-C90RF174, ADH6, LOC653501, DNAH7, DCDC2, KLHL32, PTGES3L, ADAM22, AKAP6, TEX26, DPY19L2, ZBBX, TXLNB, ANKFN1, CHDC2, CRISPLD1, WDR96, FAM216B, AK057689, TSPAN19, DTHD1, PROS1, DNAH5, AX747851, MYLK, AK090700, SRD5A2, ANGPTL5, TMEM232, CXorf22, AK097702, AK310634, C1orf141, BICC1, FAM86B2, AX747150, PCDHB1, CAPS2, PTPN20B, TCP11X2, GIPC2, GRM5, LOC100130451, C12orf63, FL00322, MTTP, MROH9, SLC16A12, AK307870, MYCT1, AK094325, AX747187, FGF14, PHOSPHO2-KLHL23, CD200R1L, AK126334, PALM2-KAP2, and LY75-CD302.

The present disclosure also provides methods of identifying a subject as suitable for the treatment or prevention of asthma exacerbation induced by a cat allergen with at least one antibody to the cat allergen, the method comprising: a) exposing the subject to at least one cat allergen; b) generating or having generated a third transcriptome for the subject after exposure to at least one cat allergen; c) treating the subject with at least one antibody to the cat allergen; d) exposing the subject to at least one cat allergen; e) generating or having generated a fourth transcriptome for the subject after exposing the subject to at least one cat allergen in step d); and e) screening the fourth transcriptome against the third transcriptome to generate a cat allergen exposure/treatment/exposure transcriptome; wherein the subject is suitable for the treatment or prevention of asthma exacerbation induced by a cat allergen with at least one antibody to the cat allergen when the cat allergen exposure/treatment/exposure transcriptome comprises: a downregulation of at least any ten of the following genes: LOC100132062, CCL8, AK128563, BC048201, LOC100133669, IL17D, RGS13, DKFZp434J0226, PMF1-BGLAP, LOC643802, AK123177, SPP1, BC041030, AK001975, THBS4, BC047364, CNGB3, FAM27C, SRMS, CXCL13, COL22A1, BC064137, AK055853, OCLM, PSORS1C2, AX746492, KCNA7, EFCAB3, NCAM1, PRR5-ARHGAP8, CNDP1, MSI1, BX648826, GFRA3, DACT1, AX748314, CNN1, BC107108, PCP2, LRRC63, SNAP25-AS1, ESYT3, HIST1H1D, AK129879, CASQ2, SLC16A10, CRISP3, KIAA0931, DQ588114, AX747628, AK022787, GFRA1, LIN7A, OXER1, LILRA5, AX748175, AK125412, LHFPL5, PTPLA, AX748417, AF119915, EMX2, PCDHGC4, SEPT12, BPIFB4, CILP, ADAMTS1, BHMT2, LINC00937, AX747864, TLDC2, BMP6, MMP9, MAP1LC3C, MSRB3, AK095583, LOC729444, DQ599872_2, MAGOH2, BC041484, TTYH1, PLA2G4E, PDE1B, CCR3, C22orf26, NAT2, AK125288, DPEP3, EDA2R, PYHIN1, CYSLTR2, GPR83, AX746564_2, SMIM1, AK311167, 7SK_25, LOC100288142, PAI1, ANKS4B, LMO3, AK097351, AK054921, PATE2, AK057519, KIAA0087, AK310030, CPXM2, RUNX1T1, LOC100506801, TMEM31, ZNF724P, AK311374, GNGT2, GRID1, PTCD1, AB209185, PPP1R27, FUT7, NXPH2, NECABI, BC039386, S100A5, SFTPD, KU-MEL-3, SALL1, BC070322, MYH6, AF086102, CLUL1, APOBEC2, RPL23P8, COL19A1, LRFN2, RAB3A, ANO3, RPS2P32, FOLR2, AK055332, FBN3, MYOZ3, NCRUPAR, AX748230, CCDC110, SLC13A1, LOC100270746, EPOR, TMEM252, LRFN1, CES1P2, MAL, ADH1A, ILDR2, CA10, SCHIP1, SND1-IT1, BC042024, NHSL2, KLRF2, PIEZO2, AL390170, BC021693, FAM198B, TIPARP-AS1, CD22, OLFM3, GNB3, BC042046, BC041007, DRD1, PGLYRP4, IGSF9B, KIF5A, FKSG63, AK123947, OR4F29, NKD2, PCDHA6, FOSL1, LAMB2P1, GBP1P1, AX746775, FRMD1, PCDHB9, AK301549, ALB, Metazoa_SRP_39, LOC100288911, ENTPD1-AS1, AX747405, FAM180A, MI0003602, ZNF891, SPATA31D5P, LSMEM1, PMS2L14, AK093534, TEX40, AK097590, SERPINB7, BC047540, KRT73, BC049825, TMPRSS6, TMEM200B, MAGEA2, BC047723, BMP2, HSD3B2, AIPL1, KCNA2, BC029473, SCN4A, CCDC116, GGN, KCNJ8, MI0000285, DDX4, LOC283177, MMP7, REM2, CYP17A1, NINJ2, LOC100506060, AX746750, ADAMTSL5, GPR143, WASH6P, CD2, SPDYE6, U4_5, and MKRN3; and an upregulation of at least any twenty of the following genes: ITGA9, RAB40AL, APLN, DCSTAMP, COL8A1, VRTN, SSMEM1, ALDH1L1-AS1, HNF1A, TOB2P1, INO80B, Metazoa_SRP_17, COL4A4, LINC00112, UGT2B28, VAX2, GAD1, CAPNS2, TUSC5, RBM46, LOC728739, LGSN, DQ574505, HYAL4, LOC100505474, TCRBV13S6A2T, C3orf70, UNC5D, TRAV20, CDKN3, ZNF774, RBM11, SHISA3, C9orf170, RBP5, NPAS1, CDY2A, STBD1, LOC441081, BC019672, CST9, P2RY4, CNBD1, DL490887, PCDHGA10, ZNF382, LDLRAD2, SLAMF9, CCNA2, AWAT2, AB586698, SLC25A21-AS1, MT1IP, OCA2, SFTA1P, AK057259, ATP1A10S, GCSAML-AS1, LOC100130557, NXNL2, HSF2BP, CYP4Z2P, FU41941, SNORA66, CD1A, AK301968, ROR2, LOC339290, ITIH1, AK300656, QRFPR, TCP11, SLC35F1, ASCL1, TCRBV9S1A1T, TRPM2, DCC, SIRPD, KRTAP5-2, LOC100133050, MB21D2, POLN, CARD9, ZNF556, LOC148709, MEP1A, STAU2-AS1, BSN, DQ658414, SLC2A14, SPESP1, BLOC1S5, F2RL3, AHSG, LOC100505841, IQGAP3, AK127124, FAM182B, BC030152, TEX21P, PABPC1P2, UMODL1, TCRBV3S1, FMO9P, BC033983, KRTAP5-10, RASAL2-AS1, AJ606331, SH2D6, DSG1, LEMD1, NKAIN2, CR933665, BX648502, LOC286297, LOC647859, BC053679, VWCE, JN120857, ALPPL2, ALX4, Metazoa_SRP_66, WEE2, SPARC, SPTB, SLC22A13, GPR37, POU6F2, F12, PDGFRA, TPPP2, RPL13AP20, KNCN, FU30838, AIFM3, BLOC1S1-RDH5, ZNF177, RAB9B, ZNF815P, TRAV12-1, LOC339047, BC070061, SLC2A5, BC046483, ATOH7, UTS2B, LOC100289388, MCF2L2, COL9A1, CXorf57, BC017910, SUMO1P3, MATN1-AS1, IGLL5, DQ577420, CCDC73, FAM95B1, LOC100289092, PNMA2, AK125437, SLC7A5P2, ZNF367, LOC100131060, C11orf53, MRVI1-AS1, RUSC1-AS1, LOC51326, DSCR9, TRGC2, NPSR1-AS1, ABCB4, AX746969, CRB2, ESM1, ADAMTS15, GPR25, CDH17, NIM1, FU38723, LOC100129138, LIN7B, SLC47A2, IL36G, GOLGA8T, WFDC1, FOXD2-AS1, OR7D2, GPR63, FOXD4L1, LOC100507537, BC036361, BC070106, BEND4, CYS1, FU23584, GRIP2, CKLF-CMTM1, SPINK6, SARDH, HS3ST3B1, LOC643723, DJ031142, SMAD5-S1, AJ420489, PDE2A, EIF5AL1, UCN, SNPH, ANO7, SPC25, AX747264, SNORA6, SEC14L4, HLA-DPB2, C2orf27A, AX747125, SSR4P1, TFAP2B, BC045163, KIF18B, LOC644145, RFPL1S, IL9R, SNORA52, DPRXP4, LOC285768, CHKB-AS1, BCL2L2-PABPN1, STXBP5L, AK309988, DLEU7, SLFNL1-AS1, GABRR1, C10orf55, LOC100131655, NR5A2, OLFM2, DL492607, ADAM12, TDRD9, FAM74A4, BC062769, SLC30A4, LOC339874, LOC100128531, AK097190, BC080653, PEG3, RBFADN, FAM64A, CR627206, ETV2, GPSM1, PKNOX2, AK309255, PI16, SLC4A10, TUBB4A, AKR1C4, C17orf67, AX746484, SLC7A9, LOC643355, LOC645166, SLC28A1, FAM225B, ZNF663, GLB1L3, AK055272, ASGR2, ZCCHC18, LINC00312, BMPER, SYT2, CAMK2A, GRK7, HEATR4, BC023651, AK095633, CSPG4, SNORA81, U1_10, BC065373, AK056432, BC040572, RAB40A, BC040208, HABP2, MGC16142, PEBP4, CCDC154, LOC440934, AK128837, BVES, IGSF1, AX746944, AB075492, MYH16, RFTN2, LOC100130015, TLE6, AX746627, MUC3B, CABC1, LOC285972, BC024248, COL5A3, NSFP1, ANKRD55, TRA@, PRSS30P, ZNF385D, AK098783, CORT, TLR9, KCND2, AK095546, FAM35BP, ATP5J2-PTCD1, RAD51L3-RFFL, and LOC727751.

The present disclosure also provides methods of treating a subject having asthma exacerbation induced by a cat allergen or preventing a subject from developing asthma exacerbation induced by a cat allergen, the methods comprising administering at least one antibody to the cat allergen to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate several features of the present disclosure.

FIG. 1, Panel B shows a representative overview of a 1703 FelD1 study design and sample.

FIG. 1, Panel C shows a representative integration of Blocks A, B, C, and D (from Panel B) into the representative overview of a validated EEU (from Panel A).

FIG. 2, Panel B shows a depiction of a second comparison between the transcriptomes from subjects exposed to cat allergen before treatment (Block B) and after treatment (Block D).

DESCRIPTION

Figure 1:
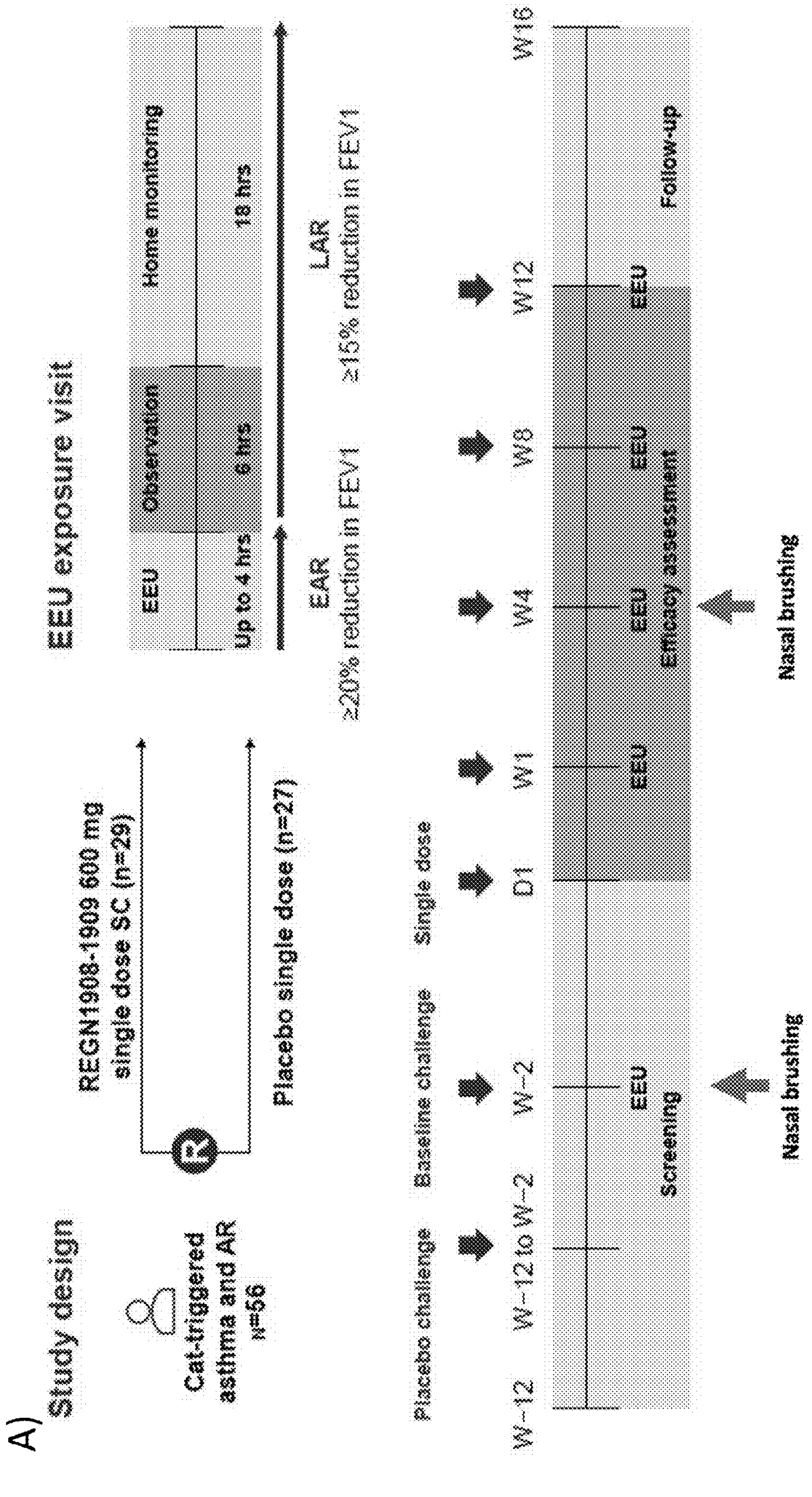
FIG. 1, Panel A shows a representative overview of a validated EEU used as a challenge model to evaluate the effectiveness of REGN1908/1909 to inhibit cat allergen-provoked asthma exacerbations in cat-allergic mild asthmatics.
Figure 1:
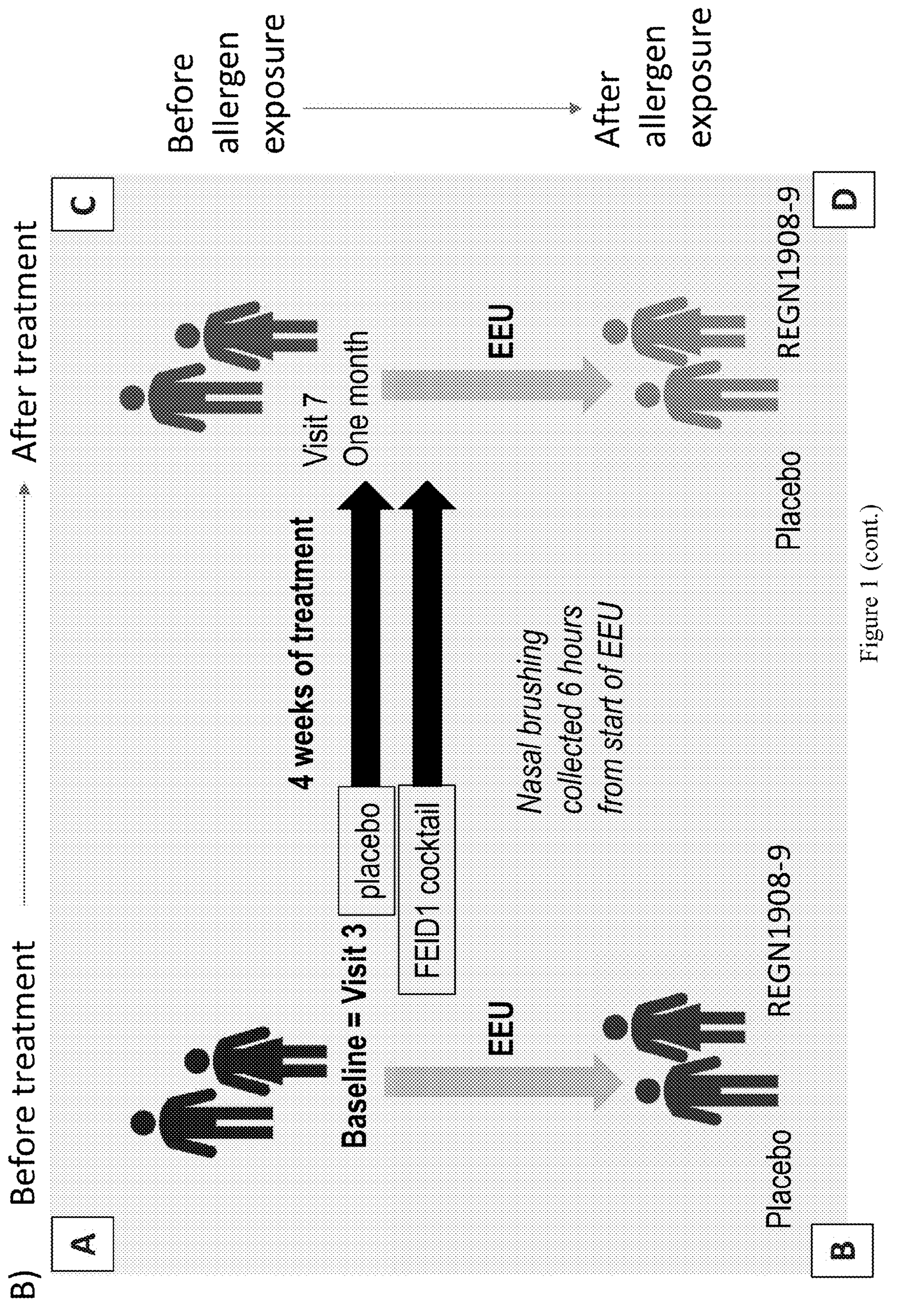
Figure 1:
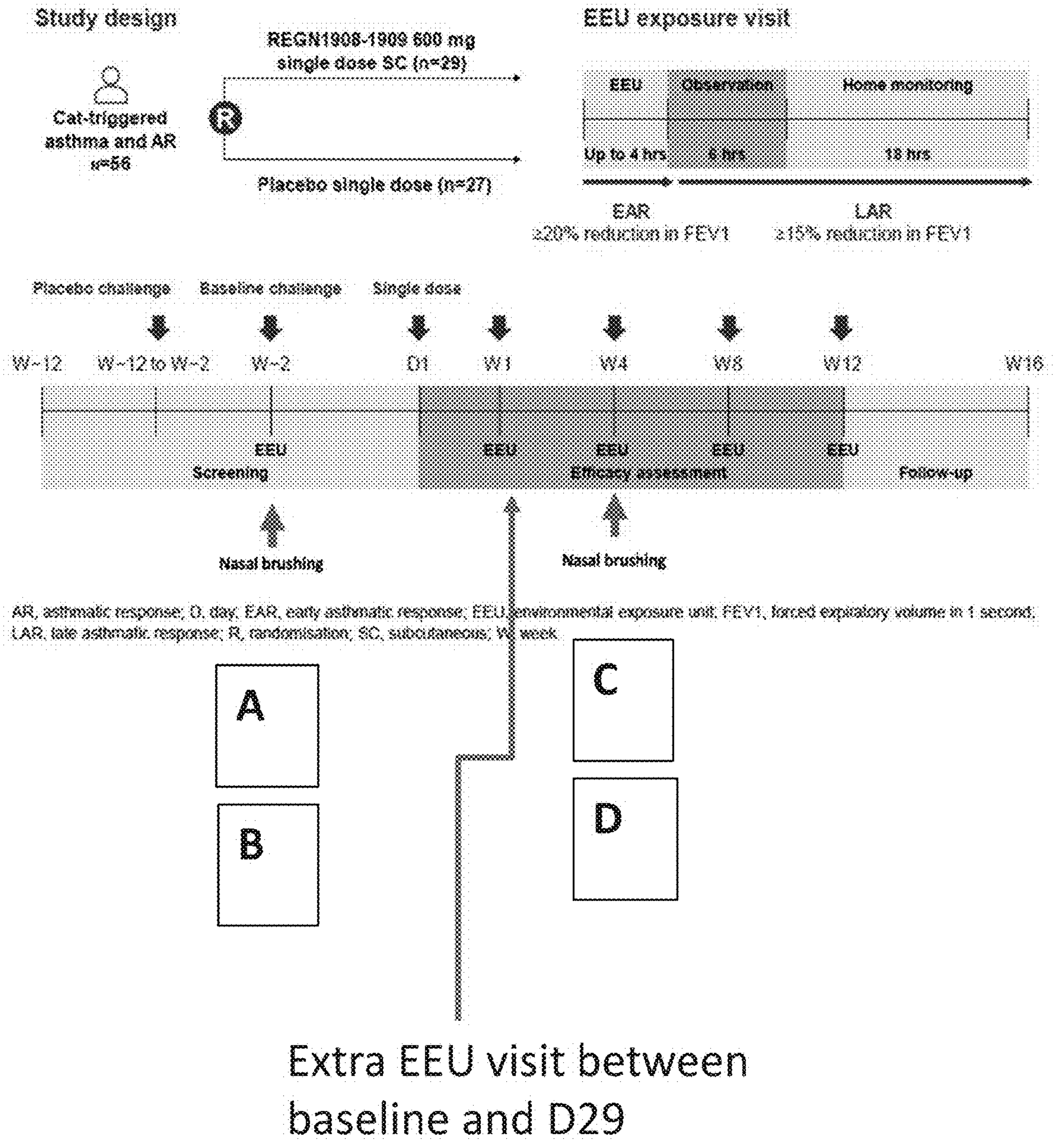

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is not intended that any method or aspect set forth herein be construed as requiring that its steps be performed in a specific order. Accordingly, where a method claim does not specifically state in the claims or descriptions that the steps are to be limited to a specific order, it is not intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician or a veterinarian.

As used herein, a list comprising A, B, "and/or" C provides: (i) A alone; (ii) B alone; (iii) C alone; (iv) A and B; (v) A and C; (vi) B and C; and (viii) A, B, and C. Thus, a list comprising A, B, C, . . . , and/or N has n constituents, where n is a positive integer provides all possible combinations of A, B, C, . . . N up to and including a combination of all n constituents.

In the process of drug discovery, it is beneficial to identify existing approved drugs effective to new indications (be it a disease, condition, or disorder), or a subset of patient population that would better respond to the existing drug. In traditional drug effect studies, single gene analysis upon drug treatment (i.e., t-test) for each individual gene is utilized to identify suitable biomarkers to a target, and to alter such biomarker's level to achieve a presumed treatment effect. This approach, however, may lead to the creation of a long list of statistically significant genes without connecting their biological relevance. In addition, such gene lists among different clinical studies may have little overlap; and most importantly, they may miss the pathway effects of each gene involved in the disease, condition, or treatment effects. For example, several small gene expression changes, although individually not significant in t-test, may have a more collective impact on a particular disease or condition, than one gene that changes quite a bit but has negligible effects on the disease or condition. To avoid such an outcome, a genome wide approach is developed in this disclosure, wherein a core gene signature set in risk profile and/or a drug's clinical study is first identified, compared with a whole transcriptome profile of interest, to obtain a normalized enrichment score for use to identify an appropriate indication or patient population to respond to the drug.

The present disclosure provides methods of identifying a subject as suitable for the treatment or prevention of asthma exacerbation induced by a cat allergen with at least one antibody to the cat allergen. In some embodiments, the methods can be used to identifying a subject as suitable for the treatment or prevention of allergic rhinitis without asthma induced by a cat allergen with at least one antibody to the cat allergen. In some embodiments, the methods can be used to identifying a subject as suitable for the treatment or prevention of allergic asthma induced by a cat allergen with at least one antibody to the cat allergen. In some embodiments, the methods identify a subject as suitable for the treatment of asthma exacerbation induced by a cat allergen with at least one antibody to the cat allergen. In some embodiments, the methods identify a subject as suitable for the prevention of asthma exacerbation induced by a cat allergen with at least one antibody to the cat allergen.

The methods comprise generating or having generated a first transcriptome for the subject. The methods also comprise exposing the subject to at least one cat allergen. The methods also comprise generating or having generated a second transcriptome for the subject after exposure to the at least one cat allergen. The methods also comprise screening the second transcriptome against the first transcriptome to generate a cat allergen exposure transcriptome.

The methods also comprise generating or having generated a first transcriptome for the subject. The methods also comprise exposing the subject to at least one cat allergen and treatment. The methods also comprise generating or having generated a third transcriptome for the subject after exposure to the at least one cat allergen and treatment. The methods also comprise screening the third transcriptome against the first transcriptome to generate a cat allergen exposure/treatment transcriptome.

The methods also comprise generating or having generated a fourth transcriptome for the subject. The methods also comprise exposing the subject to at least one cat allergen and treatment (and generating the second transcriptome), followed by a second cat allergen exposure. The methods also comprise generating or having generated a fourth transcriptome for the subject after exposure to the at least one cat allergen, treatment and exposure. The methods also comprise screening the fourth transcriptome against the second transcriptome to generate a cat allergen exposure/treatment/exposure transcriptome.

The subject is suitable for the treatment or prevention of asthma exacerbation induced by a cat allergen with at least one antibody to the cat allergen when the cat allergen exposure transcriptome comprises: i) a downregulation of at least any 5, at least any 10, at least any 15, at least any 20, at least any 25, or at least any 30 of the following genes: CCDC33, ADH6, IFLTD1, DLGAP1-AS5, DNAJB13, C2orf62, CCDC81, PIH1D3, NHLRC4, TMEM190, AK090700, KIF6, BBOX1, PTGFR, SEC14L3, BC022056, CASC2, PPP1R36, CNTN5, KLHDC8A, FHOD3, CAPS, UBD, TP73, BC023516, IFI44L, FAM86B1, CX3CL1, ACY3, MPDZ, IGFBP5, AK097288, IF16, ABCC6, GAS1, and PLCH1; and ii) an upregulation of at least any 10, at least any 20, at least any 30, at least any 40, at least any 50, or at least any 60 of the following genes: ESPL1, NMU, CTSL2, CLIC3, CRABP2, AX746775, TMPRSS11A, NCCRP1, MSX2, HSP90AB4P, AIM1L, SERPINB2, IL1RN, KLK10, PXDN, HSPB8, CLCA4, KRT10, ZBED2, DSC2, LY6G6C, ADAMTSL4, OTOP3, FGFBP1, GPR115, TRPV3, CRISP3, SPRR3, PRSS3, A2ML1, SPINK7, LYPD3, RHCG, SPRR1A, MAP2, S100A8, RPTN, PRSS27, KRT6B, PPP2R2C, IL1RL1, CAMK2N1, CPA4, KLK13, SERPINB13, ALOX12, SLC39A2, KRT4, HOPX, FAM25A, EMP1, CNFN, KLK12, APOBEC3A, CAPN14, IVL, KLK8, SPRR1B, IGFBP6, IL36G, KLK7, EGR3, KRT78, CRNN, MAL, LINC00707, KRT24, KRT6A, TMPRSS11B, KRT14, PRB3, KRT13, LOC731424, and BCL2L2-PABPN1. In some embodiments, the subject is suitable for the treatment or prevention of asthma exacerbation induced by a cat allergen with at least one antibody to the cat allergen when the cat allergen exposure transcriptome comprises: i) a downregulation of at least any 5 of the aforementioned downregulated genes; and an upregulation of at least any 10 of the aforementioned upregulated genes. In some embodiments, the subject is suitable for the treatment or prevention of asthma exacerbation induced by a cat allergen with at least one antibody to the cat allergen when the cat allergen exposure transcriptome comprises: i) a downregulation of at least any 10 of the aforementioned downregulated genes; and an upregulation of at least any 20 of the aforementioned upregulated genes. In some embodiments, the subject is suitable for the treatment or prevention of asthma exacerbation induced by a cat allergen with at least one antibody to the cat allergen when the cat allergen exposure transcriptome comprises: i) a downregulation of at least any 15 of the aforementioned downregulated genes; and an upregulation of at least any 30 of the aforementioned upregulated genes. In some embodiments, the subject is suitable for the treatment or prevention of asthma exacerbation induced by a cat allergen with at least one antibody to the cat allergen when the cat allergen exposure transcriptome comprises: i) a downregulation of at least any 20 of the aforementioned downregulated genes; and an upregulation of at least any 40 of the aforementioned upregulated genes. In some embodiments, the subject is suitable for the treatment or prevention of asthma exacerbation induced by a cat allergen with at least one antibody to the cat allergen when the cat allergen exposure transcriptome comprises: i) a downregulation of at least any 25 of the aforementioned downregulated genes; and an upregulation of at least any 50 of the aforementioned upregulated genes. In some embodiments, the subject is suitable for the treatment or prevention of asthma exacerbation induced by a cat allergen with at least one antibody to the cat allergen when the cat allergen exposure transcriptome comprises: i) a downregulation of at least any 30 of the aforementioned downregulated genes; and an upregulation of at least any 60 of the aforementioned upregulated genes. In some embodiments, the subject is suitable for the treatment or prevention of asthma exacerbation induced by a cat allergen with at least one antibody to the cat allergen when the cat allergen exposure transcriptome comprises: i) a downregulation of all of the aforementioned downregulated genes; and an upregulation of all of the aforementioned upregulated genes.

In some embodiments, any 1, any 2, any 3, any 4, or any five of the downregulated genes described herein can be omitted from the gene expression analysis. In some embodiments, any 1, any 2, any 3, any 4, any 5, any 6, any 7, any 8, any 9, any 10, any 11, any 12, any 13, any 14, any 15, any 16, any 17, any 18, any 19, or any 20 of the upregulated genes described herein can be omitted from the gene expression analysis.

The methods comprise generating or having generated a first transcriptome for the subject. In some embodiments, the end user of the methods described herein generates the first transcriptome for the subject. In some embodiments, a third party generates the first transcriptome for the subject, wherein the end user of the methods described herein receives the first transcriptome information from the third party or the subject. In some embodiments, generating or having generated a first transcriptome for the subject comprises a first quantification of expression of any combination of the downreglated and upregulated genes described herein. In some embodiments, generating or having generated a first transcriptome for the subject comprises a first quantification of expression of at least one RNA derived from the gene. In some embodiments, the at least one RNA derived from the gene comprises at least one messenger RNA, at least one long non-coding RNA, at least one mitochondrial rRNA, at least one mitochondrial tRNA, at least one rRNA, at least one ribozyme, at least one B-cell receptor subunit constant gene, and/or at least one T-cell receptor subunit constant gene. In some embodiments, the at least one RNA derived from the gene comprises at least one messenger RNA. In some embodiments, the at least one RNA derived from the gene comprises at least one long non-coding RNA. In some embodiments, the at least one RNA derived from the gene comprises at least one mitochondrial rRNA. In some embodiments, the at least one RNA derived from the gene comprises at least one mitochondrial tRNA. In some embodiments, the at least one RNA derived from the gene comprises at least one rRNA. In some embodiments, the at least one RNA derived from the gene comprises at least one ribozyme. In some embodiments, the at least one RNA derived from the gene comprises at least one B-cell receptor subunit constant gene. In some embodiments, the at least one RNA derived from the gene comprises at least one T-cell receptor subunit constant gene. The first transcriptome represents a cat allergic patient without allergen exposure transcriptome.

The methods comprise exposing the subject to at least one cat allergen. In some embodiments, exposing the subject to at least one cat allergen comprises exposing the subject to at least one cat for at least 30 minutes, at least 1 hour, at least 2 hours, at least 3 hours, at least 4 hours, at least 5 hours, or at least 6 hours. In some embodiments, exposing the subject to at least one cat allergen comprises exposing the subject to at least one cat for at least 30 minutes. In some embodiments, exposing the subject to at least one cat allergen comprises exposing the subject to at least one cat for at least 1 hour. In some embodiments, exposing the subject to at least one cat allergen comprises exposing the subject to at least one cat for at least 2 hours. In some embodiments, exposing the subject to at least one cat allergen comprises exposing the subject to at least one cat for at least 3 hours. In some embodiments, exposing the subject to at least one cat allergen comprises exposing the subject to at least one cat for at least 4 hours. In some embodiments, exposing the subject to at least one cat allergen comprises exposing the subject to at least one cat for at least 5 hours. In some embodiments, exposing the subject to at least one cat allergen comprises exposing the subject to at least one cat for at least 6 hours. In some embodiments, exposing the subject to at least one cat occurs in a naturalistic exposure chamber (NEC) or an environmental exposure unit (EEU). In some embodiments, exposing the subject to at least one cat occurs in an NEC. In some embodiments, exposing the subject to at least one cat occurs in an EEU. In some embodiments, the subject is exposed to at least one cat in the NEC or EEU for no longer than two hours.

In some embodiments, exposing the subject to at least one cat allergen comprises exposing the subject to cat dander or at least one cat allergen for at least 30 minutes, at least 1 hour, at least 2 hours, at least 3 hours, at least 4 hours, at least 5 hours, or at least 6 hours. In some embodiments, exposing the subject to at least one cat allergen comprises exposing the subject to cat dander or at least one cat allergen for at least 30 minutes. In some embodiments, exposing the subject to at least one cat allergen comprises exposing the subject to cat dander or at least one cat allergen for at least 1 hour. In some embodiments, exposing the subject to at least one cat allergen comprises exposing the subject to cat dander or at least one cat allergen for at least 2 hours. In some embodiments, exposing the subject to at least one cat allergen comprises exposing the subject to cat dander or at least one cat allergen for at least 3 hours. In some embodiments, exposing the subject to at least one cat allergen comprises exposing the subject to cat dander or at least one cat allergen at least 4 hours. In some embodiments, exposing the subject to at least one cat allergen comprises exposing the subject to cat dander or at least one cat allergen for at least 5 hours. In some embodiments, exposing the subject to at least one cat allergen comprises exposing the subject to cat dander or at least one cat allergen for at least 6 hours. In some embodiments, exposing the subject to at least one cat allergen comprises administering or having administered to the subject cat dander or the at least one cat allergen to the skin of the subject or to the nasal mucosa of the subject. In some embodiments, exposing the subject to at least one cat allergen comprises administering or having administered to the subject cat dander or the at least one cat allergen to the skin of the subject. In some embodiments, exposing the subject to at least one cat allergen comprises administering or having administered to the subject cat dander or the at least one cat allergen to the nasal mucosa of the subject. In some embodiments, the biological sample is obtained from the nasal mucosa via a nasal brushing.

In some embodiments, the cat dander comprises Fel d 1, Fel d 2, Fel d 3, Fel d 4, Fel d 5, Fel d 6, Fel d 7, or Fel d 8, or any combination thereof. In some embodiments, the at least one cat allergen comprises Fel d 1, Fel d 2, Fel d 3, Fel d 4, Fel d 5, Fel d 6, Fel d 7, or Fel d 8, or any combination thereof. In some embodiments, the at least one cat allergen comprises Fel d 1. In some embodiments, the at least one cat allergen comprises Fel d 2. In some embodiments, the at least one cat allergen comprises Fel d 3. In some embodiments, the at least one cat allergen comprises Fel d 4. In some embodiments, the at least one cat allergen comprises Fel d 5. In some embodiments, the at least one cat allergen comprises Fel d 6. In some embodiments, the at least one cat allergen comprises Fel d 7. In some embodiments, the at least one cat allergen comprises Fel d 8.

The methods comprise generating or having generated a second transcriptome for the subject after exposure to the at least one cat allergen. In some embodiments, the end user of the methods described herein generates the second transcriptome for the subject. In some embodiments, a third party generates the second transcriptome for the subject, wherein the end user of the methods described herein receives the second transcriptome information from the third party or the subject. In some embodiments, generating or having generated a second transcriptome for the subject comprises a second quantification of expression of any combination of the downreglated and upregulated genes described herein. In some embodiments, generating or having generated a second transcriptome for the subject comprises a second quantification of expression of at least one RNA derived from the gene. In some embodiments, the at least one RNA derived from the gene comprises at least one messenger RNA, at least one long non-coding RNA, at least one mitochondrial rRNA, at least one mitochondrial tRNA, at least one rRNA, at least one ribozyme, at least one B-cell receptor subunit constant gene, and/or at least one T-cell receptor subunit constant gene. In some embodiments, the at least one RNA derived from the gene comprises at least one messenger RNA. In some embodiments, the at least one RNA derived from the gene comprises at least one long non-coding RNA. In some embodiments, the at least one RNA derived from the gene comprises at least one mitochondrial rRNA. In some embodiments, the at least one RNA derived from the gene comprises at least one mitochondrial tRNA. In some embodiments, the at least one RNA derived from the gene comprises at least one rRNA. In some embodiments, the at least one RNA derived from the gene comprises at least one ribozyme. In some embodiments, the at least one RNA derived from the gene comprises at least one B-cell receptor subunit constant gene. In some embodiments, the at least one RNA derived from the gene comprises at least one T-cell receptor subunit constant gene.

The methods comprise screening the second transcriptome against the first transcriptome to generate a cat allergen exposure transcriptome. In some embodiments, screening the second transcriptome against the first transcriptome to generate the cat allergen exposure transcriptome comprises determining or having determined the differential gene expression in the second transcriptome with respect to the first transcriptome. The differential gene expression reveals the genes that have been downregulated upon exposure to the at least one cat allergen and genes that have been upregulated upon exposure to the at least one cat allergen. Downregulation and upregulation of genes can be determined by measuring the changes in expression of any of the RNA molecules described herein and/or the production of polypeptides. In some embodiments, the upregulation, downregulation, and differential gene expression is determined by a microarray or RNASeq. In some embodiments, the upregulation, downregulation, and differential gene expression is determined by a microarray. In some embodiments, the upregulation, downregulation, and differential gene expression is determined by RNASeq. In some embodiments, reverse transcription polymerase chain reaction (RT-PCR) can be used to measure gene expression.

In some embodiments, RNA sequencing reads can be mapped to a genome. In some embodiments, the genome is the human genome. In some embodiments, the human genome is reference assembly GRCh38. In some embodiments, the sequences can be mapped without strand specificity, with strand-specific reverse first-read mapping, or with strand-specific forward first-read mapping. In some embodiments, the sequences can be mapped using kallisto v0.45.0 with strand-specific reverse first-read mapping (Bray et al., Nat. Biotechnol., 2016, 34, 525). In some embodiments, transcript counts can be aggregated to gene counts. In some embodiments, the aggregation can be conducted using tximport (Soneson et al., F1000Research, 2015, 4, 1521).

In any of the methods described herein whereby a second transcriptome is screened against a first transcriptome to generate a cat allergen exposure transcriptome, particular thresholds can be used to determine whether a gene is considered to be upregulated or downregulated sufficiently in order to be included in the list of upregulated or downregulated genes described herein. For example, in some embodiments, the listed genes in the transcriptome identified from the screening can be selected to have a fold-change ≥2, and a $q<0.05$ in at least one study. In some embodiments, the listed genes in the transcriptome identified from the screening can be selected to have a fold-change ≥1.5, and a $q<0.05$ in at least one study. Alternately, a p value can be used instead of q value. In some embodiments, the listed genes in the transcriptome identified from the screening can be selected to have a $p<0.05$ in at least one study.

In some embodiments, screening a second transcriptome against a first transcriptome to generate a cat allergen exposure transcriptome is carried out by comparing the baseline gene expression before exposure to the at least one cat allergen to the gene expression after exposure to the at least one cat allergen. In some embodiments, the second transcriptome is generated from a biological sample that is obtained 30 minutes after exposure to the at least one cat allergen. In some embodiments, the second transcriptome is generated from a biological sample that is obtained about 1 hour after exposure to the at least one cat allergen. In some embodiments, the second transcriptome is generated from a biological sample that is obtained about 1.5 hours after exposure to the at least one cat allergen. In some embodiments, the second transcriptome is generated from a biological sample that is obtained about 2 hours after exposure to the at least one cat allergen. In some embodiments, the second transcriptome is generated from a biological sample that is obtained about 3 hours after exposure to the at least one cat allergen. In some embodiments, the second transcriptome is generated from a biological sample that is obtained about 4 hours after exposure to the at least one cat allergen. In some embodiments, the second transcriptome is generated from a biological sample that is obtained about 5 hours after exposure to the at least one cat allergen. In some embodiments, the second transcriptome is generated from a biological sample that is obtained about 6 hours after exposure to the at least one cat allergen. In some embodiments, the second transcriptome is generated from a biological sample that is obtained about 12 hours after exposure to the at least one cat allergen. In some embodiments, the second transcriptome is generated from a biological sample that is obtained about 18 hours after exposure to the at least one cat allergen. In some embodiments, the second transcriptome is generated from a biological sample that is obtained about 24 hours after exposure to the at least one cat allergen. In some embodiments, the second transcriptome is generated from a biological sample that is obtained at peak allergen exposure to the at least one cat allergen.

In some embodiments, the screening of the second transcriptome against the first transcriptome comprises: i) transforming the first transcriptome into z-scores; ii) ranking the z-scores; and ii) generating a gene expression signature (GES) for all ranked z-scores using at least one gene which is differentially expressed and is in the first transcriptome, thereby representing at least one change in the second transcriptome with respect to the first transcriptome. In some embodiments, the GES is generated using a gene set enrichment analysis tool that takes both at least one positive gene set and at least one negative gene set into consideration. In some embodiments, the GES is generated by: a) transforming each gene expression within at least one gene into a z-score, and ordering at least one gene that is differentially expressed from the most upregulated to the most downregulated values to generate a value of R+; b) identifying hits independently for the most up-regulated gene set (S+) in R+, and the most downregulated gene set (S−) in R−, wherein R− is the inversed ranking of R+ with inverted values; c) combining R+ and R− and reordering the values by keeping the hits for both S+ and S−; d) computing a running score by walking down the combined ranking, wherein the running score increases by $/r_i/^p/\Sigma_{i \in S}/r/^p$ if the $i^{th}$ gene is a hit, or decreases by 1/(2N−S), where S is the combined total number of genes in S+ and S−; $r_i$ is the value for gene i, and p is the weight for r; e) determining an Enrichment Score (ES) as a maximum deviation from zero along the running score; f) repeating steps a)-e) with a random gene set for 1,000 times to compute the ES null distribution; and g) generating the NES as ES divided by the mean of ES null distribution. In some embodiments, the methods further comprise computing the statistical significance by determining the $95^{th}$ percentile GES from healthy control samples. In some embodiments, when the GES of the subject is higher than the GES of a healthy control, the subject is suitable for the antibody treatment.

In any of the methods described herein, the methods can further comprise obtaining or having obtained a first biological sample and/or a second biological sample from the subject for generating or having generated the first transcriptome and/or second transcriptome, respectively. In some embodiments, the end user of the methods described herein obtains the first biological sample and/or the second biological sample from the subject. In some embodiments, a third party obtains the first biological sample and/or the second biological sample from the subject, wherein the end user of the methods described herein receives the first biological sample and/or the second biological sample from the third party or the subject. In some embodiments, the first biological sample and/or second biological sample comprises a sample from an organ, a tissue, a cell, and/or a biological fluid. In some embodiments, the first biological sample and/or second biological sample comprises a sample from an organ. In some embodiments, the first biological sample and/or second biological sample comprises a sample from a tissue. In some embodiments, the first biological sample and/or second biological sample comprises a sample from a cell. In some embodiments, the first biological sample and/or second biological sample comprises a sample from a biological fluid. In some embodiments, the first biological sample and/or second biological sample comprises blood, semen, saliva, urine, feces, hair, teeth, bone, nasal mucosal tissue, bronchial alveolar lavage sample, respiratory tissue sample, and/or a buccal sample. In some embodiments, the first biological sample and/or second biological sample comprises blood. In some embodiments, the first biological sample and/or second biological sample comprises semen. In some embodiments, the first biological sample and/or second biological sample comprises saliva. In some embodiments, the first biological sample and/or second biological sample comprises urine. In some embodiments, the first biological sample and/or second biological sample comprises feces. In some embodiments, the first biological sample and/or second biological sample comprises hair. In some embodiments, the first biological sample and/or second biological sample comprises teeth. In some embodiments, the first biological sample and/or second biological sample comprises bone. In some embodiments, the first biological sample and/or second biological sample comprises nasal mucosal tissue. In some embodiments, the first biological sample and/or second biological sample comprises bronchial alveolar lavage sample. In some embodiments, the first biological sample and/or second biological sample comprises respiratory tissue sample. In some embodiments, the first biological sample and/or second biological sample comprises a buccal sample. In some embodiments, the first biological sample is obtained from the subject by a biopsy. In some embodiments, the first biological sample and/or second biological sample comprises plasma. In some embodiments, the first biological sample and/or second biological sample comprises serum. In some embodiments, the first biological sample and/or second biological sample comprises lymph. In some embodiments, the first biological sample and/or second biological sample comprises semen. In some embodiments, the first biological sample and/or second biological sample comprises a nasal mucosal secretion. In some embodiments, the biological sample is obtained from the nasal mucosa via a nasal brushing.

In some embodiments, the at least one antibody to the cat allergen comprises at least one antibody to Fel d 1. In some embodiments, the at least one antibody to the cat allergen comprises two monoclonal antibodies to Fel d 1. In some embodiments, the two monoclonal antibodies to Fel d 1 are fully human monoclonal antibodies. In some embodiments, the two fully human monoclonal antibodies to Fel d 1 comprises REGN1908 and REGN1909 (see, U.S. Pat. Nos. 9,079,948; 10,047,153; and 11,352,417).

In any of the embodiments described herein, the subject or patient has a documented or patient reported history (e.g., for at least 2 years) of symptomatic cat allergen-triggered asthma with rhinitis with or without conjunctivitis as defined by all of the following criteria: 1) a positive skin prick test (SPT) with cat hair extract (e.g., mean wheal diameter at least 5 mm greater than a negative control) at screening; 2) a positive allergen-specific IgE (sIgE) test for cat hair and Fel d 1 (e.g., >0.35 kAU/l at screening); and 3) a history of asthma (e.g., Global Initiative for Asthma (GINA) 1).

The present disclosure also provides methods of identifying a subject as suitable for the treatment or prevention of asthma exacerbation induced by a cat allergen with at least one antibody to the cat allergen. In some embodiments, the methods identify a subject that is suitable for the treatment of asthma exacerbation induced by a cat allergen with at least one antibody to the cat allergen. In some embodiments, the methods identify a subject that is suitable for the prevention of asthma exacerbation induced by a cat allergen with at least one antibody to the cat allergen. In some embodiments, the methods can be used to identifying a subject as suitable for the treatment or prevention of allergic rhinitis without asthma induced by a cat allergen with at least one antibody to the cat allergen. In some embodiments, the methods can be used to identifying a subject as suitable for the treatment or prevention of allergic asthma induced by a cat allergen with at least one antibody to the cat allergen. The methods comprise generating or having generated a first transcriptome for the subject before exposure to at least one cat allergen. The methods also comprise exposing the subject to the at least one cat allergen. The methods also comprise treating the subject with at least one antibody to the cat allergen. The methods also comprise generating or having generated a second transcriptome for the subject after treatment with at least one antibody to the cat allergen. The methods also comprise screening the second transcriptome against the first transcriptome to generate a cat allergen exposure/treatment transcriptome.

The subject is suitable for the treatment or prevention of asthma exacerbation induced by a cat allergen with at least one antibody to the cat allergen when the cat allergen exposure/treatment transcriptome comprises: a downregulation of at least any five of the following genes: BC007880, BC080587, BX537909, NGS-17, LOC100862671, AX747215, P2RX1, SDS, S1PR4, RPPH1, ARPC4-TTLL3, and SERPING1; and an upregulation of at least any twenty-five of the following genes: C6orf165, ARHGEF33, LOC157381, ARHGEF26-AS1, IQUB, WDR78, CNTD1, TEX21P, REEP1, RBM24, TMEM212, TEX9, DIO1, ECT2L, GCNT4, FSD1L, MAMDC2, LOC100499484-C90RF174, ADH6, LOC653501, DNAH7, DCDC2, KLHL32, PTGES3L, ADAM22, AKAP6, TEX26, DPY19L2, ZBBX, TXLNB, ANKFN1, CHDC2, CRISPLD1, WDR96, FAM216B, AK057689, TSPAN19, DTHD1, PROS1, DNAH5, AX747851, MYLK, AK090700, SRD5A2, ANGPTL5, TMEM232, CXorf22, AK097702, AK310634, C1orf141, BICC1, FAM86B2, AX747150, PCDHB1, CAPS2, PTPN20B, TCP11X2, GIPC2, GRM5, LOC100130451, C12orf63, FL00322, MTTP, MROH9, SLC16A12, AK307870, MYCT1, AK094325, AX747187, FGF14, PHOSPHO2-KLHL23, CD200R1L, AK126334, PALM2-KAP2, and LY75-CD302.

In some embodiments, the subject is suitable for the treatment or prevention of asthma exacerbation induced by a cat allergen with at least one antibody to the cat allergen when the cat allergen exposure/treatment transcriptome comprises: a downregulation of at least any seven of the following genes: BC007880, BC080587, BX537909, NGS-17, LOC100862671, AX747215, P2RX1, SDS, S1PR4, RPPH1, ARPC4-TTLL3, and SERPING1; and an upregulation of at least any forty of the following genes: C6orf165, ARHGEF33, LOC157381, ARHGEF26-AS1, IQUB, WDR78, CNTD1, TEX21P, REEP1, RBM24, TMEM212, TEX9, DIO1, ECT2L, GCNT4, FSD1L, MAMDC2, LOC100499484-C90RF174, ADH6, LOC653501, DNAH7, DCDC2, KLHL32, PTGES3L, ADAM22, AKAP6, TEX26, DPY19L2, ZBBX, TXLNB, ANKFN1, CHDC2, CRISPLD1, WDR96, FAM216B, AK057689, TSPAN19, DTHD1, PROS1, DNAH5, AX747851, MYLK, AK090700, SRD5A2, ANGPTL5, TMEM232, CXorf22, AK097702, AK310634, C1orf141, BICC1, FAM86B2, AX747150, PCDHB1, CAPS2, PTPN20B, TCP11X2, GIPC2, GRM5, LOC100130451, C12orf63, FU00322, MTTP, MROH9, SLC16A12, AK307870, MYCT1, AK094325, AX747187, FGF14, PHOSPHO2-KLHL23, CD200R1L, AK126334, PALM2-KAP2, and LY75-CD302.

In some embodiments, the subject is suitable for the treatment or prevention of asthma exacerbation induced by a cat allergen with at least one antibody to the cat allergen when the cat allergen exposure/treatment transcriptome comprises: a downregulation of at least any nine of the following genes: BC007880, BC080587, BX537909, NGS-17, LOC100862671, AX747215, P2RX1, SDS, S1PR4, RPPH1, ARPC4-TTLL3, and SERPING1; and an upregulation of at least any fifty of the following genes: C6orf165, ARHGEF33, LOC157381, ARHGEF26-AS1, IQUB, WDR78, CNTD1, TEX21P, REEP1, RBM24, TMEM212, TEX9, DIO1, ECT2L, GCNT4, FSD1L, MAMDC2, LOC100499484-C90RF174, ADH6, LOC653501, DNAH7, DCDC2, KLHL32, PTGES3L, ADAM22, AKAP6, TEX26, DPY19L2, ZBBX, TXLNB, ANKFN1, CHDC2, CRISPLD1, WDR96, FAM216B, AK057689, TSPAN19, DTHD1, PROS1, DNAH5, AX747851, MYLK, AK090700, SRD5A2, ANGPTL5, TMEM232, CXorf22, AK097702, AK310634, C1orf141, BICC1, FAM86B2, AX747150, PCDHB1, CAPS2, PTPN20B, TCP11X2, GIPC2, GRM5, LOC100130451, C12orf63, FU00322, MTTP, MROH9, SLC16A12, AK307870, MYCT1, AK094325, AX747187, FGF14, PHOSPHO2-KLHL23, CD200R1L, AK126334, PALM2-KAP2, and LY75-CD302.

In some embodiments, the subject is suitable for the treatment or prevention of asthma exacerbation induced by a cat allergen with at least one antibody to the cat allergen when the cat allergen exposure/treatment transcriptome comprises: a downregulation of at least any eleven of the following genes: BC007880, BC080587, BX537909, NGS-17, LOC100862671, AX747215, P2RX1, SDS, S1PR4, RPPH1, ARPC4-TTLL3, and SERPING1; and an upregulation of at least any sixty of the following genes: C6orf165, ARHGEF33, LOC157381, ARHGEF26-AS1, IQUB, WDR78, CNTD1, TEX21P, REEP1, RBM24, TMEM212, TEX9, DIO1, ECT2L, GCNT4, FSD1L, MAMDC2, LOC100499484-C90RF174, ADH6, LOC653501, DNAH7, DCDC2, KLHL32, PTGES3L, ADAM22, AKAP6, TEX26, DPY19L2, ZBBX, TXLNB, ANKFN1, CHDC2, CRISPLD1, WDR96, FAM216B, AK057689, TSPAN19, DTHD1, PROS1, DNAH5, AX747851, MYLK, AK090700, SRD5A2, ANGPTL5, TMEM232, CXorf22, AK097702, AK310634, C1orf141, BICC1, FAM86B2, AX747150, PCDHB1, CAPS2, PTPN20B, TCP11X2, GIPC2, GRM5, LOC100130451, C12orf63, FU00322, MTTP, MROH9, SLC16A12, AK307870, MYCT1, AK094325, AX747187, FGF14, PHOSPHO2-KLHL23, CD200R1L, AK126334, PALM2-KAP2, and LY75-CD302.

In some embodiments, the subject is suitable for the treatment or prevention of asthma exacerbation induced by a cat allergen with at least one antibody to the cat allergen when the cat allergen exposure/treatment transcriptome comprises: a downregulation of all of the following genes: BC007880, BC080587, BX537909, NGS-17, LOC100862671, AX747215, P2RX1, SDS, S1PR4, RPPH1, ARPC4-TTLL3, and SERPING1; and an upregulation of all of the following genes: C6orf165, ARHGEF33, LOC157381, ARHGEF26-AS1, IQUB, WDR78, CNTD1, TEX21P, REEP1, RBM24, TMEM212, TEX9, DIO1, ECT2L, GCNT4, FSD1L, MAMDC2, LOC100499484-C90RF174, ADH6, LOC653501, DNAH7, DCDC2, KLHL32, PTGES3L, ADAM22, AKAP6, TEX26, DPY19L2, ZBBX, TXLNB, ANKFN1, CHDC2, CRISPLD1, WDR96, FAM216B, AK057689, TSPAN19, DTHD1, PROS1, DNAH5, AX747851, MYLK, AK090700, SRD5A2, ANGPTL5, TMEM232, CXorf22, AK097702, AK310634, C1orf141, BICC1, FAM86B2, AX747150, PCDHB1, CAPS2, PTPN20B, TCP11X2, GIPC2, GRM5, LOC100130451, C12orf63, FU00322, MTTP, MROH9, SLC16A12, AK307870, MYCT1, AK094325, AX747187, FGF14, PHOSPHO2-KLHL23, CD200R1L, AK126334, PALM2-KAP2, and LY75-CD302.

In some embodiments, any 1, any 2, any 3, any 4, any 5, any 6, any 7, any 8, any 9, or any 10 of the downregulated genes described herein can be omitted from the gene expression analysis. In some embodiments, any 1, any 2, any 3, any 4, any 5, any 6, any 7, any 8, any 9, any 10, any 11, any 12, any 13, any 14, any 15, any 16, any 17, any 18, any 19, or any 20 of the upregulated genes described herein can be omitted from the gene expression analysis. The genes that can be monitored for upregulation or downregulation include, but are not limited to any one or more, or any combination thereof, of the genes listed in Table 2.

In some embodiments, the subject has been previously determined to have a cat allergen exposure/treatment transcriptome. In some embodiments, the cat allergen exposure/ treatment transcriptome comprises: a downregulation of at least any ten of the set of genes described herein, and an upregulation of at least any twenty of the set of genes described herein.

In some embodiments, the subject was previously removed from exposure to at least one cat in an NEC in less than two hours. In some embodiments, the subject comprises any of the cat allergen exposure/treatment transcriptomes described herein.

The methods comprise exposing the subject to at least one cat allergen. In some embodiments, exposing the subject to at least one cat allergen comprises exposing the subject to at least one cat for at least 30 minutes, at least 1 hour, at least 2 hours, at least 3 hours, at least 4 hours, at least 5 hours, or at least 6 hours. In some embodiments, exposing the subject to at least one cat allergen comprises exposing the subject to at least one cat for at least 30 minutes. In some embodiments, exposing the subject to at least one cat allergen comprises exposing the subject to at least one cat for at least 1 hour. In some embodiments, exposing the subject to at least one cat allergen comprises exposing the subject to at least one cat for at least 2 hours. In some embodiments, exposing the subject to at least one cat allergen comprises exposing the subject to at least one cat for at least 3 hours. In some embodiments, exposing the subject to at least one cat allergen comprises exposing the subject to at least one cat for at least 4 hours. In some embodiments, exposing the subject to at least one cat allergen comprises exposing the subject to at least one cat for at least 5 hours. In some embodiments, exposing the subject to at least one cat allergen comprises exposing the subject to at least one cat for at least 6 hours. In some embodiments, exposing the subject to at least one cat occurs in an NEC or an EEU. In some embodiments, exposing the subject to at least one cat occurs in an NEC. In some embodiments, exposing the subject to at least one cat occurs in an EEU. In some embodiments, the subject is exposed to at least one cat in the NEC or EEU for no longer than two hours.

In some embodiments, exposing the subject to at least one cat allergen comprises exposing the subject to cat dander or at least one cat allergen for at least 30 minutes, at least 1 hour, at least 2 hours, at least 3 hours, at least 4 hours, at least 5 hours, or at least 6 hours. In some embodiments, exposing the subject to at least one cat allergen comprises exposing the subject to cat dander or at least one cat allergen for at least 30 minutes. In some embodiments, exposing the subject to at least one cat allergen comprises exposing the subject to cat dander or at least one cat allergen for at least 1 hour. In some embodiments, exposing the subject to at least one cat allergen comprises exposing the subject to cat dander or at least one cat allergen for at least 2 hours. In some embodiments, exposing the subject to at least one cat allergen comprises exposing the subject to cat dander or at least one cat allergen for at least 3 hours. In some embodiments, exposing the subject to at least one cat allergen comprises exposing the subject to cat dander or at least one cat allergen at least 4 hours. In some embodiments, exposing the subject to at least one cat allergen comprises exposing the subject to cat dander or at least one cat allergen for at least 5 hours. In some embodiments, exposing the subject to at least one cat allergen comprises exposing the subject to cat dander or at least one cat allergen for at least 6 hours. In some embodiments, exposing the subject to at least one cat allergen comprises administering or having administered to the subject cat dander or the at least one cat allergen to the skin of the subject or to the nasal mucosa of the subject. In some embodiments, exposing the subject to at least one cat allergen comprises administering or having administered to the subject cat dander or the at least one cat allergen to the skin of the subject. In some embodiments, exposing the subject to at least one cat allergen comprises administering or having administered to the subject cat dander or the at least one cat allergen to the nasal mucosa of the subject.

In some embodiments, the cat dander comprises Fel d 1, Fel d 2, Fel d 3, Fel d 4, Fel d 5, Fel d 6, Fel d 7, or Fel d 8, or any combination thereof. In some embodiments, the at least one cat allergen comprises Fel d 1, Fel d 2, Fel d 3, Fel d 4, Fel d 5, Fel d 6, Fel d 7, or Fel d 8, or any combination thereof. In some embodiments, the at least one cat allergen comprises Fel d 1. In some embodiments, the at least one cat allergen comprises Fel d 2. In some embodiments, the at least one cat allergen comprises Fel d 3. In some embodiments, the at least one cat allergen comprises Fel d 4. In some embodiments, the at least one cat allergen comprises Fel d 5. In some embodiments, the at least one cat allergen comprises Fel d 6. In some embodiments, the at least one cat allergen comprises Fel d 7. In some embodiments, the at least one cat allergen comprises Fel d 8. In some embodiments, from about 10 ng/$m^3$ to about 70 ng/$m^3$ of standardized cat allergen extract can be continuously nebulized into an EEU. In some embodiments, from about 20 ng/$m^3$ to about 60 ng/$m^3$ of standardized cat allergen extract can be continuously nebulized into an EEU. In some embodiments, from about 30 ng/$m^3$ to about 50 ng/$m^3$ of standardized cat allergen extract can be continuously nebulized into an EEU. In some embodiments, about 40 ng/$m^3$ of standardized cat allergen extract can be continuously nebulized into an EEU.

The methods comprise generating or having generated a first transcriptome for the subject before exposure to the at least one cat allergen (and prior to treatment with at least one antibody to a cat allergen). In some embodiments, the end user of the methods described herein generates the first transcriptome for the subject. In some embodiments, a third party generates the first transcriptome for the subject, wherein the end user of the methods described herein receives the first transcriptome information from the third party or the subject. In some embodiments, generating or having generated a first transcriptome for the subject comprises a first quantification of expression of any combination of the downreglated and upregulated genes described herein. In some embodiments, generating or having generated a first transcriptome for the subject comprises a first quantification of expression of at least one RNA derived from the gene. In some embodiments, the at least one RNA derived from the gene comprises at least one messenger RNA, at least one long non-coding RNA, at least one mitochondrial rRNA, at least one mitochondrial tRNA, at least one rRNA, at least one ribozyme, at least one B-cell receptor subunit constant gene, and/or at least one T-cell receptor subunit constant gene. In some embodiments, the at least one RNA derived from the gene comprises at least one messenger RNA. In some embodiments, the at least one RNA derived from the gene comprises at least one long non-coding RNA. In some embodiments, the at least one RNA derived from the gene comprises at least one mitochondrial rRNA. In some embodiments, the at least one RNA derived from the gene comprises at least one mitochondrial tRNA. In some embodiments, the at least one RNA derived from the gene comprises at least one rRNA. In some embodiments, the at least one RNA derived from the gene comprises at least one ribozyme. In some embodiments, the at least one RNA derived from the gene comprises at least one B-cell receptor subunit constant gene. In some embodiments, the at least one RNA derived from the gene comprises at least one T-cell receptor subunit constant gene.

The methods comprise treating the subject with at least one antibody to the cat allergen. In some embodiments, the at least one antibody to the cat allergen comprises at least one antibody to Fel d 1. In some embodiments, the at least one antibody to the cat allergen comprises two monoclonal antibodies to Fel d 1. In some embodiments, the two monoclonal antibodies to Fel d 1 are fully human monoclonal antibodies. In some embodiments, the two fully human monoclonal antibodies to Fel d 1 comprises REGN1908 and REGN1909. In some embodiments, from about 300 mg to about 900 mg of the REGN1908/1909 antibody cocktail can be administered to the subject. In some embodiments, from about 400 mg to about 800 mg of the REGN1908/1909 antibody cocktail can be administered to the subject. In some embodiments, from about 500 mg to about 700 mg of the REGN1908/1909 antibody cocktail can be administered to the subject. In some embodiments, about 600 mg of the REGN1908/1909 antibody cocktail can be administered to the subject. The ratio of REGN1908 to REGN1909 can be 1:1, 0.9:1.1, 0.8:1.2, 0.7:1.3, 0.6:1.4, 0.5:1.5, 1.1:0.9, 1.2:0.8, 1.3:0.7, 1.4:0.6, or 1.5:0.5. In some embodiments, the subject receiving about 600 mg of the REGN1908/1909 antibody cocktail receives 300 mg of each of REGN1908 and REGN1909. The at least one antibody to the cat allergen can be administered by any route of administration including, but not limited to, oral, sublingual, buccal, rectal, intranasal, inhalation, epicutaneous or transdermal, subcutaneous, intradermal, intravenous, intraarterial, intraosseous infusion, intramuscular, intracardiac, intraperitoneal, intravesical infusion, and intravitreal. In some embodiments, the administration is subcutaneous.

The methods comprise generating or having generated a second transcriptome for the subject after cat allergen exposure and after treatment with at least one antibody to the cat allergen. In some embodiments, the end user of the methods described herein generates the second transcriptome for the subject. In some embodiments, a third party generates the second transcriptome for the subject, wherein the end user of the methods described herein receives the second transcriptome information from the third party or the subject. In some embodiments, generating or having generated a second transcriptome for the subject comprises a second quantification of expression of any combination of the downreglated and upregulated genes described herein. In some embodiments, generating or having generated a second transcriptome for the subject comprises a second quantification of expression of at least one RNA derived from the gene. In some embodiments, the at least one RNA derived from the gene comprises at least one messenger RNA, at least one long non-coding RNA, at least one mitochondrial rRNA, at least one mitochondrial tRNA, at least one rRNA, at least one ribozyme, at least one B-cell receptor subunit constant gene, and/or at least one T-cell receptor subunit constant gene. In some embodiments, the at least one RNA derived from the gene comprises at least one messenger RNA. In some embodiments, the at least one RNA derived from the gene comprises at least one long non-coding RNA. In some embodiments, the at least one RNA derived from the gene comprises at least one mitochondrial rRNA. In some embodiments, the at least one RNA derived from the gene comprises at least one mitochondrial tRNA. In some embodiments, the at least one RNA derived from the gene comprises at least one rRNA. In some embodiments, the at least one RNA derived from the gene comprises at least one ribozyme. In some embodiments, the at least one RNA derived from the gene comprises at least one B-cell receptor subunit constant gene. In some embodiments, the at least one RNA derived from the gene comprises at least one T-cell receptor subunit constant gene.

The methods comprise screening the second transcriptome against the first transcriptome to generate a cat allergen exposure/treatment transcriptome. In some embodiments, screening the second transcriptome against the first transcriptome to generate the cat allergen exposure/treatment transcriptome comprises determining or having determined the differential gene expression in the second transcriptome with respect to the first transcriptome. The differential gene expression reveals the genes that have been downregulated upon treatment with at least one antibody to the cat allergen and genes that have been upregulated upon treatment with at least one antibody to the cat allergen. Downregulation and upregulation of genes can be determined by measuring the changes in expression of any of the RNA molecules described herein and/or the production of polypeptides. In some embodiments, the upregulation, downregulation, and differential gene expression is determined by a microarray or RNASeq. In some embodiments, the upregulation, downregulation, and differential gene expression is determined by a microarray. In some embodiments, the upregulation, downregulation, and differential gene expression is determined by RNASeq. In some embodiments, reverse transcription polymerase chain reaction (RT-PCR) can be used to measure gene expression.

In some embodiments, RNA sequencing reads can be mapped to a genome. In some embodiments, the genome is the human genome. In some embodiments, the human genome is reference assembly GRCh38. In some embodiments, the sequences can be mapped without strand specificity, with strand-specific reverse first-read mapping, or with strand-specific forward first-read mapping. In some embodiments, the sequences can be mapped using kallisto v0.45.0 with strand-specific reverse first-read mapping (Bray et al., Nat. Biotechnol., 2016, 34, 525). In some embodiments, transcript counts can be aggregated to gene counts. In some embodiments, the aggregation can be conducted using tximport (Soneson et al., F1000Research, 2015, 4, 1521).

In any of the methods described herein whereby a second transcriptome is screened against a first transcriptome to generate a cat allergen exposure/treatment transcriptome, particular thresholds can be used to determine whether a gene is considered to be upregulated or downregulated sufficiently in order to be included in the list of upregulated or downregulated genes described herein. For example, in some embodiments, the listed genes in the transcriptome identified from the screening can be selected to have a fold-change $\geq 2$, and a $q<0.05$ in at least one study. In some embodiments, the listed genes in the transcriptome identified from the screening can be selected to have a fold-change $\geq 1.5$, and a $q<0.05$ in at least one study. Alternately, a p value can be used instead of q value. In some embodiments, the listed genes in the transcriptome identified from the screening can be selected to have a $p<0.05$ in at least one study.

In some embodiments, the fold-change comprises subtracting the changes in expression in a placebo treatment group from the at least one antibody to a cat allergen treatment group.

In some embodiments, screening a second transcriptome against a first transcriptome to generate a cat allergen exposure/treatment transcriptome is carried out by comparing the baseline gene expression before exposure to cat allergen and treatment with at least one antibody to a cat allergen to the gene expression after exposure to a cat allergen and after treatment with at least one antibody to a cat allergen. In some embodiments, the second transcriptome is generated from a biological sample that is obtained about 2 hours after treatment with at least one antibody to a cat allergen. In some embodiments, the second transcriptome is generated from a biological sample that is obtained about 4 hours after treatment with at least one antibody to a cat allergen. In some embodiments, the second transcriptome is generated from a biological sample that is obtained about 6 hours after treatment with at least one antibody to a cat allergen. In some embodiments, the second transcriptome is generated from a biological sample that is obtained about 8 hours after treatment with at least one antibody to a cat allergen. In some embodiments, the second transcriptome is generated from a biological sample that is obtained about 12 hours after treatment with at least one antibody to a cat allergen. In some embodiments, the second transcriptome is generated from a biological sample that is obtained about 18 hours after treatment with at least one antibody to a cat allergen. In some embodiments, the second transcriptome is generated from a biological sample that is obtained about 24 hours after treatment with at least one antibody to a cat allergen. In some embodiments, the second transcriptome is generated from a biological sample that is obtained about 48 hours after treatment with at least one antibody to a cat allergen. In some embodiments, the second transcriptome is generated from a biological sample that is obtained about 72 hours after treatment with at least one antibody to a cat allergen. In some embodiments, the second transcriptome is generated from a biological sample that is obtained about 1 week after treatment with at least one antibody to a cat allergen. In some embodiments, the second transcriptome is generated from a biological sample that is obtained about 2 weeks after treatment with at least one antibody to a cat allergen. In some embodiments, the second transcriptome is generated from a biological sample that is obtained about 3 weeks after treatment with at least one antibody to a cat allergen. In some embodiments, the second transcriptome is generated from a biological sample that is obtained about 1 week after treatment to about one year after treatment with at least one antibody to a cat allergen. In some embodiments, the second transcriptome is generated from a biological sample that is obtained about 1 month after treatment with at least one antibody to a cat allergen. In some embodiments, the second transcriptome is generated from a biological sample that is obtained about 2 months after treatment with at least one antibody to a cat allergen. In some embodiments, the second transcriptome is generated from a biological sample that is obtained about 3 months after treatment with at least one antibody to a cat allergen. In some embodiments, the second transcriptome is generated from a biological sample that is obtained about 4 months after treatment with at least one antibody to a cat allergen. In some embodiments, the second transcriptome is generated from a biological sample that is obtained about 5 months after treatment with at least one antibody to a cat allergen. In some embodiments, the second transcriptome is generated from a biological sample that is obtained about 6 months after treatment with at least one antibody to a cat allergen.

In some embodiments, the screening of the second transcriptome against the first transcriptome comprises: i) transforming the first transcriptome into z-scores; ii) ranking the z-scores; and ii) generating a gene expression signature (GES) for all ranked z-scores using at least one gene which is differentially expressed and is in the first transcriptome, thereby representing at least one change in the second transcriptome with respect to the first transcriptome. In some embodiments, the GES is generated using a gene set enrichment analysis tool that takes both at least one positive gene set and at least one negative gene set into consideration. In some embodiments, the GES is generated by: a) transforming each gene expression within at least one gene into a z-score, and ordering at least one gene that is differentially expressed from the most upregulated to the most downregulated values to generate a value of R+; b) identifying hits independently for the most up-regulated gene set (S+) in R+, and the most downregulated gene set (S−) in R−, wherein R− is the inversed ranking of R+ with inverted values; c) combining R+ and R− and reordering the values by keeping the hits for both S+ and S−; d) computing a running score by walking down the combined ranking, wherein the running score increases by $/r_i/^p/\Sigma_{i\in S}/r/^p$ if the $i^{th}$ gene is a hit, or decreases by 1/(2N−S), where S is the combined total number of genes in S+ and S−; r; is the value for gene i, and p is the weight for r; e) determining an Enrichment Score (ES) as a maximum deviation from zero along the running score; f) repeating steps a)-e) with a random gene set for 1,000 times to compute the ES null distribution; and g) generating the NES as ES divided by the mean of ES null distribution. In some embodiments, the methods further comprise computing the statistical significance by determining the $95^{th}$ percentile GES from healthy control samples. In some embodiments, when the GES of the subject is higher than the GES of a healthy control, the subject is suitable for the antibody treatment.

In any of the methods described herein, the methods can further comprise obtaining or having obtained a first biological sample and/or a second biological sample from the subject for generating or having generated the first transcriptome and/or second transcriptome, respectively. In some embodiments, the end user of the methods described herein obtains the first biological sample and/or the second biological sample from the subject. In some embodiments, a third party obtains the first biological sample and/or the second biological sample from the subject, wherein the end user of the methods described herein receives the first biological sample and/or the second biological sample from the third party or the subject. In some embodiments, the first biological sample and/or second biological sample comprises a sample from an organ, a tissue, a cell, and/or a biological fluid. In some embodiments, the first biological sample and/or second biological sample comprises a sample from an organ. In some embodiments, the first biological sample and/or second biological sample comprises a sample from a tissue. In some embodiments, the first biological sample and/or second biological sample comprises a sample from a cell. In some embodiments, the first biological sample and/or second biological sample comprises a sample from a biological fluid. In some embodiments, the first biological sample and/or second biological sample comprises blood, semen, saliva, urine, feces, hair, teeth, bone, nasal mucosal tissue, bronchial alveolar lavage sample, respiratory tissue sample, and/or a buccal sample. In some embodiments, the first biological sample and/or second biological sample comprises blood. In some embodiments, the first biological sample and/or second biological sample comprises semen. In some embodiments, the first biological sample and/or second biological sample comprises saliva. In some embodiments, the first biological sample and/or second biological sample comprises urine. In some embodiments, the first biological sample and/or second biological sample comprises feces. In some embodiments, the first biological sample and/or second biological sample comprises hair. In some embodiments, the first biological sample and/or second biological sample comprises teeth. In some embodiments, the first biological sample and/or second biological sample comprises bone. In some embodiments, the first biological sample and/or second biological sample comprises nasal mucosal tissue. In some embodiments, the first biological sample and/or second biological sample comprises bronchial alveolar lavage sample. In some embodiments, the first biological sample and/or second biological sample comprises respiratory tissue sample. In some embodiments, the first biological sample and/or second biological sample comprises a buccal sample. In some embodiments, the first biological sample is obtained from the subject by a biopsy. In some embodiments, the first biological sample and/or second biological sample comprises plasma. In some embodiments, the first biological sample and/or second biological sample comprises serum. In some embodiments, the first biological sample and/or second biological sample comprises lymph. In some embodiments, the first biological sample and/or second biological sample comprises semen. In some embodiments, the first biological sample and/or second biological sample comprises a nasal mucosal secretion. In some embodiments, the biological sample is obtained from the nasal mucosa via a nasal brushing.

The present disclosure also provides methods of identifying a subject as suitable for the treatment or prevention of asthma exacerbation induced by a cat allergen with at least one antibody to the cat allergen. In some embodiments, the methods identify a subject that is suitable for the treatment of asthma exacerbation induced by a cat allergen with at least one antibody to the cat allergen. In some embodiments, the methods identify a subject that is suitable for the prevention of asthma exacerbation induced by a cat allergen with at least one antibody to the cat allergen. In some embodiments, the methods can be used to identifying a subject as suitable for the treatment or prevention of allergic rhinitis without asthma induced by a cat allergen with at least one antibody to the cat allergen. In some embodiments, the methods can be used to identifying a subject as suitable for the treatment or prevention of allergic asthma induced by a cat allergen with at least one antibody to the cat allergen. The methods comprise exposing the subject to at least one cat allergen. The methods also comprise generating or having generated a third transcriptome for the subject after exposure to at least one cat allergen. The methods also comprise treating the subject with at least one antibody to the cat allergen. The methods also comprise exposing the subject to at least one cat allergen. The methods also comprise generating or having generated a fourth transcriptome for the subject after exposing the subject to at least one cat allergen in step d). The methods also comprise screening the fourth transcriptome against the third transcriptome to generate a cat allergen exposure/treatment/exposure transcriptome.

The subject is suitable for the treatment or prevention of asthma exacerbation induced by a cat allergen with at least one antibody to the cat allergen when the cat allergen exposure/treatment/exposure transcriptome comprises: i) a downregulation of at least any ten of the following genes: LOC100132062, CCL8, AK128563, BC048201, LOC100133669, IL17D, RGS13, DKFZp434J0226, PMF1-BGLAP, LOC643802, AK123177, SPP1, BC041030, AK001975, THBS4, BC047364, CNGB3, FAM27C, SRMS, CXCL13, COL22A1, BC064137, AK055853, OCLM, PSORS1C2, AX746492, KCNA7, EFCAB3, NCAM1, PRR5-ARHGAP8, CNDP1, MSI1, BX648826, GFRA3, DACT1, AX748314, CNN1, BC107108, PCP2, LRRC63, SNAP25-AS1, ESYT3, HIST1H1D, AK129879, CASQ2, SLC16A10, CRISP3, KIAA0931, DQ588114, AX747628, AK022787, GFRA1, LIN7A, OXER1, LILRA5, AX748175, AK125412, LHFPL5, PTPLA, AX748417, AF119915, EMX2, PCDHGC4, SEPT12, BPIFB4, CILP, ADAMTS1, BHMT2, LINC00937, AX747864, TLDC2, BMP6, MMP9, MAP1LC3C, MSRB3, AK095583, LOC729444, DQ599872_2, MAGOH2, BC041484, TTYH1, PLA2G4E, PDE1B, CCR3, C22orf26, NAT2, AK125288, DPEP3, EDA2R, PYHIN1, CYSLTR2, GPR83, AX746564_2, SMIM1, AK311167, 7SK_25, LOC100288142, PAI1, ANKS4B, LMO3, AK097351, AK054921, PATE2, AK057519, KIAA0087, AK310030, CPXM2, RUNX1T1, LOC100506801, TMEM31, ZNF724P, AK311374, GNGT2, GRID1, PTCD1, AB209185, PPP1R27, FUT7, NXPH2, NECABI, BC039386, S100A5, SFTPD, KU-MEL-3, SALL1, BC070322, MYH6, AF086102, CLUL1, APOBEC2, RPL23P8, COL19A1, LRFN2, RAB3A, ANO3, RPS2P32, FOLR2, AK055332, FBN3, MYOZ3, NCRUPAR, AX748230, CCDC110, SLC13A1, LOC100270746, EPOR, TMEM252, LRFN1, CES1P2, MAL, ADH1A, ILDR2, CA10, SCHIP1, SND1-IT1, BC042024, NHSL2, KLRF2, PIEZO2, AL390170, BC021693, FAM198B, TIPARP-AS1, CD22, OLFM3, GNB3, BC042046, BC041007, DRD1, PGLYRP4, IGSF9B, KIF5A, FKSG63, AK123947, OR4F29, NKD2, PCDHA6, FOSL1, LAMB2P1, GBP1P1, AX746775, FRMD1, PCDHB9, AK301549, ALB, Metazoa_SRP_39, LOC100288911, ENTPD1-AS1, AX747405, FAM180A, MI0003602, ZNF891, SPATA31D5P, LSMEM1, PMS2L14, AK093534, TEX40, AK097590, SERPINB7, BC047540, KRT73, BC049825, TMPRSS6, TMEM200B, MAGEA2, BC047723, BMP2, HSD3B2, AIPL1, KCNA2, BC029473, SCN4A, CCDC116, GGN, KCNJ8, MI0000285, DDX4, LOC283177, MMP7, REM2, CYP17A1, NINJ2, LOC100506060, AX746750, ADAMTSL5, GPR143, WASH6P, CD2, SPDYE6, U4_5, and MKRN3; and an upregulation of at least any twenty of the following genes: ITGA9, RAB40AL, APLN, DCSTAMP, COL8A1, VRTN, SSMEM1, ALDH1L1-AS1, HNF1A, TOB2P1, INO80B, Metazoa_SRP_17, COL4A4, LINC00112, UGT2B28, VAX2, GAD1, CAPNS2, TUSC5, RBM46, LOC728739, LGSN, DQ574505, HYAL4, LOC100505474, TCRBV13S6A2T, C3orf70, UNC5D, TRAV20, CDKN3, ZNF774, RBM11, SHISA3, C9orf170, RBP5, NPAS1, CDY2A, STBD1, LOC441081, BC019672, CST9, P2RY4, CNBD1, DL490887, PCDHGA10, ZNF382, LDLRAD2, SLAMF9, CCNA2, AWAT2, AB586698, SLC25A21-AS1, MT11P, OCA2, SFTA1P, AK057259, ATP1A10S, GCSAML-AS1, LOC100130557, NXNL2, HSF2BP, CYP4Z2P, FU41941, SNORA66, CD1A, AK301968, ROR2, LOC339290, ITIH1, AK300656, QRFPR, TCP11, SLC35F1, ASCL1, TCRBV9S1A1T, TRPM2, DCC, SIRPD, KRTAP5-2, LOC100133050, MB21D2, POLN, CARD9, ZNF556, LOC148709, MEP1A, STAU2-AS1, BSN, DQ658414, SLC2A14, SPESP1, BLOC1S5, F2RL3, AHSG, LOC100505841, IQGAP3, AK127124, FAM182B, BC030152, TEX21P, PABPC1P2, UMODL1, TCRBV3S1, FMO9P, BC033983, KRTAP5-10, RASAL2-AS1, AJ606331, SH2D6, DSG1, LEMD1, NKAIN2, CR933665, BX648502, LOC286297, LOC647859, BC053679, VWCE, JN120857, ALPPL2, ALX4, Metazoa_SRP_66, WEE2, SPARC, SPTB, SLC22A13, GPR37, POU6F2, F12, PDGFRA, TPPP2, RPL13AP20, KNCN, FU30838, AIFM3, BLOC1S1-RDH5, ZNF177, RAB9B, ZNF815P, TRAV12-1, LOC339047, BC070061, SLC2A5, BC046483, ATOH7, UTS2B, LOC100289388, MCF2L2, COL9A1, CXorf57, BC017910, SUMO1P3, MATN1-AS1, IGLL5, DQ577420, CCDC73, FAM95B1, LOC100289092, PNMA2, AK125437, SLC7A5P2, ZNF367, LOC100131060, C11orf53, MRVI1-AS1, RUSC1-AS1, LOC51326, DSCR9, TRGC2, NPSR1-AS1, ABCB4, AX746969, CRB2, ESM1, ADAMTS15, GPR25, CDH17, NIM1, FU38723, LOC100129138, LIN7B, SLC47A2, IL36G, GOLGA8T, WFDC1, FOXD2-AS1, OR7D2, GPR63, FOXD4L1, LOC100507537, BC036361, BC070106, BEND4, CYS1, FU23584, GRIP2, CKLF-CMTM1, SPINK6, SARDH, HS3ST3B1, LOC643723, DJ031142, SMAD5-S1, AJ420489, PDE2A, EIF5AL1, UCN, SNPH, ANO7, SPC25, AX747264, SNORA6, SEC14L4, HLA-DPB2, C2orf27A, AX747125, SSR4P1, TFAP2B, BC045163, KIF18B, LOC644145, RFPL1S, IL9R, SNORA52, DPRXP4, LOC285768, CHKB-AS1, BCL2L2-PABPN1, STXBP5L, AK309988, DLEU7, SLFNL1-AS1, GABRR1, C10orf55, LOC100131655, NR5A2, OLFM2, DL492607, ADAM12, TDRD9, FAM74A4, BC062769, SLC30A4, LOC339874, LOC100128531, AK097190, BC080653, PEG3, RBFADN, FAM64A, CR627206, ETV2, GPSM1, PKNOX2, AK309255, PI16, SLC4A10, TUBB4A, AKR1C4, C17orf67, AX746484, SLC7A9, LOC643355, LOC645166, SLC28A1, FAM225B, ZNF663, GLB1L3, AK055272, ASGR2, ZCCHC18, LINC00312, BMPER, SYT2, CAMK2A, GRK7, HEATR4, BC023651, AK095633, CSPG4, SNORA81, U1_10, BC065373, AK056432, BC040572, RAB40A, BC040208, HABP2, MGC16142, PEBP4, CCDC154, LOC440934, AK128837, BVES, IGSF1, AX746944, AB075492, MYH16, RFTN2, LOC100130015, TLE6, AX746627, MUC3B, CABC1, LOC285972, BC024248, COL5A3, NSFP1, ANKRD55, TRA@, PRSS30P, ZNF385D, AK098783, CORT, TLR9, KCND2, AK095546, FAM35BP, ATP5J2-PTCD1, RAD51L3-RFFL, and LOC727751.

In some embodiments, the subject is suitable for the treatment or prevention of asthma exacerbation induced by a cat allergen with at least one antibody to the cat allergen when the cat allergen exposure/treatment/exposure transcriptome comprises: i) a downregulation of at least any twenty of the following genes: LOC100132062, CCL8, AK128563, BC048201, LOC100133669, IL17D, RGS13, DKFZp434J0226, PMF1-BGLAP, LOC643802, AK123177, SPP1, BC041030, AK001975, THBS4, BC047364, CNGB3, FAM27C, SRMS, CXCL13, COL22A1, BC064137, AK055853, OCLM, PSORS1C2, AX746492, KCNA7, EFCAB3, NCAM1, PRR5-ARHGAP8, CNDP1, MSI1, BX648826, GFRA3, DACT1, AX748314, CNN1, BC107108, PCP2, LRRC63, SNAP25-AS1, ESYT3, HIST1H1D, AK129879, CASQ2, SLC16A10, CRISP3, KIAA0931, DQ588114, AX747628, AK022787, GFRA1, LIN7A, OXER1, LILRA5, AX748175, AK125412, LHFPL5, PTPLA, AX748417, AF119915, EMX2, PCDHGC4, SEPT12, BPIFB4, CILP, ADAMTS1, BHMT2, LINC00937, AX747864, TLDC2, BMP6, MMP9, MAP1LC3C, MSRB3, AK095583, LOC729444, DQ599872_2, MAGOH2, BC041484, TTYH1, PLA2G4E, PDE1B, CCR3, C22orf26, NAT2, AK125288, DPEP3, EDA2R, PYHIN1, CYSLTR2, GPR83, AX746564_2, SMIM1, AK311167, 7SK_25, LOC100288142, PAI1, ANKS4B, LMO3, AK097351, AK054921, PATE2, AK057519, KIAA0087, AK310030, CPXM2, RUNX1T1, LOC100506801, TMEM31, ZNF724P, AK311374, GNGT2, GRID1, PTCD1, AB209185, PPP1R27, FUT7, NXPH2, NECABI, BC039386, S100A5, SFTPD, KU-MEL-3, SALL1, BC070322, MYH6, AF086102, CLUL1, APOBEC2, RPL23P8, COL19A1, LRFN2, RAB3A, ANO3, RPS2P32, FOLR2, AK055332, FBN3, MYOZ3, NCRUPAR, AX748230, CCDC110, SLC13A1, LOC100270746, EPOR, TMEM252, LRFN1, CES1P2, MAL, ADH1A, ILDR2, CA10, SCHIP1, SND1-IT1, BC042024, NHSL2, KLRF2, PIEZO2, AL390170, BC021693, FAM198B, TIPARP-AS1, CD22, OLFM3, GNB3, BC042046, BC041007, DRD1, PGLYRP4, IGSF9B, KIF5A, FKSG63, AK123947, OR4F29, NKD2, PCDHA6, FOSL1, LAMB2P1, GBP1P1, AX746775, FRMD1, PCDHB9, AK301549, ALB, Metazoa_SRP_39, LOC100288911, ENTPD1-AS1, AX747405, FAM180A, MI0003602, ZNF891, SPATA31D5P, LSMEM1, PMS2L14, AK093534, TEX40, AK097590, SERPINB7, BC047540, KRT73, BC049825, TMPRSS6, TMEM200B, MAGEA2, BC047723, BMP2, HSD3B2, AIPL1, KCNA2, BC029473, SCN4A, CCDC116, GGN, KCNJ8, MI0000285, DDX4, LOC283177, MMP7, REM2, CYP17A1, NINJ2, LOC100506060, AX746750, ADAMTSL5, GPR143, WASH6P, CD2, SPDYE6, U4_5, and MKRN3; and an upregulation of at least any forty of the following genes: ITGA9, RAB40AL, APLN, DCSTAMP, COL8A1, VRTN, SSMEM1, ALDH1L1-AS1, HNF1A, TOB2P1, INO80B, Metazoa_SRP_17, COL4A4, LINC00112, UGT2B28, VAX2, GAD1, CAPNS2, TUSC5, RBM46, LOC728739, LGSN, DQ574505, HYAL4, LOC100505474, TCRBV13S6A2T, C3orf70, UNC5D, TRAV20, CDKN3, ZNF774, RBM11, SHISA3, C9orf170, RBP5, NPAS1, CDY2A, STBD1, LOC441081, BC019672, CST9, P2RY4, CNBD1, DL490887, PCDHGA10, ZNF382, LDLRAD2, SLAMF9, CCNA2, AWAT2, AB586698, SLC25A21-AS1, MT1IP, OCA2, SFTA1P, AK057259, ATP1A10S, GCSAML-AS1, LOC100130557, NXNL2, HSF2BP, CYP4Z2P, FU41941, SNORA66, CD1A, AK301968, ROR2, LOC339290, ITIH1, AK300656, QRFPR, TCP11, SLC35F1, ASCL1, TCRBV9S1A1T, TRPM2, DCC, SIRPD, KRTAP5-2, LOC100133050, MB21D2, POLN, CARD9, ZNF556, LOC148709, MEP1A, STAU2-AS1, BSN, DQ658414, SLC2A14, SPESP1, BLOC1S5, F2RL3, AHSG, LOC100505841, IQGAP3, AK127124, FAM182B, BC030152, TEX21P, PABPC1P2, UMODL1, TCRBV3S1, FMO9P, BC033983, KRTAP5-10, RASAL2-AS1, AJ606331, SH2D6, DSG1, LEMD1, NKAIN2, CR933665, BX648502, LOC286297, LOC647859, BC053679, VWCE, JN120857, ALPPL2, ALX4, Metazoa_SRP_66, WEE2, SPARC, SPTB, SLC22A13, GPR37, POU6F2, F12, PDGFRA, TPPP2, RPL13AP20, KNCN, FU30838, AIFM3, BLOC1S1-RDH5, ZNF177, RAB9B, ZNF815P, TRAV12-1, LOC339047, BC070061, SLC2A5, BC046483, ATOH7, UTS2B, LOC100289388, MCF2L2, COL9A1, CXorf57, BC017910, SUMO1P3, MATN1-AS1, IGLL5, DQ577420, CCDC73, FAM95B1, LOC100289092, PNMA2, AK125437, SLC7A5P2, ZNF367, LOC100131060, C11orf53, MRVI1-AS1, RUSC1-AS1, LOC51326, DSCR9, TRGC2, NPSR1-AS1, ABCB4, AX746969, CRB2, ESM1, ADAMTS15, GPR25, CDH17, NIM1, FU38723, LOC100129138, LIN7B, SLC47A2, IL36G, GOLGA8T, WFDC1, FOXD2-AS1, OR7D2, GPR63, FOXD4L1, LOC100507537, BC036361, BC070106, BEND4, CYS1, FU23584, GRIP2, CKLF-CMTM1, SPINK6, SARDH, HS3ST3B1, LOC643723, DJ031142, SMAD5-S1, AJ420489, PDE2A, EIF5AL1, UCN, SNPH, ANO7, SPC25, AX747264, SNORA6, SEC14L4, HLA-DPB2, C2orf27A, AX747125, SSR4P1, TFAP2B, BC045163, KIF18B, LOC644145, RFPL1S, IL9R, SNORA52, DPRXP4, LOC285768, CHKB-AS1, BCL2L2-PABPN1, STXBP5L, AK309988, DLEU7, SLFNL1-AS1, GABRR1, C10orf55, LOC100131655, NR5A2, OLFM2, DL492607, ADAM12, TDRD9, FAM74A4, BC062769, SLC30A4, LOC339874, LOC100128531, AK097190, BC080653, PEG3, RBFADN, FAM64A, CR627206, ETV2, GPSM1, PKNOX2, AK309255, PI16, SLC4A10, TUBB4A, AKR1C4, C17orf67, AX746484, SLC7A9, LOC643355, LOC645166, SLC28A1, FAM225B, ZNF663, GLB1L3, AK055272, ASGR2, ZCCHC18, LINC00312, BMPER, SYT2, CAMK2A, GRK7, HEATR4, BC023651, AK095633, CSPG4, SNORA81, U1_10, BC065373, AK056432, BC040572, RAB40A, BC040208, HABP2, MGC16142, PEBP4, CCDC154, LOC440934, AK128837, BVES, IGSF1, AX746944, AB075492, MYH16, RFTN2, LOC100130015, TLE6, AX746627, MUC3B, CABC1, LOC285972, BC024248, COL5A3, NSFP1, ANKRD55, TRA@, PRSS30P, ZNF385D, AK098783, CORT, TLR9, KCND2, AK095546, FAM35BP, ATP5J2-PTCD1, RAD51L3-RFFL, and LOC727751.

In some embodiments, the subject is suitable for the treatment or prevention of asthma exacerbation induced by a cat allergen with at least one antibody to the cat allergen when the cat allergen exposure/treatment/exposure transcriptome comprises: i) a downregulation of at least any thirty of the following genes: LOC100132062, CCL8, AK128563, BC048201, LOC100133669, IL17D, RGS13, DKFZp434J0226, PMF1-BGLAP, LOC643802, AK123177, SPP1, BC041030, AK001975, THBS4, BC047364, CNGB3, FAM27C, SRMS, CXCL13, COL22A1, BC064137, AK055853, OCLM, PSORS1C2, AX746492, KCNA7, EFCAB3, NCAM1, PRR5-ARHGAP8, CNDP1, MSI1, BX648826, GFRA3, DACT1, AX748314, CNN1, BC107108, PCP2, LRRC63, SNAP25-AS1, ESYT3, HIST1H1D, AK129879, CASQ2, SLC16A10, CRISP3, KIAA0931, DQ588114, AX747628, AK022787, GFRA1, LIN7A, OXER1, LILRA5, AX748175, AK125412, LHFPL5, PTPLA, AX748417, AF119915, EMX2, PCDHGC4, SEPT12, BPIFB4, CILP, ADAMTS1, BHMT2, LINC00937, AX747864, TLDC2, BMP6, MMP9, MAP1LC3C, MSRB3, AK095583, LOC729444, DQ599872_2, MAGOH2, BC041484, TTYH1, PLA2G4E, PDE1B, CCR3, C22orf26, NAT2, AK125288, DPEP3, EDA2R, PYHIN1, CYSLTR2, GPR83, AX746564_2, SMIM1, AK311167, 7SK_25, LOC100288142, PAI1, ANKS4B, LMO3, AK097351, AK054921, PATE2, AK057519, KIAA0087, AK310030, CPXM2, RUNX1T1, LOC100506801, TMEM31, ZNF724P, AK311374, GNGT2, GRID1, PTCD1, AB209185, PPP1R27, FUT7, NXPH2, NECABI, BC039386, S100A5, SFTPD, KU-MEL-3, SALL1, BC070322, MYH6, AF086102, CLUL1, APOBEC2, RPL23P8, COL19A1, LRFN2, RAB3A, ANO3, RPS2P32, FOLR2, AK055332, FBN3, MYOZ3, NCRUPAR, AX748230, CCDC110, SLC13A1, LOC100270746, EPOR, TMEM252, LRFN1, CES1P2, MAL, ADH1A, ILDR2, CA10, SCHIP1, SND1-IT1, BC042024, NHSL2, KLRF2, PIEZO2, AL390170, BC021693, FAM198B, TIPARP-AS1, CD22, OLFM3, GNB3, BC042046, BC041007, DRD1, PGLYRP4, IGSF9B, KIF5A, FKSG63, AK123947, OR4F29, NKD2, PCDHA6, FOSL1, LAMB2P1, GBP1P1, AX746775, FRMD1, PCDHB9, AK301549, ALB, Metazoa_SRP_39, LOC100288911, ENTPD1-AS1, AX747405, FAM180A, MI0003602, ZNF891, SPATA31D5P, LSMEM1, PMS2L14, AK093534, TEX40, AK097590, SERPINB7, BC047540, KRT73, BC049825, TMPRSS6, TMEM200B, MAGEA2, BC047723, BMP2, HSD3B2, AIPL1, KCNA2, BC029473, SCN4A, CCDC116, GGN, KCNJ8, MI0000285, DDX4, LOC283177, MMP7, REM2, CYP17A1, NINJ2, LOC100506060, AX746750, ADAMTSL5, GPR143, WASH6P, CD2, SPDYE6, U4_5, and MKRN3; and an upregulation of at least any sixty of the following genes: ITGA9, RAB40AL, APLN, DCSTAMP, COL8A1, VRTN, SSMEM1, ALDH1L1-AS1, HNF1A, TOB2P1, INO80B, Metazoa_SRP_17, COL4A4, LINC00112, UGT2B28, VAX2, GAD1, CAPNS2, TUSC5, RBM46, LOC728739, LGSN, DQ574505, HYAL4, LOC100505474, TCRBV13S6A2T, C3orf70, UNC5D, TRAV20, CDKN3, ZNF774, RBM11, SHISA3, C9orf170, RBP5, NPAS1, CDY2A, STBD1, LOC441081, BC019672, CST9, P2RY4, CNBD1, DL490887, PCDHGA10, ZNF382, LDLRAD2, SLAMF9, CCNA2, AWAT2, AB586698, SLC25A21-AS1, MT1IP, OCA2, SFTA1P, AK057259, ATP1A10S, GCSAML-AS1, LOC100130557, NXNL2, HSF2BP, CYP4Z2P, FU41941, SNORA66, CD1A, AK301968, ROR2, LOC339290, ITIH1, AK300656, QRFPR, TCP11, SLC35F1, ASCL1, TCRBV9S1A1T, TRPM2, DCC, SIRPD, KRTAP5-2, LOC100133050, MB21D2, POLN, CARD9, ZNF556, LOC148709, MEP1A, STAU2-AS1, BSN, DQ658414, SLC2A14, SPESP1, BLOC1S5, F2RL3, AHSG, LOC100505841, IQGAP3, AK127124, FAM182B, BC030152, TEX21P, PABPC1P2, UMODL1, TCRBV3S1, FMO9P, BC033983, KRTAP5-10, RASAL2-AS1, AJ606331, SH2D6, DSG1, LEMD1, NKAIN2, CR933665, BX648502, LOC286297, LOC647859, BC053679, VWCE, JN120857, ALPPL2, ALX4, Metazoa_SRP_66, WEE2, SPARC, SPTB, SLC22A13, GPR37, POU6F2, F12, PDGFRA, TPPP2, RPL13AP20, KNCN, FU30838, AIFM3, BLOC1S1-RDH5, ZNF177, RAB9B, ZNF815P, TRAV12-1, LOC339047, BC070061, SLC2A5, BC046483, ATOH7, UTS2B, LOC100289388, MCF2L2, COL9A1, CXorf57, BC017910, SUMO1P3, MATN1-AS1, IGLL5, DQ577420, CCDC73, FAM95B1, LOC100289092, PNMA2, AK125437, SLC7A5P2, ZNF367, LOC100131060, C11orf53, MRVI1-AS1, RUSC1-AS1, LOC51326, DSCR9, TRGC2, NPSR1-AS1, ABCB4, AX746969, CRB2, ESM1, ADAMTS15, GPR25, CDH17, NIM1, FU38723, LOC100129138, LIN7B, SLC47A2, IL36G, GOLGA8T, WFDC1, FOXD2-AS1, OR7D2, GPR63, FOXD4L1, LOC100507537, BC036361, BC070106, BEND4, CYS1, FU23584, GRIP2, CKLF-CMTM1, SPINK6, SARDH, HS3ST3B1, LOC643723, DJ031142, SMAD5-S1, AJ420489, PDE2A, EIF5AL1, UCN, SNPH, ANO7, SPC25, AX747264, SNORA6, SEC14L4, HLA-DPB2, C2orf27A, AX747125, SSR4P1, TFAP2B, BC045163, KIF18B, LOC644145, RFPL1S, IL9R, SNORA52, DPRXP4, LOC285768, CHKB-AS1, BCL2L2-PABPN1, STXBP5L, AK309988, DLEU7, SLFNL1-AS1, GABRR1, C10orf55, LOC100131655, NR5A2, OLFM2, DL492607, ADAM12, TDRD9, FAM74A4, BC062769, SLC30A4, LOC339874, LOC100128531, AK097190, BC080653, PEG3, RBFADN, FAM64A, CR627206, ETV2, GPSM1, PKNOX2, AK309255, PI16, SLC4A10, TUBB4A, AKR1C4, C17orf67, AX746484, SLC7A9, LOC643355, LOC645166, SLC28A1, FAM225B, ZNF663, GLB1L3, AK055272, ASGR2, ZCCHC18, LINC00312, BMPER, SYT2, CAMK2A, GRK7, HEATR4, BC023651, AK095633, CSPG4, SNORA81, U1_10, BC065373, AK056432, BC040572, RAB40A, BC040208, HABP2, MGC16142, PEBP4, CCDC154, LOC440934, AK128837, BVES, IGSF1, AX746944, AB075492, MYH16, RFTN2, LOC100130015, TLE6, AX746627, MUC3B, CABC1, LOC285972, BC024248, COL5A3, NSFP1, ANKRD55, TRA@, PRSS30P, ZNF385D, AK098783, CORT, TLR9, KCND2, AK095546, FAM35BP, ATP5J2-PTCD1, RAD51L3-RFFL, and LOC727751.

In some embodiments, the subject is suitable for the treatment or prevention of asthma exacerbation induced by a cat allergen with at least one antibody to the cat allergen when the cat allergen exposure/treatment/exposure transcriptome comprises: i) a downregulation of at least any forty of the following genes: LOC100132062, CCL8, AK128563, BC048201, LOC100133669, IL17D, RGS13, DKFZp434J0226, PMF1-BGLAP, LOC643802, AK123177, SPP1, BC041030, AK001975, THBS4, BC047364, CNGB3, FAM27C, SRMS, CXCL13, COL22A1, BC064137, AK055853, OCLM, PSORS1C2, AX746492, KCNA7, EFCAB3, NCAM1, PRR5-ARHGAP8, CNDP1, MSI1, BX648826, GFRA3, DACT1, AX748314, CNN1, BC107108, PCP2, LRRC63, SNAP25-AS1, ESYT3, HIST1H1D, AK129879, CASQ2, SLC16A10, CRISP3, KIAA0931, DQ588114, AX747628, AK022787, GFRA1, LIN7A, OXER1, LILRA5, AX748175, AK125412, LHFPL5, PTPLA, AX748417, AF119915, EMX2, PCDHGC4, SEPT12, BPIFB4, CILP, ADAMTS1, BHMT2, LINC00937, AX747864, TLDC2, BMP6, MMP9, MAP1LC3C, MSRB3, AK095583, LOC729444, DQ599872_2, MAGOH2, BC041484, TTYH1, PLA2G4E, PDE1B, CCR3, C22orf26, NAT2, AK125288, DPEP3, EDA2R, PYHIN1, CYSLTR2, GPR83, AX746564_2, SMIM1, AK311167, 7SK_25, LOC100288142, PAI1, ANKS4B, LMO3, AK097351, AK054921, PATE2, AK057519, KIAA0087, AK310030, CPXM2, RUNX1T1, LOC100506801, TMEM31, ZNF724P, AK311374, GNGT2, GRID1, PTCD1, AB209185, PPP1R27, FUT7, NXPH2, NECABI, BC039386, S100A5, SFTPD, KU-MEL-3, SALL1, BC070322, MYH6, AF086102, CLUL1, APOBEC2, RPL23P8, COL19A1, LRFN2, RAB3A, ANO3, RPS2P32, FOLR2, AK055332, FBN3, MYOZ3, NCRUPAR, AX748230, CCDC110, SLC13A1, LOC100270746, EPOR, TMEM252, LRFN1, CES1P2, MAL, ADH1A, ILDR2, CA10, SCHIP1, SND1-IT1, BC042024, NHSL2, KLRF2, PIEZO2, AL390170, BC021693, FAM198B, TIPARP-AS1, CD22, OLFM3, GNB3, BC042046, BC041007, DRD1, PGLYRP4, IGSF9B, KIF5A, FKSG63, AK123947, OR4F29, NKD2, PCDHA6, FOSL1, LAMB2P1, GBP1P1, AX746775, FRMD1, PCDHB9, AK301549, ALB, Metazoa_SRP_39, LOC100288911, ENTPD1-AS1, AX747405, FAM180A, MI0003602, ZNF891, SPATA31D5P, LSMEM1, PMS2L14, AK093534, TEX40, AK097590, SERPINB7, BC047540, KRT73, BC049825, TMPRSS6, TMEM200B, MAGEA2, BC047723, BMP2, HSD3B2, AIPL1, KCNA2, BC029473, SCN4A, CCDC116, GGN, KCNJ8, MI0000285, DDX4, LOC283177, MMP7, REM2, CYP17A1, NINJ2, LOC100506060, AX746750, ADAMTSL5, GPR143, WASH6P, CD2, SPDYE6, U4_5, and MKRN3; and an upregulation of at least any eighty of the following genes: ITGA9, RAB40AL, APLN, DCSTAMP, COL8A1, VRTN, SSMEM1, ALDH1L1-AS1, HNF1A, TOB2P1, INO80B, Metazoa_SRP_17, COL4A4, LINC00112, UGT2B28, VAX2, GAD1, CAPNS2, TUSC5, RBM46, LOC728739, LGSN, DQ574505, HYAL4, LOC100505474, TCRBV13S6A2T, C3orf70, UNC5D, TRAV20, CDKN3, ZNF774, RBM11, SHISA3, C9orf170, RBP5, NPAS1, CDY2A, STBD1, LOC441081, BC019672, CST9, P2RY4, CNBD1, DL490887, PCDHGA10, ZNF382, LDLRAD2, SLAMF9, CCNA2, AWAT2, AB586698, SLC25A21-AS1, MT1IP, OCA2, SFTA1P, AK057259, ATP1A10S, GCSAML-AS1, LOC100130557, NXNL2, HSF2BP, CYP4Z2P, FU41941, SNORA66, CD1A, AK301968, ROR2, LOC339290, ITIH1, AK300656, QRFPR, TCP11, SLC35F1, ASCL1, TCRBV9S1A1T, TRPM2, DCC, SIRPD, KRTAP5-2, LOC100133050, MB21D2, POLN, CARD9, ZNF556, LOC148709, MEP1A, STAU2-AS1, BSN, DQ658414, SLC2A14, SPESP1, BLOC1S5, F2RL3, AHSG, LOC100505841, IQGAP3, AK127124, FAM182B, BC030152, TEX21P, PABPC1P2, UMODL1, TCRBV3S1, FMO9P, BC033983, KRTAP5-10, RASAL2-AS1, AJ606331, SH2D6, DSG1, LEMD1, NKAIN2, CR933665, BX648502, LOC286297, LOC647859, BC053679, VWCE, JN120857, ALPPL2, ALX4, Metazoa_SRP_66, WEE2, SPARC, SPTB, SLC22A13, GPR37, POU6F2, F12, PDGFRA, TPPP2, RPL13AP20, KNCN, FU30838, AIFM3, BLOC1S1-RDH5, ZNF177, RAB9B, ZNF815P, TRAV12-1, LOC339047, BC070061, SLC2A5, BC046483, ATOH7, UTS2B, LOC100289388, MCF2L2, COL9A1, CXorf57, BC017910, SUMO1P3, MATN1-AS1, IGLL5, DQ577420, CCDC73, FAM95B1, LOC100289092, PNMA2, AK125437, SLC7A5P2, ZNF367, LOC100131060, C11orf53, MRVI1-AS1, RUSC1-AS1, LOC51326, DSCR9, TRGC2, NPSR1-AS1, ABCB4, AX746969, CRB2, ESM1, ADAMTS15, GPR25, CDH17, NIM1, FU38723, LOC100129138, LIN7B, SLC47A2, IL36G, GOLGA8T, WFDC1, FOXD2-AS1, OR7D2, GPR63, FOXD4L1, LOC100507537, BC036361, BC070106, BEND4, CYS1, FU23584, GRIP2, CKLF-CMTM1, SPINK6, SARDH, HS3ST3B1, LOC643723, DJ031142, SMAD5-S1, AJ420489, PDE2A, EIF5AL1, UCN, SNPH, ANO7, SPC25, AX747264, SNORA6, SEC14L4, HLA-DPB2, C2orf27A, AX747125, SSR4P1, TFAP2B, BC045163, KIF18B, LOC644145, RFPL1S, IL9R, SNORA52, DPRXP4, LOC285768, CHKB-AS1, BCL2L2-PABPN1, STXBP5L, AK309988, DLEU7, SLFNL1-AS1, GABRR1, C10orf55, LOC100131655, NR5A2, OLFM2, DL492607, ADAM12, TDRD9, FAM74A4, BC062769, SLC30A4, LOC339874, LOC100128531, AK097190, BC080653, PEG3, RBFADN, FAM64A, CR627206, ETV2, GPSM1, PKNOX2, AK309255, PI16, SLC4A10, TUBB4A, AKR1C4, C17orf67, AX746484, SLC7A9, LOC643355, LOC645166, SLC28A1, FAM225B, ZNF663, GLB1L3, AK055272, ASGR2, ZCCHC18, LINC00312, BMPER, SYT2, CAMK2A, GRK7, HEATR4, BC023651, AK095633, CSPG4, SNORA81, U1_10, BC065373, AK056432, BC040572, RAB40A, BC040208, HABP2, MGC16142, PEBP4, CCDC154, LOC440934, AK128837, BVES, IGSF1, AX746944, AB075492, MYH16, RFTN2, LOC100130015, TLE6, AX746627, MUC3B, CABC1, LOC285972, BC024248, COL5A3, NSFP1, ANKRD55, TRA@, PRSS30P, ZNF385D, AK098783, CORT, TLR9, KCND2, AK095546, FAM35BP, ATP5J2-PTCD1, RAD51L3-RFFL, and LOC727751.

In some embodiments, the subject is suitable for the treatment or prevention of asthma exacerbation induced by a cat allergen with at least one antibody to the cat allergen when the cat allergen exposure/treatment/exposure transcriptome comprises: i) a downregulation of all of the following genes: LOC100132062, CCL8, AK128563, BC048201, LOC100133669, IL17D, RGS13, DKFZp434J0226, PMF1-BGLAP, LOC643802, AK123177, SPP1, BC041030, AK001975, THBS4, BC047364, CNGB3, FAM27C, SRMS, CXCL13, COL22A1, BC064137, AK055853, OCLM, PSORS1C2, AX746492, KCNA7, EFCAB3, NCAM1, PRR5-ARHGAP8, CNDP1, MSI1, BX648826, GFRA3, DACT1, AX748314, CNN1, BC107108, PCP2, LRRC63, SNAP25-AS1, ESYT3, HIST1H1D, AK129879, CASQ2, SLC16A10, CRISP3, KIAA0931, DQ588114, AX747628, AK022787, GFRA1, LIN7A, OXER1, LILRA5, AX748175, AK125412, LHFPL5, PTPLA, AX748417, AF119915, EMX2, PCDHGC4, SEPT12, BPIFB4, CILP, ADAMTS1, BHMT2, LINC00937, AX747864, TLDC2, BMP6, MMP9, MAP1LC3C, MSRB3, AK095583, LOC729444, DQ599872_2, MAGOH2, BC041484, TTYH1, PLA2G4E, PDE1B, CCR3, C22orf26, NAT2, AK125288, DPEP3, EDA2R, PYHIN1, CYSLTR2, GPR83, AX746564_2, SMIM1, AK311167, 7SK_25, LOC100288142, PAI1, ANKS4B, LMO3, AK097351, AK054921, PATE2, AK057519, KIAA0087, AK310030, CPXM2, RUNX1T1, LOC100506801, TMEM31, ZNF724P, AK311374, GNGT2, GRID1, PTCD1, AB209185, PPP1R27, FUT7, NXPH2, NECABI, BC039386, S100A5, SFTPD, KU-MEL-3, SALL1, BC070322, MYH6, AF086102, CLUL1, APOBEC2, RPL23P8, COL19A1, LRFN2, RAB3A, ANO3, RPS2P32, FOLR2, AK055332, FBN3, MYOZ3, NCRUPAR, AX748230, CCDC110, SLC13A1, LOC100270746, EPOR, TMEM252, LRFN1, CES1P2, MAL, ADH1A, ILDR2, CA10, SCHIP1, SND1-IT1, BC042024, NHSL2, KLRF2, PIEZO2, AL390170, BC021693, FAM198B, TIPARP-AS1, CD22, OLFM3, GNB3, BC042046, BC041007, DRD1, PGLYRP4, IGSF9B, KIF5A, FKSG63, AK123947, OR4F29, NKD2, PCDHA6, FOSL1, LAMB2P1, GBP1P1, AX746775, FRMD1, PCDHB9, AK301549, ALB, Metazoa_SRP_39, LOC100288911, ENTPD1-AS1, AX747405, FAM180A, MI0003602, ZNF891, SPATA31D5P, LSMEM1, PMS2L14, AK093534, TEX40, AK097590, SERPINB7, BC047540, KRT73, BC049825, TMPRSS6, TMEM200B, MAGEA2, BC047723, BMP2, HSD3B2, AIPL1, KCNA2, BC029473, SCN4A, CCDC116, GGN, KCNJ8, MI0000285, DDX4, LOC283177, MMP7, REM2, CYP17A1, NINJ2, LOC100506060, AX746750, ADAMTSL5, GPR143, WASH6P, CD2, SPDYE6, U4_5, and MKRN3; and an upregulation of all of the following genes: ITGA9, RAB40AL, APLN, DCSTAMP, COL8A1, VRTN, SSMEM1, ALDH1L1-AS1, HNF1A, TOB2P1, INO80B, Metazoa_SRP_17, COL4A4, LINC00112, UGT2B28, VAX2, GAD1, CAPNS2, TUSC5, RBM46, LOC728739, LGSN, DQ574505, HYAL4, LOC100505474, TCRBV13S6A2T, C3orf70, UNC5D, TRAV20, CDKN3, ZNF774, RBM11, SHISA3, C9orf170, RBP5, NPAS1, CDY2A, STBD1, LOC441081, BC019672, CST9, P2RY4, CNBD1, DL490887, PCDHGA10, ZNF382, LDLRAD2, SLAMF9, CCNA2, AWAT2, AB586698, SLC25A21-AS1, MT1IP, OCA2, SFTA1P, AK057259, ATP1A10S, GCSAML-AS1, LOC100130557, NXNL2, HSF2BP, CYP4Z2P, FU41941, SNORA66, CD1A, AK301968, ROR2, LOC339290, ITIH1, AK300656, QRFPR, TCP11, SLC35F1, ASCL1, TCRBV9S1A1T, TRPM2, DCC, SIRPD, KRTAP5-2, LOC100133050, MB21D2, POLN, CARD9, ZNF556, LOC148709, MEP1A, STAU2-AS1, BSN, DQ658414, SLC2A14, SPESP1, BLOC1S5, F2RL3, AHSG, LOC100505841, IQGAP3, AK127124, FAM182B, BC030152, TEX21P, PABPC1P2, UMODL1, TCRBV3S1, FMO9P, BC033983, KRTAP5-10, RASAL2-AS1, AJ606331, SH2D6, DSG1, LEMD1, NKAIN2, CR933665, BX648502, LOC286297, LOC647859, BC053679, VWCE, JN120857, ALPPL2, ALX4, Metazoa_SRP_66, WEE2, SPARC, SPTB, SLC22A13, GPR37, POU6F2, F12, PDGFRA, TPPP2, RPL13AP20, KNCN, FU30838, AIFM3, BLOC1S1-RDH5, ZNF177, RAB9B, ZNF815P, TRAV12-1, LOC339047, BC070061, SLC2A5, BC046483, ATOH7, UTS2B, LOC100289388, MCF2L2, COL9A1, CXorf57, BC017910, SUMO1P3, MATN1-AS1, IGLL5, DQ577420, CCDC73, FAM95B1, LOC100289092, PNMA2, AK125437, SLC7A5P2, ZNF367, LOC100131060, C11orf53, MRVI1-AS1, RUSC1-AS1, LOC51326, DSCR9, TRGC2, NPSR1-AS1, ABCB4, AX746969, CRB2, ESM1, ADAMTS15, GPR25, CDH17, NIM1, FU38723, LOC100129138, LIN7B, SLC47A2, IL36G, GOLGA8T, WFDC1, FOXD2-AS1, OR7D2, GPR63, FOXD4L1, LOC100507537, BC036361, BC070106, BEND4, CYS1, FU23584, GRIP2, CKLF-CMTM1, SPINK6, SARDH, HS3ST3B1, LOC643723, DJ031142, SMAD5-S1, AJ420489, PDE2A, EIF5AL1, UCN, SNPH, ANO7, SPC25, AX747264, SNORA6, SEC14L4, HLA-DPB2, C2orf27A, AX747125, SSR4P1, TFAP2B, BC045163, KIF18B, LOC644145, RFPL1S, IL9R, SNORA52, DPRXP4, LOC285768, CHKB-AS1, BCL2L2-PABPN1, STXBP5L, AK309988, DLEU7, SLFNL1-AS1, GABRR1, C10orf55, LOC100131655, NR5A2, OLFM2, DL492607, ADAM12, TDRD9, FAM74A4, BC062769, SLC30A4, LOC339874, LOC100128531, AK097190, BC080653, PEG3, RBFADN, FAM64A, CR627206, ETV2, GPSM1, PKNOX2, AK309255, PI16, SLC4A10, TUBB4A, AKR1C4, C17orf67, AX746484, SLC7A9, LOC643355, LOC645166, SLC28A1, FAM225B, ZNF663, GLB1L3, AK055272, ASGR2, ZCCHC18, LINC00312, BMPER, SYT2, CAMK2A, GRK7, HEATR4, BC023651, AK095633, CSPG4, SNORA81, U1_10, BC065373, AK056432, BC040572, RAB40A, BC040208, HABP2, MGC16142, PEBP4, CCDC154, LOC440934, AK128837, BVES, IGSF1, AX746944, AB075492, MYH16, RFTN2, LOC100130015, TLE6, AX746627, MUC3B, CABC1, LOC285972, BC024248, COL5A3, NSFP1, ANKRD55, TRA@, PRSS30P, ZNF385D, AK098783, CORT, TLR9, KCND2, AK095546, FAM35BP, ATP5J2-PTCD1, RAD51L3-RFFL, and LOC727751.

In some embodiments, any 1, any 2, any 3, any 4, any 5, any 6, any 7, any 8, any 9, or any 10 of the downregulated genes described herein can be omitted from the gene expression analysis. In some embodiments, any 1, any 2, any 3, any 4, any 5, any 6, any 7, any 8, any 9, any 10, any 11, any 12, any 13, any 14, any 15, any 16, any 17, any 18, any 19, or any 20 of the upregulated genes described herein can be omitted from the gene expression analysis. The genes that can be monitored for upregulation or downregulation include, but are not limited to any one or more, or any combination thereof, of the genes listed in Table 4.

In some embodiments, the subject has been previously determined to have a cat allergen exposure/treatment/exposure transcriptome. In some embodiments, the cat allergen exposure/treatment/exposure transcriptome comprises: a downregulation of at least any ten of the set of genes described herein, and an upregulation of at least any twenty of the set of genes described herein.

In some embodiments, the subject was previously removed from exposure to at least one cat in an NEC in less than two hours. In some embodiments, the subject comprises any of the cat allergen exposure/treatment/exposure transcriptome described herein.

The methods comprise exposing the subject to at least one cat allergen. In some embodiments, exposing the subject to at least one cat allergen comprises exposing the subject to at least one cat for at least 30 minutes, at least 1 hour, at least 2 hours, at least 3 hours, at least 4 hours, at least 5 hours, or at least 6 hours. In some embodiments, exposing the subject to at least one cat allergen comprises exposing the subject to at least one cat for at least 30 minutes. In some embodiments, exposing the subject to at least one cat allergen comprises exposing the subject to at least one cat for at least 1 hour. In some embodiments, exposing the subject to at least one cat allergen comprises exposing the subject to at least one cat for at least 2 hours. In some embodiments, exposing the subject to at least one cat allergen comprises exposing the subject to at least one cat for at least 3 hours. In some embodiments, exposing the subject to at least one cat allergen comprises exposing the subject to at least one cat for at least 4 hours. In some embodiments, exposing the subject to at least one cat allergen comprises exposing the subject to at least one cat for at least 5 hours. In some embodiments, exposing the subject to at least one cat allergen comprises exposing the subject to at least one cat for at least 6 hours. In some embodiments, exposing the subject to at least one cat occurs in an NEC or an EEU. In some embodiments, exposing the subject to at least one cat occurs in an NEC. In some embodiments, exposing the subject to at least one cat occurs in an EEU. In some embodiments, the subject is exposed to at least one cat in the NEC or EEU for no longer than two hours.

In some embodiments, exposing the subject to at least one cat allergen comprises exposing the subject to cat dander or at least one cat allergen for at least 30 minutes, at least 1 hour, at least 2 hours, at least 3 hours, at least 4 hours, at least 5 hours, or at least 6 hours. In some embodiments, exposing the subject to at least one cat allergen comprises exposing the subject to cat dander or at least one cat allergen for at least 30 minutes. In some embodiments, exposing the subject to at least one cat allergen comprises exposing the subject to cat dander or at least one cat allergen for at least 1 hour. In some embodiments, exposing the subject to at least one cat allergen comprises exposing the subject to cat dander or at least one cat allergen for at least 2 hours. In some embodiments, exposing the subject to at least one cat allergen comprises exposing the subject to cat dander or at least one cat allergen for at least 3 hours. In some embodiments, exposing the subject to at least one cat allergen comprises exposing the subject to cat dander or at least one cat allergen at least 4 hours. In some embodiments, exposing the subject to at least one cat allergen comprises exposing the subject to cat dander or at least one cat allergen for at least 5 hours. In some embodiments, exposing the subject to at least one cat allergen comprises exposing the subject to cat dander or at least one cat allergen for at least 6 hours. In some embodiments, exposing the subject to at least one cat allergen comprises administering or having administered to the subject cat dander or the at least one cat allergen to the skin of the subject or to the nasal mucosa of the subject. In some embodiments, exposing the subject to at least one cat allergen comprises administering or having administered to the subject cat dander or the at least one cat allergen to the skin of the subject. In some embodiments, exposing the subject to at least one cat allergen comprises administering or having administered to the subject cat dander or the at least one cat allergen to the nasal mucosa of the subject.

In some embodiments, the cat dander comprises Fel d 1, Fel d 2, Fel d 3, Fel d 4, Fel d 5, Fel d 6, Fel d 7, or Fel d 8, or any combination thereof. In some embodiments, the at least one cat allergen comprises Fel d 1, Fel d 2, Fel d 3, Fel d 4, Fel d 5, Fel d 6, Fel d 7, or Fel d 8, or any combination thereof. In some embodiments, the at least one cat allergen comprises Fel d 1. In some embodiments, the at least one cat allergen comprises Fel d 2. In some embodiments, the at least one cat allergen comprises Fel d 3. In some embodiments, the at least one cat allergen comprises Fel d 4. In some embodiments, the at least one cat allergen comprises Fel d 5. In some embodiments, the at least one cat allergen comprises Fel d 6. In some embodiments, the at least one cat allergen comprises Fel d 7. In some embodiments, the at least one cat allergen comprises Fel d 8. In some embodiments, from about 10 ng/m$^3$ to about 70 ng/m$^3$ of standardized cat allergen extract can be continuously nebulized into an EEU. In some embodiments, from about 20 ng/m$^3$ to about 60 ng/m$^3$ of standardized cat allergen extract can be continuously nebulized into an EEU. In some embodiments, from about 30 ng/m$^3$ to about 50 ng/m$^3$ of standardized cat allergen extract can be continuously nebulized into an EEU. In some embodiments, about 40 ng/m$^3$ of standardized cat allergen extract can be continuously nebulized into an EEU.

The methods comprise generating or having generated a third transcriptome for the subject after exposure to the at least one cat allergen (and prior to treatment with at least one antibody to a cat allergen). In some embodiments, the end user of the methods described herein generates the third transcriptome for the subject. In some embodiments, a third party generates the third transcriptome for the subject, wherein the end user of the methods described herein receives the third transcriptome information from the third party or the subject. In some embodiments, generating or having generated a third transcriptome for the subject comprises a first quantification of expression of any combination of the downreglated and upregulated genes described herein. In some embodiments, generating or having generated a third transcriptome for the subject comprises a first quantification of expression of at least one RNA derived from the gene. In some embodiments, the at least one RNA derived from the gene comprises at least one messenger RNA, at least one long non-coding RNA, at least one mitochondrial rRNA, at least one mitochondrial tRNA, at least one rRNA, at least one ribozyme, at least one B-cell receptor subunit constant gene, and/or at least one T-cell receptor subunit constant gene. In some embodiments, the at least one RNA derived from the gene comprises at least one messenger RNA. In some embodiments, the at least one RNA derived from the gene comprises at least one long non-coding RNA. In some embodiments, the at least one RNA derived from the gene comprises at least one mitochondrial rRNA. In some embodiments, the at least one RNA derived from the gene comprises at least one mitochondrial tRNA. In some embodiments, the at least one RNA derived from the gene comprises at least one rRNA. In some embodiments, the at least one RNA derived from the gene comprises at least one ribozyme. In some embodiments, the at least one RNA derived from the gene comprises at least one B-cell receptor subunit constant gene. In some embodiments, the at least one RNA derived from the gene comprises at least one T-cell receptor subunit constant gene.

The methods comprise treating the subject with at least one antibody to the cat allergen. In some embodiments, the at least one antibody to the cat allergen comprises at least one antibody to Fel d 1. In some embodiments, the at least one antibody to the cat allergen comprises two monoclonal antibodies to Fel d 1. In some embodiments, the two monoclonal antibodies to Fel d 1 are fully human monoclonal antibodies. In some embodiments, the two fully human monoclonal antibodies to Fel d 1 comprises REGN1908 and REGN1909. In some embodiments, from about 300 mg to about 900 mg of the REGN1908/1909 antibody cocktail can be administered to the subject. In some embodiments, from about 400 mg to about 800 mg of the REGN1908/1909 antibody cocktail can be administered to the subject. In some embodiments, from about 500 mg to about 700 mg of the REGN1908/1909 antibody cocktail can be administered to the subject. In some embodiments, about 600 mg of the REGN1908/1909 antibody cocktail can be administered to the subject. The ratio of REGN1908 to REGN1909 can be 1:1, 0.9:1.1, 0.8:1.2, 0.7:1.3, 0.6:1.4, 0.5:1.5, 1.1:0.9, 1.2:0.8, 1.3:0.7, 1.4:0.6, or 1.5:0.5. In some embodiments, the subject receiving about 600 mg of the REGN1908/1909 antibody cocktail receives 300 mg of each of REGN1908 and REGN1909. The at least one antibody to the cat allergen can be administered by any route of administration including, but not limited to, oral, sublingual, buccal, rectal, intranasal, inhalation, epicutaneous or transdermal, subcutaneous, intradermal, intravenous, intraarterial, intraosseous infusion, intramuscular, intracardiac, intraperitoneal, intravesical infusion, and intravitreal. In some embodiments, the administration is subcutaneous.

The methods comprise a second exposure to at least one cat allergen. The second exposure to the at least one cat allergen can comprise any of the methods described herein for exposure to a cat allergen.

The methods comprise generating or having generated a fourth transcriptome for the subject after cat allergen exposure, after treatment with at least one antibody to the cat allergen, and after a second cat allergen exposure. In some embodiments, the end user of the methods described herein generates the fourth transcriptome for the subject. In some embodiments, a third party generates the fourth transcriptome for the subject, wherein the end user of the methods described herein receives the fourth transcriptome information from the third party or the subject. In some embodiments, generating or having generated a fourth transcriptome for the subject comprises a second quantification of expression of any combination of the downreglated and upregulated genes described herein. In some embodiments, generating or having generated a fourth transcriptome for the subject comprises a second quantification of expression of at least one RNA derived from the gene. In some embodiments, the at least one RNA derived from the gene comprises at least one messenger RNA, at least one long non-coding RNA, at least one mitochondrial rRNA, at least one mitochondrial tRNA, at least one rRNA, at least one ribozyme, at least one B-cell receptor subunit constant gene, and/or at least one T-cell receptor subunit constant gene. In some embodiments, the at least one RNA derived from the gene comprises at least one messenger RNA. In some embodiments, the at least one RNA derived from the gene comprises at least one long non-coding RNA. In some embodiments, the at least one RNA derived from the gene comprises at least one mitochondrial rRNA. In some embodiments, the at least one RNA derived from the gene comprises at least one mitochondrial tRNA. In some embodiments, the at least one RNA derived from the gene comprises at least one rRNA. In some embodiments, the at least one RNA derived from the gene comprises at least one ribozyme. In some embodiments, the at least one RNA derived from the gene comprises at least one B-cell receptor subunit constant gene. In some embodiments, the at least one RNA derived from the gene comprises at least one T-cell receptor subunit constant gene.

The methods comprise screening the fourth transcriptome against the third transcriptome to generate a cat allergen exposure/treatment/exposure transcriptome. In some embodiments, screening the fourth transcriptome against the third transcriptome to generate the cat allergen exposure/treatment/exposure transcriptome comprises determining or having determined the differential gene expression in the fourth transcriptome with respect to the third transcriptome. The differential gene expression reveals the genes that have been downregulated upon treatment with at least one antibody to the cat allergen and genes that have been upregulated upon treatment with at least one antibody to the cat allergen. Downregulation and upregulation of genes can be determined by measuring the changes in expression of any of the RNA molecules described herein and/or the production of polypeptides. In some embodiments, the upregulation, downregulation, and differential gene expression is determined by a microarray or RNASeq. In some embodiments, the upregulation, downregulation, and differential gene expression is determined by a microarray. In some embodiments, the upregulation, downregulation, and differential gene expression is determined by RNASeq. In some embodiments, reverse transcription polymerase chain reaction (RT-PCR) can be used to measure gene expression.

In some embodiments, RNA sequencing reads can be mapped to a genome. In some embodiments, the genome is the human genome. In some embodiments, the human genome is reference assembly GRCh38. In some embodiments, the sequences can be mapped without strand specificity, with strand-specific reverse first-read mapping, or with strand-specific forward first-read mapping. In some embodiments, the sequences can be mapped using kallisto v0.45.0 with strand-specific reverse first-read mapping (Bray et al., Nat. Biotechnol., 2016, 34, 525). In some embodiments, transcript counts can be aggregated to gene counts. In some embodiments, the aggregation can be conducted using tximport (Soneson et al., F1000Research, 2015, 4, 1521).

In any of the methods described herein whereby a fourth transcriptome is screened against a third transcriptome to generate a cat allergen exposure/treatment/exposure transcriptome, particular thresholds can be used to determine whether a gene is considered to be upregulated or downregulated sufficiently in order to be included in the list of upregulated or downregulated genes described herein. For example, in some embodiments, the listed genes in the transcriptome identified from the screening can be selected to have a fold-change ≥2, and a $q<0.05$ in at least one study. In some embodiments, the listed genes in the transcriptome identified from the screening can be selected to have a fold-change ≥1.5, and a $q<0.05$ in at least one study. Alternately, a p value can be used instead of q value. In some embodiments, the listed genes in the transcriptome identified from the screening can be selected to have a $p<0.05$ in at least one study.

In some embodiments, the fold-change comprises subtracting the changes in expression in a placebo treatment group from the at least one antibody to a cat allergen treatment group.

In some embodiments, screening a fourth transcriptome against a third transcriptome to generate a cat allergen exposure/treatment/exposure transcriptome is carried out by comparing the gene expression after exposure to cat allergen and before treatment with at least one antibody to a cat allergen to the gene expression after exposure to a cat allergen, after treatment with at least one antibody to a cat allergen, and after a second exposure to a cat allergen. In some embodiments, the fourth transcriptome is generated from a biological sample that is obtained about 2 hours after treatment with at least one antibody to a cat allergen. In some embodiments, the fourth transcriptome is generated from a biological sample that is obtained about 4 hours after treatment with at least one antibody to a cat allergen. In some embodiments, the fourth transcriptome is generated from a biological sample that is obtained about 6 hours after treatment with at least one antibody to a cat allergen. In some embodiments, the fourth transcriptome is generated from a biological sample that is obtained about 8 hours after treatment with at least one antibody to a cat allergen. In some embodiments, the fourth transcriptome is generated from a biological sample that is obtained about 12 hours after treatment with at least one antibody to a cat allergen. In some embodiments, the fourth transcriptome is generated from a biological sample that is obtained about 18 hours after treatment with at least one antibody to a cat allergen. In some embodiments, the fourth transcriptome is generated from a biological sample that is obtained about 24 hours after treatment with at least one antibody to a cat allergen. In some embodiments, the fourth transcriptome is generated from a biological sample that is obtained about 48 hours after treatment with at least one antibody to a cat allergen. In some embodiments, the fourth transcriptome is generated from a biological sample that is obtained about 72 hours after treatment with at least one antibody to a cat allergen. In some embodiments, the fourth transcriptome is generated from a biological sample that is obtained about 1 week after treatment with at least one antibody to a cat allergen. In some embodiments, the fourth transcriptome is generated from a biological sample that is obtained about 2 weeks after treatment with at least one antibody to a cat allergen. In some embodiments, the fourth transcriptome is generated from a biological sample that is obtained about 3 weeks after treatment with at least one antibody to a cat allergen. In some embodiments, the fourth transcriptome is generated from a biological sample that is obtained about 1 week after treatment to about one year after treatment with at least one antibody to a cat allergen. In some embodiments, the fourth transcriptome is generated from a biological sample that is obtained about 1 month after treatment with at least one antibody to a cat allergen. In some embodiments, the fourth transcriptome is generated from a biological sample that is obtained about 2 months after treatment with at least one antibody to a cat allergen. In some embodiments, the fourth transcriptome is generated from a biological sample that is obtained about 3 months after treatment with at least one antibody to a cat allergen. In some embodiments, the fourth transcriptome is generated from a biological sample that is obtained about 4 months after treatment with at least one antibody to a cat allergen. In some embodiments, the fourth transcriptome is generated from a biological sample that is obtained about 5 months after treatment with at least one antibody to a cat allergen. In some embodiments, the fourth transcriptome is generated from a biological sample that is obtained about 6 months after treatment with at least one antibody to a cat allergen.

In some embodiments, the screening of the fourth transcriptome against the third transcriptome comprises: i) transforming the third transcriptome into z-scores; ii) ranking the z-scores; and ii) generating a gene expression signature (GES) for all ranked z-scores using at least one gene which is differentially expressed and is in the third transcriptome, thereby representing at least one change in the fourth transcriptome with respect to the third transcriptome. In some embodiments, the GES is generated using a gene set enrichment analysis tool that takes both at least one positive gene set and at least one negative gene set into consideration. In some embodiments, the GES is generated by: a) transforming each gene expression within at least one gene into a z-score, and ordering at least one gene that is differentially expressed from the most upregulated to the most downregulated values to generate a value of R+; b) identifying hits independently for the most up-regulated gene set (S+) in R+, and the most downregulated gene set (S−) in R−, wherein R− is the inversed ranking of R+ with inverted values; c) combining R+ and R− and reordering the values by keeping the hits for both S+ and S−; d) computing a running score by walking down the combined ranking, wherein the running score increases by $/r_i/^p/\Sigma_{i\in S}/r/^p$ if the $i^{th}$ gene is a hit, or decreases by 1/(2N−S), where S is the combined total number of genes in S+ and S−; r; is the value for gene i, and p is the weight for r; e) determining an Enrichment Score (ES) as a maximum deviation from zero along the running score; f) repeating steps a)-e) with a random gene set for 1,000 times to compute the ES null distribution; and g) generating the NES as ES divided by the mean of ES null distribution. In some embodiments, the methods further comprise computing the statistical significance by determining the $95^{th}$ percentile GES from healthy control samples. In some embodiments, when the GES of the subject is higher than the GES of a healthy control, the subject is suitable for the antibody treatment.

In any of the methods described herein, the methods can further comprise obtaining or having obtained a first biological sample and/or a second biological sample from the subject for generating or having generated the third transcriptome and/or fourth transcriptome, respectively. In some embodiments, the end user of the methods described herein obtains the first biological sample and/or the second biological sample from the subject. In some embodiments, a third party obtains the first biological sample and/or the second biological sample from the subject, wherein the end user of the methods described herein receives the first biological sample and/or the second biological sample from the third party or the subject. In some embodiments, the first biological sample and/or second biological sample comprises a sample from an organ, a tissue, a cell, and/or a biological fluid. In some embodiments, the first biological sample and/or second biological sample comprises a sample from an organ. In some embodiments, the first biological sample and/or second biological sample comprises a sample from a tissue. In some embodiments, the first biological sample and/or second biological sample comprises a sample from a cell. In some embodiments, the first biological sample and/or second biological sample comprises a sample from a biological fluid. In some embodiments, the first biological sample and/or second biological sample comprises blood, semen, saliva, urine, feces, hair, teeth, bone, nasal mucosal tissue, bronchial alveolar lavage sample, respiratory tissue sample, and/or a buccal sample. In some embodiments, the first biological sample and/or second biological sample comprises blood. In some embodiments, the first biological sample and/or second biological sample comprises semen. In some embodiments, the first biological sample and/or second biological sample comprises saliva. In some embodiments, the first biological sample and/or second biological sample comprises urine. In some embodiments, the first biological sample and/or second biological sample comprises feces. In some embodiments, the first biological sample and/or second biological sample comprises hair. In some embodiments, the first biological sample and/or second biological sample comprises teeth. In some embodiments, the first biological sample and/or second biological sample comprises bone. In some embodiments, the first biological sample and/or second biological sample comprises nasal mucosal tissue. In some embodiments, the first biological sample and/or second biological sample comprises bronchial alveolar lavage sample. In some embodiments, the first biological sample and/or second biological sample comprises respiratory tissue sample. In some embodiments, the first biological sample and/or second biological sample comprises a buccal sample. In some embodiments, the first biological sample is obtained from the subject by a biopsy. In some embodiments, the first biological sample and/or second biological sample comprises plasma. In some embodiments, the first biological sample and/or second biological sample comprises serum. In some embodiments, the first biological sample and/or second biological sample comprises lymph. In some embodiments, the first biological sample and/or second biological sample comprises semen. In some embodiments, the first biological sample and/or second biological sample comprises a nasal mucosal secretion. In some embodiments, the biological sample is obtained from the nasal mucosa via a nasal brushing.

The present disclosure also provides methods of treating a subject having asthma exacerbation induced by a cat allergen or preventing a subject from developing asthma exacerbation induced by a cat allergen. In some embodiments, the methods treat a subject having asthma exacerbation induced by a cat allergen. In some embodiments, the methods prevent a subject from developing asthma exacerbation induced by a cat allergen. In some embodiments, the methods can be used to treat a subject having allergic rhinitis without asthma induced by a cat allergen or preventing a subject from developing with allergic rhinitis without asthma induced by a cat allergen. In some embodiments, the methods can be used to treat a subject having allergic asthma induced by a cat allergen or preventing a subject from developing with allergic asthma induced by a cat allergen. The methods comprise administering at least one antibody to the cat allergen to the subject. In some embodiments, the methods comprise generating a cat allergen exposure transcriptome and/or a cat allergen exposure/treatment transcriptome and/or a cat allergen exposure/treatment/exposure transcriptome.

In some embodiments, the at least one antibody to the cat allergen comprises at least one antibody to Fel d 1, Fel d 2, Fel d 3, Fel d 4, Fel d 5, Fel d 6, Fel d 7, and/or Fel d 8, or any combination thereof. In some embodiments, the at least one antibody to the cat allergen comprises at least one antibody to Fel d 1. In some embodiments, the at least one antibody to the cat allergen comprises at least one antibody to Fel d 2. In some embodiments, the at least one antibody to the cat allergen comprises at least one antibody to Fel d 3. In some embodiments, the at least one antibody to the cat allergen comprises at least one antibody to Fel d 4. In some embodiments, the at least one antibody to the cat allergen comprises at least one antibody to Fel d 5. In some embodiments, the at least one antibody to the cat allergen comprises at least one antibody to Fel d 6. In some embodiments, the at least one antibody to the cat allergen comprises at least one antibody to Fel d 7. In some embodiments, the at least one antibody to the cat allergen comprises at least one antibody to Fel d 8. In some embodiments, the at least one antibody to the cat allergen comprises two monoclonal antibodies to Fel d 1. In some embodiments, the two monoclonal antibodies to Fel d 1 are fully human monoclonal antibodies. In some embodiments, the two fully human monoclonal antibodies to Fel d 1 comprises REGN1908 and REGN1909.

In some embodiments, the subject has been determined to have a cat allergen exposure transcriptome and/or a cat allergen exposure/treatment transcriptome and/or a cat allergen exposure/treatment/exposure transcriptome comprising: i) a downregulation of any of the genes, or susets thereof, described herein; and ii) an upregulation of any of the genes, or susets thereof, described herein. In any of the methods of treatment or prevention described herein, the cat allergen exposure transcriptome and/or a cat allergen exposure/treatment transcriptome and/or a cat allergen exposure/treatment/exposure transcriptome can be determined by any of the methods described herein.

In any of the embodiments described herein, the subject can be a cat-allergic mild asthmatic subject.

The present disclosure also provides methods of carrying out a clinical trial for asthma exacerbation induced by a cat allergen, whereby the clinical trial employs a cat allergen exposure transcriptome analysis or a cat allergen treatment transcriptome analysis as described herein to determine the suitability for treatment with at least one antibody to a cat allergen as a clinical endpoint for the clinical trial. In addition, any of the cat allergen exposure transcriptomes and/or cat allergen exposure/treatment transcriptomes and/or cat allergen exposure/treatment/exposure transcriptomes, or any comparison thereof, described herein can be used in a clinical endpoint analysis.

The present disclosure also provides at least one antibody to a cat allergen for use in treating a subject having asthma exacerbation induced by a cat allergen or for use in preventing a subject from developing asthma exacerbation induced by a cat allergen. The present disclosure also provides at least one antibody to a cat allergen for use in treating a subject having allergic rhinitis without asthma induced by a cat allergen or preventing a subject from developing with allergic rhinitis without asthma induced by a cat allergen. The present disclosure also provides at least one antibody to a cat allergen for use in treating a subject having allergic asthma induced by a cat allergen or preventing a subject from developing with allergic asthma induced by a cat allergen. In any of these embodiments, any of the cat allergen exposure transcriptome and/or a cat allergen exposure/treatment transcriptome and/or a cat allergen exposure/treatment/exposure transcriptome described herein can be generated. In any of these embodiments, any of the cat allergens described herein can be used. In any of these embodiments, any of the antibodies to a cat allergen described herein can be used.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for.

EXAMPLES

Example 1: General Methodology

Natural and Recombinant Fel d 1

Recombinant Fel d 1 (rFel d 1) was produced following the design of Kaiser et al. (J. Biol. Chem., 2003, 278, 37730-37735) who showed that single-chain fusions were structurally and functionally equivalent to the natural Fel d 1 (nFel d 1) heterodimer. The recombinant proteins included amino acids 18-109 of Fel d 1 Chain 2 (NP_001041619.1) at the N-terminus fused directly in-line to amino acids 23-92 of Fel d 1 Chain 1 (NP_001041618.1) with a D27G mutation and a C-term myc-myc-hexahistidine (mmh) tag. The proteins were produced in Chinese Hamster Ovary (CHO) cells with either a monomeric (mmh) or a dimeric ((mouse IgG2a Fc (mFc)) C-terminal tag (rFel d 1.mmh and rFel d 1.mFc, respectively).

Generation of REGN1908 and REGN1909

REGN1908 and REGN1909 are fully human monoclonal antibodies to Fel d 1 produced with $IgG4^P$ isotype Fc domains. The IgG4 constant domain contains a serine to proline amino acid substitution (S228P, EU numbering) in the hinge region that reconstructs the human IgG1 hinge sequence (CPPC) to promote stabilization of disulfide bonds between the two heavy chains (Yang et al., Curr. Opin. Biotechnol., 2014, 30, 225-229), therefore designated IgG4P. Briefly, VelocImmune mice (Macdonald et al., Proc. Natl. Acad. Sci. USA, 2014, 111, 5147-5152; Murphy et al., Proc. Natl. Acad. Sci. USA, 2014, 111, 5153-5158) were immunized with recombinant dimeric Fel d 1 (rFeld1.mFc). Hybridomas producing REGN1908 and REGN1909 were isolated and the variable regions were cloned onto plasmid vectors containing kappa light chain constant regions and $hIgG4^P$ heavy chain constant regions, respectively. Lead antibodies were selected based on affinity and the ability to bind non-competitively to Fel d 1.

Gene Expression NEC Signature

To generate a Naturalistic Exposure Chamber (NEC) gene signature, differentially expressed genes were identified using a paired analysis comparing post- vs pre-NEC in participants from the 0000-CES-1887: Chuck and Norris study. Genes were considered significant if the expression absolute fold change (FC) was greater than 2-fold ($|FC|>2$) and had a q-value <0.05.

Placebo-Controlled Permutation Based Differential Fold Change (dFC) Analysis

To determine placebo-controlled pharmacodynamic response signatures, a permutation-based differential fold change (dFC) analysis was performed to compute p-values of the placebo-controlled treatment signatures. DESeq2 was first run within the placebo and treatment groups, then the fold change difference was determined for each transcript across the groups. To implement permutation testing, DESeq2 was repeated 10,000 times to extract a background distribution of the dFC values, each time with a random assignment of the subjects to the placebo or treatment groups while keeping all baseline and post-treatment samples for each subject intact. A p-value for each gene was then computed from the resulting background distribution, comparing against the number of dFC values observed to be more extreme than the true dFC. This strategy enabled the use of the placebo group data in the analysis. Significant genes in overall treatment signatures were determined based on a $|dFC|>1.5$, p-value <0.05 threshold. A shorter list of genes was identified using a stricter threshold of $|dFC|>2$ and p-value <0.05.

Environmental Exposure Unit

The EEU used in the studies described herein is a 65 $m^2$ International Standards Organization 8 cleanroom (Standard 14644-1) with continuous air circulation, containing 20 seats to accommodate up to 20 patients at a single time, and with an anteroom and exit room. The EEU contains 10 particle counters spread equally throughout the room, and glass fiber filters adjacent to seats to be used for Fel d 1 allergen testing by ELISA. Standardized, commercially available cat hair extract prepared by a pharmacist was nebulized into the EEU through a specialized system that maintains consistent particle counts and Fel d 1 counts approximating 40 ng/$m^3$ across the 20 seat positions of the EEU. Particle counts and Fel d 1 counts fell below the limit of detection within minutes of stopping the nebulization and Fel d 1 measurements were below the limit of quantification outside of the EEU (e.g., in the observation area and in the rest rooms). Other allergens have been tested in the EEU, observation room, and the rest rooms and are below the limit of quantification (e.g., house dust mite, birch), suggesting that there is no cross-contamination of allergens. During each exposure, the patients wore protective suits (TS Plus Microgard 2000) to ensure that no contaminant enters or exits the EEU. The cleaning procedure after each EEU exposure session included the following: rinsing of the nebulization system, disinfectant of the floor, walls, the armchairs, and of all the small material stored in the EEU (Ecowipes, THX medical). Additionally, air qualification was performed by an independent company (Air Qualif) 4 times a year to test for the absence of bacteria and molds in the EEU.

Nasal Brushing Samples

Nasal brushing samples are collected from the patients before and after cat allergen challenge in the EEU on the day of the screening challenge (Visit 3) and day 29 (Visit 7). Before the challenge in the EEU, a baseline nasal brushing is performed in 1 nare and the samples are processed. Six hours from the start of the EEU challenge, a nasal brushing is performed in the contralateral nare and the sample is processed. Nasal brushing is performed by a clinician experienced in nasal procedures under direct visualization, by inserting a soft, sterile cytobrush into the nare alongside the inferior nasal turbinate of 1 nostril approximately 0.5 cm above the floor of the nose and 1.5 cm into the nasal cavity and rotating the brush 180 degrees once to the lateral aspect of the nostril. RNA is extracted from nasal brushing samples and is used to perform RNA sequencing to determine changes in type 2 inflammation in the nasal mucosa.

Nasal brushing samples were of good quality and were used for RNAseq analysis. In brief, RNAseq analysis was carried out as follows: i) paired comparisons within treatment arms were performed using DESeq2 (Love et al., Genome Biol., 2014, 15, 550); ii) q values were calculated using the qvalue package (Storey et al., 2020 qvalue: Q-value estimation for false discovery rate control R package version 2.20.0); iii) differential FC analyses, a novel approach to that compares gene expression changes on treatment to those observed on placebo, was used to assess placebo-controlled REGN1908/1909 treatment effects; and iv) genes were considered significant if the expression absolute FC was greater than two-fold ($|FC|>2$) and had q 0.05 (FC, fold change). Total RNA was extracted from each nasal brushing sample using the Kapa mRNA HyperPrepkit (Roche). Libraries were prepared with 100 ng RNA as input, and sequenced using 80 base pair single-read sequencing on an Illumina HiSeq2500. Samples with RNA Quality Number >5 were high quality and used in analyses.

Example 2: Chuck and Norris Naturalistic Exposure Chamber (NEC)

Overview of study participants and samples: N=31 at baseline (screening) pre-NEC; N=27 at day 28 6 hours post-NEC; N=21 paired samples total.

Clinical measurements: Total ocular symptom score (TOSS); Total nasal symptom score (TNSS); Spirometry (FEV1); Peak nasal inspiratory flow (PNIF); Serum for specific IgE for Fel d 1 and cat hair; Serum for total IgE; Serum for sIgE and sIgG4 tests.

Naturalistic exposure chamber induces changes in nasal brushing epithelial cells after exposure to cat allergen in GINA-1 asthma cat-allergic subjects:

N=21 paired samples were used to derive NEC cat exposure signature (|log 2FC|>1 and q<0.05) post-NEC vs pre-NEC (74 genes upregulated; 37 genes downregulated; see, Table 1).

TABLE 1

| Gene | log2FoldChange | qvalue |
|---|---|---|
| CCDC33 | −1.79481 | 0.01556 |
| ADH6 | −1.7334 | 0.017754 |
| IFLTD1 | −1.59883 | 0.035603 |
| DLGAP1-AS5 | −1.58651 | 0.035354 |
| DNAJB13 | −1.53188 | 0.033363 |
| C2orf62 | −1.47199 | 0.046723 |
| CCDC81 | −1.46673 | 0.023821 |
| 10-Mar | −1.46006 | 0.047611 |
| PIH1D3 | −1.45509 | 0.048239 |
| NHLRC4 | −1.43534 | 0.049894 |
| TMEM190 | −1.42917 | 0.040391 |
| AK090700 | −1.42422 | 0.024714 |
| KIF6 | −1.3629 | 0.034871 |
| BBOX1 | −1.34723 | 0.03995 |
| PTGFR | −1.26331 | 0.02738 |
| SEC14L3 | −1.22388 | 0.040142 |
| BC022056 | −1.2101 | 0.026242 |
| CASC2 | −1.20246 | 0.041525 |
| PPP1R36 | −1.18815 | 0.011579 |
| CNTN5 | −1.17643 | 0.026732 |
| KLHDC8A | −1.1689 | 0.047381 |
| FHOD3 | −1.14418 | 0.006321 |
| CAPS | −1.14289 | 0.049978 |
| UBD | −1.1201 | 0.011591 |
| TP73 | −1.09225 | 0.042786 |
| BC023516 | −1.08281 | 0.04459 |
| IFI44L | −1.07679 | 0.027975 |
| FAM86B1 | −1.07351 | 0.046861 |
| CX3CL1 | −1.06758 | 0.003161 |
| ACY3 | −1.05604 | 0.004818 |
| MPDZ | −1.05132 | 0.03768 |
| IGFBP5 | −1.05028 | 0.014727 |
| AK097288 | −1.04838 | 0.011579 |
| IFI6 | −1.03549 | 0.01556 |
| ABCC6 | −1.03046 | 0.014924 |
| GAS1 | −1.02758 | 0.003811 |
| PLCH1 | −1.02347 | 0.041625 |
| ESPL1 | 1.01781 | 0.026981 |
| NMU | 1.02392 | 0.015518 |
| CTSL2 | 1.032258 | 0.026732 |
| CLIC3 | 1.035363 | 0.026732 |
| CRABP2 | 1.039501 | 0.038634 |
| AX746775 | 1.050299 | 0.004011 |
| TMPRSS11A | 1.062696 | 0.003801 |
| NCCRP1 | 1.083012 | 0.041578 |
| MSX2 | 1.083807 | 0.005115 |
| HSP90AB4P | 1.084446 | 0.040898 |
| AIM1L | 1.087736 | 0.003161 |
| SERPINB2 | 1.093661 | 0.01452 |
| IL1RN | 1.112146 | 0.036737 |
| KLK10 | 1.121727 | 0.029311 |
| PXDN | 1.124204 | 0.007848 |
| HSPB8 | 1.124986 | 0.027219 |
| CLCA4 | 1.130655 | 0.003161 |
| KRT10 | 1.135585 | 0.004878 |
| ZBED2 | 1.151707 | 0.018174 |
| DSC2 | 1.156319 | 0.004878 |
| LY6G6C | 1.168836 | 0.021674 |
| ADAMTSL4 | 1.177534 | 0.023297 |
| OTOP3 | 1.180365 | 0.026732 |
| FGFBP1 | 1.197275 | 0.013627 |
| GPR115 | 1.213246 | 0.029997 |
| TRPV3 | 1.214555 | 0.002351 |
| CRISP3 | 1.218238 | 0.023953 |
| SPRR3 | 1.221286 | 0.021145 |
| PRSS3 | 1.22759 | 0.031722 |
| A2ML1 | 1.228853 | 0.003161 |
| SPINK7 | 1.262327 | 0.046582 |
| LYPD3 | 1.269337 | 0.009259 |
| RHCG | 1.272195 | 0.029311 |
| SPRR1A | 1.278132 | 0.027219 |
| MAP2 | 1.280436 | 0.00945 |

TABLE 1-continued

| Gene | log2FoldChange | qvalue |
|---|---|---|
| S100A8 | 1.282436 | 0.042723 |
| RPTN | 1.285138 | 0.028373 |
| PRSS27 | 1.285988 | 0.021145 |
| KRT6B | 1.290329 | 0.027836 |
| PPP2R2C | 1.316214 | 0.026732 |
| IL1RL1 | 1.343067 | 0.046757 |
| CAMK2N1 | 1.354724 | 0.021901 |
| CPA4 | 1.356636 | 0.004418 |
| KLK13 | 1.36646 | 0.039168 |
| SERPINB13 | 1.391489 | 0.001074 |
| ALOX12 | 1.393499 | 0.01823 |
| SLC39A2 | 1.429526 | 0.004011 |
| KRT4 | 1.429862 | 0.000214 |
| HOPX | 1.456029 | 0.000686 |
| FAM25A | 1.463268 | 0.037786 |
| EMP1 | 1.473992 | 0.004418 |
| CNFN | 1.474604 | 0.017645 |
| KLK12 | 1.481839 | 0.026732 |
| APOBEC3A | 1.503537 | 0.011093 |
| CAPN14 | 1.514636 | 0.006484 |
| IVL | 1.524412 | 0.014089 |
| KLK8 | 1.52804 | 0.023953 |
| SPRR1B | 1.536349 | 0.032803 |
| IGFBP6 | 1.538672 | 0.010396 |
| IL36G | 1.560252 | 0.036628 |
| KLK7 | 1.570266 | 0.017645 |
| EGR3 | 1.578932 | 0.026732 |
| KRT78 | 1.620729 | 0.007049 |
| CRNN | 1.633685 | 0.02677 |
| MAL | 1.650465 | 0.015735 |
| LINC00707 | 1.6877 | 0.004418 |
| KRT24 | 1.722973 | 0.000764 |
| KRT6A | 1.737437 | 0.011328 |
| TMPRSS11B | 1.762219 | 0.011675 |
| KRT14 | 1.842136 | 0.035308 |
| PRB3 | 1.957297 | 0.004418 |
| KRT13 | 1.966609 | 0.00012 |
| LOC731424 | 2.024037 | 0.041714 |
| BCL2L2-PABPN1 | 4.532472 | 0.001985 |

The NEC cat exposure signature visibility (qualitatively) was different when visualizing within group at each timepoint or when looking at paired log 2fold change within a subject. 36 gene REGN Type 2 Inflammation Signature was significantly enriched after NEC (NES=1.95, q<0.001). See Collins et al., Dupilumab improves histological outcomes and normalizes disease and type 2 inflammation transcriptome signatures in adult and adolescent patients with eosinophilic oesophagitis: results from the 3-part phase 3 LIBERTY EoE TREET study. Allergy 2023; 78:S111. EAACI Annual Congress 2022; Prague. Abstract: 001140. Separately, in two unpublished studies, core AR disease signature (R668-ALG-16115) was significantly enriched after NEC (NES=1.92, q=0.02), and the AR In Season Only signature (R668-ALG-16115) was more significantly enriched after NEC (NES=2.78, q<0.001).

Several core asthma gene signatures were upregulated by NEC: 1) Internal BAC signature from R3500-AS-1633 (NES=2.52, q<0.001); 2) Published nasal brushings dataset (NES=2.11, q<0.001): a) PMID: 32640237 and 33046696 and GEO: GSE152004; b) N=441 asthma N=254 HC: split asthma into type 2 (N=101) and non-type 2 subsets (N=340) and derived a type 2 asthma signature; 3) Published airway epithelial gene signature (NES=1.69, q=0.00068): a) PMID: 27942592 and GEO: GSE85567, and b) N=57 asthma vs N=28 controls.

Genes for discussion regulated by NEC included: 1) immune-related: ALOX12, IL1RL1/IL1RN, and IL36G; 2) epithelial-related; and 3) keratinocyte-related.

Example 3: REGN1908-1909 Environmental Exposure Unit (EEU)

Overview of study participants and samples: Placebo: N=23 at baseline (screening) post-EEU, and N=21 one month post treatment, post-EEU. R1908-1909 Treatment: N=24 at baseline (screening) post-EEU, and N=29 one month post treatment, post-EEU.

Clinical measurements: TNSS nasal symptoms score; TOSS ocular symptoms score; Spirometry (includes FEV1); PNIF; Skin Prick Test with Serial Allergen Titration (Cat-SPT); FeNO; Serum for specific IgE for Fel d 1 and cat hair; and Serum for sIgE (Fel-D 2, 4, 7) tests.

Transcriptomic Differences Revealed by Baseline Anti-Cat sigE and Asthma Clinical Response Variables:

Treatment signatures were generated for paired placebo, treatment, and placebo-controlled comparisons (|log 2FC|>1 and q<0.05) post-EEU vs pre-EEU. N=18 paired samples in placebo arm (251 genes upregulated; 197 genes downregulated). N=25 paired samples in R1908-1909 arm (39 genes upregulated; 10 genes downregulated). Placebo-controlled treatment signature derived (572 genes upregulated by treatment relative to placebo; 150 genes downregulated by treatment relative to placebo; see, Table 2).

TABLE 2

| Gene | dFC | dFC p |
|---|---|---|
| BC007880 | −3.34157 | 0.016194 |
| BC080587 | −2.65396 | 0.012146 |
| BX537909 | −1.44076 | 0.020243 |
| NGS-17 | −1.2322 | 0.006748 |
| LOC100862671 | −1.12885 | 0.025641 |
| AX747215 | −1.12384 | 0 |
| P2RX1 | −1.10492 | 0.041835 |
| SDS | −1.08107 | 0.005398 |
| S1PR4 | −1.06007 | 0.049933 |
| RPPH1 | −1.05422 | 0.021592 |
| ARPC4-TTLL3 | −1.05186 | 0.036437 |
| SERPING1 | −1.01 | 0.049933 |
| PLA2G4B | −0.99391 | 0.018893 |
| C5orf27 | −0.97345 | 0 |
| AX748196 | −0.96215 | 0.013495 |
| GPR89C | −0.94035 | 0.002699 |
| LOC494150 | −0.93888 | 0.026991 |
| TNFSF12-TNFSF13 | −0.91896 | 0.006748 |
| AX746775 | −0.91263 | 0.00135 |
| DUOXA2 | −0.90072 | 0.032389 |
| CYP2D6 | −0.89434 | 0 |
| APOC1 | −0.87676 | 0.018893 |
| P2RY8 | −0.87595 | 0.047233 |
| DQ574721 | −0.87196 | 0.013495 |
| NCF4 | −0.86991 | 0.048583 |
| GATA2 | −0.86658 | 0.045884 |
| TYROBP | −0.85863 | 0.033738 |
| IFI6 | −0.8528 | 0.032389 |
| C17orf96 | −0.84856 | 0.012146 |
| SPC25 | −0.84746 | 0.012146 |
| FLJ45445 | −0.8457 | 0.020243 |
| RAB42 | −0.84568 | 0.00135 |
| IFITM1 | −0.83903 | 0.010796 |
| SECTM1 | −0.83892 | 0.039136 |
| HMOX1 | −0.83814 | 0.012146 |
| FLJ39739 | −0.83814 | 0.02834 |
| DUSP2 | −0.83596 | 0.010796 |
| IQGAP3 | −0.83323 | 0.012146 |
| ASPG | −0.81752 | 0.010796 |
| TROAP | −0.81087 | 0.010796 |
| ISG15 | −0.80902 | 0.032389 |
| SNX22 | −0.80701 | 0.012146 |
| EGR1 | −0.8035 | 0.044534 |
| PILRA | −0.7934 | 0.049933 |
| CBS | −0.79038 | 0.004049 |
| ANGPTL2 | −0.78943 | 0.012146 |
| GTSE1 | −0.78849 | 0.002699 |

TABLE 2-continued

| Gene | dFC | dFC p |
|---|---|---|
| AX747103 | −0.78798 | 0.002699 |
| KIF18B | −0.78712 | 0.017544 |
| APOE | −0.78542 | 0.009447 |
| IFITM2 | −0.78214 | 0.047233 |
| AQP7P1 | −0.78004 | 0.008097 |
| GLTPD2 | −0.7724 | 0.004049 |
| MROH6 | −0.77087 | 0.00135 |
| TMEM88 | −0.76913 | 0.024291 |
| FAM173A | −0.76683 | 0 |
| SH2B2 | −0.75838 | 0.048583 |
| MYBL2 | −0.75719 | 0.012146 |
| LY6D | −0.75593 | 0.02834 |
| SH2D3C | −0.75177 | 0.035088 |
| KCNN4 | −0.74437 | 0.004049 |
| BC033281 | −0.73845 | 0.020243 |
| LOXL3 | −0.73794 | 0.006748 |
| AK098481 | −0.72936 | 0.035088 |
| PTP4A3 | −0.72887 | 0.00135 |
| LOC645638 | −0.72704 | 0.020243 |
| PRG2 | −0.72059 | 0.018893 |
| C1orf162 | −0.71998 | 0.043185 |
| GPAT2 | −0.71782 | 0.009447 |
| PI3 | −0.71724 | 0.013495 |
| BC031876 | −0.71618 | 0.002699 |
| KIAA1656 | −0.71465 | 0 |
| ESPL1 | −0.71308 | 0.036437 |
| PDE4C | −0.70918 | 0.032389 |
| OSR1 | −0.70777 | 0 |
| KANK3 | −0.70314 | 0.014845 |
| IFI30 | −0.7031 | 0.024291 |
| SAC3D1 | −0.69987 | 0 |
| SLC7A5P2 | −0.69673 | 0.026991 |
| FAM53A | −0.6965 | 0.004049 |
| HR | −0.69372 | 0.006748 |
| ICAM3 | −0.69367 | 0.043185 |
| AMICA1 | −0.68562 | 0.047233 |
| S100A16 | −0.68459 | 0.002699 |
| VAMP5 | −0.68315 | 0.017544 |
| HLA-L | −0.68102 | 0.005398 |
| LSMEM1 | −0.67895 | 0.040486 |
| C16orf59 | −0.67777 | 0.02969 |
| CD14 | −0.67513 | 0.037787 |
| RPL21P44 | −0.67397 | 0.047233 |
| AKR1B15 | −0.6709 | 0.024291 |
| STX1B | −0.66885 | 0.025641 |
| LCN2 | −0.66682 | 0.017544 |
| ITGA5 | −0.66632 | 0.043185 |
| PIF1 | −0.6663 | 0.02969 |
| AURKB | −0.66624 | 0.021592 |
| DEFB1 | −0.65991 | 0.022942 |
| SLC26A9 | −0.6571 | 0.049933 |
| MPP1 | −0.65623 | 0.02834 |
| FCHO1 | −0.65611 | 0.039136 |
| SLC15A3 | −0.65545 | 0.006748 |
| LOC100132247_2 | −0.65487 | 0.047233 |
| CDR2L | −0.65184 | 0.002699 |
| IFITM3 | −0.64908 | 0.025641 |
| SPINK5 | −0.6488 | 0.009447 |
| FGFBP1 | −0.64622 | 0.022942 |
| WBSCR17 | −0.64551 | 0.010796 |
| SFN | −0.63707 | 0.020243 |
| FAIM2 | −0.63407 | 0.00135 |
| LIMD2 | −0.63238 | 0.037787 |
| DOK2 | −0.62996 | 0.037787 |
| HLA-G | −0.62892 | 0.020243 |
| LOC100505702 | −0.6289 | 0.005398 |
| AK091729 | −0.62516 | 0.033738 |
| CDC25C | −0.62503 | 0.016194 |
| PHLDA2 | −0.62352 | 0.009447 |
| ASS1 | −0.62293 | 0.006748 |
| AL832439 | −0.61904 | 0.048583 |
| BC131755 | −0.61761 | 0.031039 |
| GGT1 | −0.61603 | 0.005398 |
| TAP1 | −0.61366 | 0.02834 |
| C1orf233 | −0.61353 | 0.004049 |
| LYL1 | −0.61319 | 0.02834 |
| BST2 | −0.60897 | 0.021592 |
| KIF2C | −0.60696 | 0.006748 |

TABLE 2-continued

| Gene | dFC | dFC p |
|---|---|---|
| B3GNT8 | −0.60683 | 0.02834 |
| APOL2 | −0.60656 | 0.021592 |
| ARHGAP11B | −0.60572 | 0.039136 |
| MEOX1 | −0.60428 | 0.043185 |
| LY6E | −0.60273 | 0.00135 |
| ACP5 | −0.60262 | 0.018893 |
| CLIC3 | −0.60074 | 0.02834 |
| OVCA2 | −0.59999 | 0.012146 |
| IFI27 | −0.59812 | 0.012146 |
| C4orf48 | −0.59666 | 0.041835 |
| CTRL | −0.59548 | 0.025641 |
| ASPHD2 | −0.59382 | 0.006748 |
| ZDHHC18 | −0.59371 | 0.016194 |
| N4BP3 | −0.59362 | 0.002699 |
| SPHK1 | −0.59187 | 0.016194 |
| NPCEDRG | −0.59079 | 0.018893 |
| ACTL10 | −0.58899 | 0 |
| LINC00887 | −0.5887 | 0.044534 |
| GPRIN2 | −0.58842 | 0.025641 |
| RCN3 | −0.58842 | 0 |
| CR749689 | −0.58806 | 0.021592 |
| ANK1 | −0.58805 | 0.014845 |
| GPX2 | −0.5873 | 0.00135 |
| TNFRSF18 | −0.58654 | 0.020243 |
| WFDC2 | −0.58592 | 0.00135 |
| KIAA1430 | 0.585571 | 0.002699 |
| SLC9C2 | 0.585581 | 0.045884 |
| MUC15 | 0.585663 | 0.005398 |
| LINC00271 | 0.585891 | 0.024291 |
| ZNF569 | 0.587298 | 0.002699 |
| BHLHE41 | 0.587314 | 0.005398 |
| DNAH1 | 0.588492 | 0.021592 |
| ZNF833P | 0.588858 | 0.039136 |
| ATG9B | 0.589189 | 0.047233 |
| ACBD7 | 0.589251 | 0.017544 |
| THSD4 | 0.589312 | 0.02834 |
| AADAT | 0.589471 | 0.004049 |
| GRAMD1C | 0.590441 | 0.004049 |
| NIPSNAP3B | 0.590563 | 0.02834 |
| HIPK1 | 0.590789 | 0.006748 |
| INTU | 0.591227 | 0.018893 |
| LOC100506599 | 0.591785 | 0.018893 |
| ZBTB41 | 0.593193 | 0.020243 |
| POLQ | 0.593213 | 0.036437 |
| PTPRT | 0.593606 | 0.013495 |
| SPAG16 | 0.59436 | 0.014845 |
| TCTN2 | 0.594834 | 0.013495 |
| TSPY26P | 0.594982 | 0.049933 |
| SHROOM3 | 0.595473 | 0.00135 |
| PCDHGB6 | 0.596191 | 0.009447 |
| TBC1D19 | 0.596384 | 0.005398 |
| IFT81 | 0.596394 | 0.016194 |
| TRIP13 | 0.596725 | 0.043185 |
| NME7 | 0.600221 | 0.021592 |
| C9orf72 | 0.600317 | 0.004049 |
| TDRP | 0.600968 | 0.02969 |
| KIAA1841 | 0.601749 | 0.002699 |
| PARD6B | 0.602677 | 0.004049 |
| FBXO36 | 0.602683 | 0.012146 |
| IQCG | 0.603703 | 0.039136 |
| CCP110 | 0.604365 | 0.002699 |
| TCP11L2 | 0.604409 | 0.010796 |
| ZFP82 | 0.605121 | 0.002699 |
| SPATA6L | 0.605576 | 0.018893 |
| CYB5D1 | 0.608161 | 0.018893 |
| NLRP14 | 0.608384 | 0.045884 |
| SLFN13 | 0.608513 | 0.012146 |
| AK092541 | 0.609125 | 0.043185 |
| DNAJB4 | 0.609326 | 0.006748 |
| CCDC30 | 0.609338 | 0.040486 |
| LPAR3 | 0.609516 | 0.002699 |
| FAM201A | 0.609631 | 0.014845 |
| ZNF713 | 0.610104 | 0.009447 |
| GNN | 0.610234 | 0.022942 |
| AOX1 | 0.610261 | 0.024291 |
| FAM172A | 0.61041 | 0.00135 |
| KITLG | 0.610628 | 0.021592 |
| DMD | 0.612653 | 0.009447 |

TABLE 2-continued

| Gene | dFC | dFC p |
|---|---|---|
| FLJ13197 | 0.612753 | 0.035088 |
| HSPA4L | 0.613415 | 0.009447 |
| C5orf42 | 0.613933 | 0.010796 |
| CCDC144B | 0.614411 | 0.021592 |
| SNCAIP | 0.614451 | 0.021592 |
| CD24 | 0.614996 | 0.006748 |
| MICU3 | 0.615622 | 0.005398 |
| WDR19 | 0.615646 | 0.004049 |
| AK9 | 0.615829 | 0.013495 |
| LOC100499183 | 0.616423 | 0.013495 |
| SLC2A13 | 0.61761 | 0.024291 |
| TP53INP1 | 0.618006 | 0.00135 |
| AK124973 | 0.619565 | 0.045884 |
| DNALI1 | 0.620891 | 0.039136 |
| DNM3 | 0.621083 | 0.044534 |
| LOC728024 | 0.621741 | 0.006748 |
| SHROOM4 | 0.622374 | 0.010796 |
| UBE2Q2P2 | 0.623013 | 0.040486 |
| TCTN1 | 0.623759 | 0.020243 |
| SNX29P2 | 0.624694 | 0.026991 |
| PDK4 | 0.624866 | 0.00135 |
| NCALD | 0.626031 | 0.014845 |
| C1orf101 | 0.626267 | 0.005398 |
| BTG4 | 0.62644 | 0.040486 |
| AX747742 | 0.627093 | 0.014845 |
| FMN1 | 0.627384 | 0.016194 |
| THAP10 | 0.628651 | 0.004049 |
| ZNF788 | 0.629314 | 0.004049 |
| GJB7 | 0.629413 | 0.026991 |
| AZIN1 | 0.629774 | 0.002699 |
| AQP4 | 0.630848 | 0.005398 |
| RNF32 | 0.631345 | 0.026991 |
| CLMN | 0.632229 | 0.008097 |
| CD38 | 0.632428 | 0.022942 |
| ENPP3 | 0.634817 | 0.018893 |
| MLF1 | 0.635374 | 0.035088 |
| PPP1R9A | 0.635433 | 0.02969 |
| WDR93 | 0.636339 | 0.049933 |
| EFCAB7 | 0.636582 | 0.006748 |
| ZNF214 | 0.636664 | 0.008097 |
| KCTD12 | 0.636773 | 0.020243 |
| C15orf26 | 0.638738 | 0.024291 |
| VWA7 | 0.640184 | 0.018893 |
| CCDC60 | 0.64266 | 0.016194 |
| IPMK | 0.644721 | 0.006748 |
| LOC100132111 | 0.645238 | 0.016194 |
| TMEM133 | 0.645491 | 0.002699 |
| BC039122 | 0.645856 | 0.022942 |
| CLCNKA | 0.646484 | 0.033738 |
| STXBP4 | 0.646715 | 0.008097 |
| USP51 | 0.646822 | 0.022942 |
| TTC16 | 0.647938 | 0.049933 |
| MAK | 0.651034 | 0.013495 |
| WDR66 | 0.651182 | 0.043185 |
| SRGAP2C | 0.651289 | 0.00135 |
| FTO | 0.652842 | 0.00135 |
| KLLN | 0.653541 | 0.008097 |
| COL21A1 | 0.653827 | 0.039136 |
| SGMS2 | 0.654581 | 0.005398 |
| LRGUK | 0.65487 | 0.022942 |
| LY75 | 0.655424 | 0.008097 |
| CLHC1 | 0.655458 | 0.014845 |
| SOX2-OT | 0.655488 | 0.016194 |
| ZNF610 | 0.65603 | 0.00135 |
| NXF2 | 0.656245 | 0.049933 |
| TMEM47 | 0.656482 | 0.010796 |
| ST8SIA1 | 0.656594 | 0.025641 |
| RAB36 | 0.656764 | 0.02834 |
| TGFB2 | 0.657968 | 0.016194 |
| LOC402160 | 0.658223 | 0.035088 |
| KIAA1751 | 0.65841 | 0.036437 |
| DGKH | 0.659124 | 0.043185 |
| DCLK1 | 0.659402 | 0.021592 |
| TDRD1 | 0.659617 | 0.048583 |
| MAGI2 | 0.661483 | 0.009447 |
| PDE8B | 0.662072 | 0.008097 |
| ETV1 | 0.66228 | 0.010796 |
| MAP9 | 0.662285 | 0.021592 |

TABLE 2-continued

| Gene | dFC | dFC p |
|---|---|---|
| PLAC4 | 0.662503 | 0.044534 |
| ENPP4 | 0.663098 | 0.00135 |
| SQLE | 0.66324 | 0.004049 |
| POLI | 0.664143 | 0 |
| LOC653513 | 0.664776 | 0.049933 |
| DLGAP1 | 0.665107 | 0 |
| CCDC41 | 0.665905 | 0.002699 |
| DCBLD2 | 0.666044 | 0.004049 |
| SLC4A8 | 0.666181 | 0.013495 |
| C11orf92 | 0.666498 | 0.018893 |
| FANK1 | 0.666517 | 0.031039 |
| AK127787 | 0.666523 | 0.010796 |
| PCNXL4 | 0.666744 | 0.00135 |
| SLC22A4 | 0.666799 | 0.02969 |
| DGKB | 0.669746 | 0.014845 |
| C9orf9 | 0.669795 | 0.026991 |
| MBNL2 | 0.670206 | 0.008097 |
| CCDC74B | 0.670233 | 0.040486 |
| TTLL9 | 0.670466 | 0.048583 |
| ANKRD45 | 0.670678 | 0 |
| WDR52 | 0.67113 | 0.022942 |
| B3GNT5 | 0.672114 | 0.008097 |
| LRTOMT | 0.673266 | 0.039136 |
| FAM179B | 0.674524 | 0.002699 |
| OSBPL6 | 0.675226 | 0.032389 |
| IPW | 0.675426 | 0.002699 |
| PLCH1 | 0.675498 | 0.008097 |
| KIAA1211 | 0.675535 | 0.008097 |
| FAM227B | 0.675806 | 0.009447 |
| LRRC34 | 0.675965 | 0.049933 |
| EGLN3 | 0.676199 | 0.008097 |
| ASB9 | 0.676475 | 0.041835 |
| CSMD1 | 0.676641 | 0.009447 |
| KIAA1456 | 0.677778 | 0.009447 |
| CDHR2 | 0.679182 | 0.020243 |
| CALCRL | 0.679722 | 0.025641 |
| GPR111 | 0.680719 | 0.009447 |
| AK021563 | 0.682388 | 0.020243 |
| AK096475 | 0.682768 | 0.006748 |
| SNED1 | 0.682817 | 0.012146 |
| MYEF2 | 0.683081 | 0.02834 |
| CCDC147 | 0.683287 | 0.040486 |
| LCA5L | 0.683707 | 0.033738 |
| C5 | 0.683796 | 0.02834 |
| C9orf117 | 0.684837 | 0.049933 |
| ENPP2 | 0.685486 | 0.021592 |
| FAM182B | 0.687412 | 0.024291 |
| NCR3LG1 | 0.687736 | 0.02834 |
| LINC00886 | 0.688043 | 0.017544 |
| AK024242 | 0.688487 | 0.035088 |
| FHOD3 | 0.688589 | 0.031039 |
| SEMA3C | 0.68906 | 0.017544 |
| DNAL1 | 0.68955 | 0.006748 |
| AK128656 | 0.68969 | 0.014845 |
| CASC1 | 0.690617 | 0.031039 |
| BCDIN3D-AS1 | 0.693254 | 0.017544 |
| SH3GL3 | 0.693378 | 0.035088 |
| CCDC170 | 0.693499 | 0.036437 |
| KIAA1257 | 0.694285 | 0.009447 |
| SCN4B | 0.694529 | 0.024291 |
| MEP1A | 0.695392 | 0.022942 |
| DZANK1 | 0.695724 | 0.005398 |
| DPY19L2P3 | 0.695788 | 0.016194 |
| NLGN4X | 0.696349 | 0.045884 |
| TTC30A | 0.696381 | 0.00135 |
| BC077729 | 0.697165 | 0.004049 |
| TEAD1 | 0.697187 | 0.009447 |
| AK128708 | 0.697273 | 0.012146 |
| CCDC108 | 0.697807 | 0.048583 |
| TTC40 | 0.698771 | 0.018893 |
| TMEM231 | 0.69944 | 0.017544 |
| LINC00883 | 0.699694 | 0.016194 |
| TTC23L | 0.700033 | 0.004049 |
| PPARGC1A | 0.700197 | 0.002699 |
| DQ573539 | 0.702413 | 0.022942 |
| FER1L5 | 0.702762 | 0.044534 |
| HIPK3 | 0.702974 | 0.013495 |
| ARHGAP18 | 0.703289 | 0.002699 |

TABLE 2-continued

| Gene | dFC | dFC p |
|---|---|---|
| TIGD4 | 0.704171 | 0.017544 |
| IQCD | 0.704475 | 0.02834 |
| CCDC67 | 0.704622 | 0.014845 |
| FAM175A | 0.704866 | 0.00135 |
| C4orf22 | 0.706574 | 0.040486 |
| LDLRAD1 | 0.707562 | 0.033738 |
| LRRIQ1 | 0.709047 | 0.045884 |
| CLDN16 | 0.710913 | 0.016194 |
| COL28A1 | 0.711761 | 0.040486 |
| DPY19L2P4 | 0.713673 | 0.031039 |
| EXTL2 | 0.713962 | 0.00135 |
| TTC21B | 0.71404 | 0.009447 |
| MPZL3 | 0.714401 | 0.020243 |
| EIF5A2 | 0.715448 | 0.00135 |
| STOML3 | 0.715666 | 0.045884 |
| C7orf57 | 0.715959 | 0.013495 |
| C11orf65 | 0.716632 | 0.014845 |
| FILIP1 | 0.716811 | 0.049933 |
| LOC285419 | 0.71705 | 0.031039 |
| BC043582 | 0.717872 | 0.018893 |
| SPATA6 | 0.718442 | 0.002699 |
| TRIM36 | 0.719495 | 0.008097 |
| TCTE1 | 0.719548 | 0.02834 |
| SENP7 | 0.719701 | 0.008097 |
| EML1 | 0.72056 | 0.009447 |
| DZIP3 | 0.7217 | 0.010796 |
| PCDH19 | 0.72357 | 0.02834 |
| KCNRG | 0.724501 | 0.02969 |
| ZNF204P | 0.724814 | 0.002699 |
| TTC29 | 0.725356 | 0.037787 |
| PROM1 | 0.725482 | 0.004049 |
| STOX1 | 0.725596 | 0.014845 |
| CTGF | 0.726806 | 0.024291 |
| UMODL1 | 0.726918 | 0.02969 |
| PCYT1B | 0.727353 | 0.020243 |
| AS3MT | 0.72811 | 0.02834 |
| GPR156 | 0.728863 | 0.017544 |
| C11orf63 | 0.728927 | 0.004049 |
| LINC00332 | 0.729677 | 0.049933 |
| C2orf50 | 0.730489 | 0.016194 |
| LOC100130992 | 0.731433 | 0.018893 |
| PPP1R36 | 0.731472 | 0.025641 |
| AK311578 | 0.732335 | 0.018893 |
| ESRRG | 0.732488 | 0.006748 |
| C11orf70 | 0.733162 | 0.022942 |
| GLIS3 | 0.733401 | 0.004049 |
| LINC00478 | 0.734282 | 0.002699 |
| CNGA4 | 0.735314 | 0.025641 |
| TNFRSF19 | 0.735866 | 0.004049 |
| DNAI1 | 0.736599 | 0.031039 |
| CHST9 | 0.736784 | 0.00135 |
| TSGA10 | 0.739283 | 0.004049 |
| MKX | 0.740507 | 0.008097 |
| ENKUR | 0.740635 | 0.025641 |
| CCDC138 | 0.740646 | 0.002699 |
| SPAG17 | 0.741284 | 0.035088 |
| ZNF487P | 0.741947 | 0.00135 |
| EFHC1 | 0.744471 | 0.016194 |
| BC032795 | 0.744521 | 0.037787 |
| NEK11 | 0.747524 | 0.018893 |
| D28359 | 0.747675 | 0.014845 |
| NEK5 | 0.747887 | 0.021592 |
| KIF27 | 0.74818 | 0.009447 |
| DIXDC1 | 0.748442 | 0.006748 |
| DQ586540 | 0.749533 | 0.002699 |
| SPAG6 | 0.752133 | 0.018893 |
| LOC644554 | 0.752591 | 0.005398 |
| PTGFR | 0.753246 | 0.036437 |
| BMI1 | 0.753412 | 0.006748 |
| DAW1 | 0.753861 | 0.033738 |
| ASTN2 | 0.753944 | 0.009447 |
| IFT80 | 0.754508 | 0 |
| WDR65 | 0.754854 | 0.032389 |
| FBXO43 | 0.756192 | 0.020243 |
| CASC2 | 0.757422 | 0.026991 |
| BC049386 | 0.757746 | 0.036437 |
| KANSL1L | 0.758081 | 0 |
| PCDHGA8 | 0.759734 | 0.016194 |

TABLE 2-continued

| Gene | dFC | dFC p |
|---|---|---|
| SLC44A5 | 0.760787 | 0.036437 |
| TTC30B | 0.761599 | 0.00135 |
| TTC26 | 0.762035 | 0.004049 |
| CCDC135 | 0.762347 | 0.02834 |
| LOC100507557 | 0.763482 | 0.009447 |
| PIH1D3 | 0.764247 | 0.031039 |
| AK7 | 0.764436 | 0.012146 |
| RSPH4A | 0.764911 | 0.016194 |
| ADGB | 0.765492 | 0.020243 |
| DNER | 0.76586 | 0.036437 |
| WDR35 | 0.765939 | 0.00135 |
| SYNE1 | 0.767087 | 0.021592 |
| FAM81B | 0.767513 | 0.02834 |
| CNTNAP3 | 0.769537 | 0 |
| FAM81A | 0.770297 | 0.021592 |
| LINC00939 | 0.77042 | 0 |
| CAP2 | 0.771671 | 0.016194 |
| ABCC6P2 | 0.771779 | 0.031039 |
| LAMA2 | 0.772228 | 0.010796 |
| C21orf128 | 0.773994 | 0.022942 |
| VCAN | 0.777167 | 0.018893 |
| FMO6P | 0.777255 | 0.017544 |
| FSIP1 | 0.777635 | 0.013495 |
| ARMC4 | 0.777778 | 0.033738 |
| bpl 41-16 | 0.778201 | 0.047233 |
| CDC14A | 0.779309 | 0.005398 |
| CXorf58 | 0.779326 | 0.025641 |
| LOC541467 | 0.780948 | 0.002699 |
| NME5 | 0.781024 | 0.016194 |
| LCA5 | 0.781141 | 0.009447 |
| ARL6 | 0.782386 | 0.002699 |
| C14orf37 | 0.782871 | 0.006748 |
| RCAN2 | 0.784984 | 0.00135 |
| ROCK1P1 | 0.785052 | 0.010796 |
| MS4A8 | 0.785284 | 0.041835 |
| C10orf107 | 0.785388 | 0.035088 |
| CC2D2A | 0.785577 | 0.005398 |
| UBXN10 | 0.786137 | 0.009447 |
| MYCBPAP | 0.787012 | 0.026991 |
| KIAA0895 | 0.78764 | 0.00135 |
| PIH1D2 | 0.788457 | 0.017544 |
| LOC100505695 | 0.788893 | 0.022942 |
| ABCA13 | 0.789328 | 0.009447 |
| USH2A | 0.789366 | 0.010796 |
| DNAH2 | 0.789614 | 0.024291 |
| IQCH | 0.790285 | 0.013495 |
| CXXC4 | 0.790635 | 0.016194 |
| XK | 0.794371 | 0 |
| ICOS | 0.794757 | 0.008097 |
| CDKL2 | 0.795126 | 0.02834 |
| ZNF273 | 0.795135 | 0.002699 |
| KIAA1377 | 0.797409 | 0.013495 |
| ZC2HC1A | 0.797542 | 0.00135 |
| C12orf75 | 0.800288 | 0.018893 |
| SLC28A2 | 0.800422 | 0.016194 |
| MCMDC2 | 0.801702 | 0.008097 |
| ENO4 | 0.801731 | 0.009447 |
| AQP4-AS1 | 0.80269 | 0.020243 |
| SEC14L3 | 0.803309 | 0.035088 |
| ERBB4 | 0.803669 | 0.02834 |
| KCNN3 | 0.804205 | 0.041835 |
| FAM47E | 0.804636 | 0.021592 |
| MAP3K19 | 0.804743 | 0.010796 |
| ZMYND12 | 0.804869 | 0.026991 |
| SAMD15 | 0.806464 | 0.008097 |
| KAL1 | 0.806745 | 0.006748 |
| KIF6 | 0.808001 | 0.031039 |
| SPEF2 | 0.809363 | 0.013495 |
| PPIL6 | 0.809511 | 0.016194 |
| WDR16 | 0.810957 | 0.036437 |
| LINC00875 | 0.81212 | 0.026991 |
| KLHL13 | 0.812872 | 0.018893 |
| AK091996 | 0.813572 | 0.043185 |
| EPPIN | 0.814107 | 0.045884 |
| STK33 | 0.814359 | 0.02834 |
| PPM1E | 0.814933 | 0.036437 |
| TSPAN2 | 0.815672 | 0.002699 |
| CCDC113 | 0.818224 | 0.004049 |

TABLE 2-continued

| Gene | dFC | dFC p |
|---|---|---|
| SNURF-SNRPN | 0.818423 | 0.010796 |
| BC048113 | 0.820028 | 0.010796 |
| LRP2BP | 0.821356 | 0.006748 |
| LZTFL1 | 0.826552 | 0.00135 |
| MAATS1 | 0.828504 | 0.016194 |
| C8orf37 | 0.831592 | 0.00135 |
| AK055257 | 0.832072 | 0.002699 |
| CCDC89 | 0.832319 | 0.010796 |
| C1orf168 | 0.833105 | 0.012146 |
| CYP24A1 | 0.834221 | 0.024291 |
| ANKRD66 | 0.834402 | 0.022942 |
| KIAA0825 | 0.834566 | 0.00135 |
| PRUNE2 | 0.834716 | 0.014845 |
| CDKL1 | 0.835775 | 0.016194 |
| CCDC176 | 0.836278 | 0.004049 |
| LRRC49 | 0.837866 | 0.010796 |
| ZNF157 | 0.838101 | 0.016194 |
| DYNC2H1 | 0.838336 | 0.016194 |
| CNTNAP2 | 0.838549 | 0.002699 |
| GPR116 | 0.840894 | 0.009447 |
| C7orf63 | 0.840924 | 0.004049 |
| MPDZ | 0.842984 | 0.012146 |
| AX747913 | 0.844466 | 0.012146 |
| RFX3 | 0.844592 | 0.004049 |
| U6__124 | 0.844911 | 0.008097 |
| ARHGAP42 | 0.845017 | 0.002699 |
| KCNE1 | 0.846185 | 0.009447 |
| CEP97 | 0.847895 | 0.005398 |
| ZNF440 | 0.8496 | 0.002699 |
| CNTN5 | 0.850298 | 0.021592 |
| FRMPD2 | 0.850838 | 0.039136 |
| IFLTD1 | 0.85406 | 0.018893 |
| DPY19L2P2 | 0.856219 | 0.005398 |
| KLHL6 | 0.861302 | 0.009447 |
| TMEM67 | 0.861806 | 0.004049 |
| PTPLAD2 | 0.862106 | 0.002699 |
| NUP62CL | 0.862667 | 0.005398 |
| BC022056 | 0.864484 | 0.013495 |
| TOX | 0.865302 | 0.002699 |
| LOC400891 | 0.86554 | 0.024291 |
| FAM181A-AS1 | 0.866059 | 0.022942 |
| ENPP5 | 0.866109 | 0.00135 |
| CCDC39 | 0.867723 | 0.017544 |
| EFHC2 | 0.867761 | 0.005398 |
| SHANK2 | 0.868439 | 0.016194 |
| PZP | 0.869917 | 0.021592 |
| DNAH6 | 0.870832 | 0.017544 |
| DOC2A | 0.871309 | 0.036437 |
| SLC38A4 | 0.873092 | 0.025641 |
| RSPH10B2 | 0.873604 | 0.025641 |
| DNAH12 | 0.87443 | 0.021592 |
| TSPAN11 | 0.874743 | 0.024291 |
| AGBL2 | 0.875209 | 0.012146 |
| ZNF474 | 0.87613 | 0.006748 |
| SIAH3 | 0.879222 | 0.026991 |
| LRRIQ3 | 0.880281 | 0.018893 |
| VWA8-AS1 | 0.880636 | 0.026991 |
| LRRC6 | 0.882575 | 0.006748 |
| MTMR7 | 0.883581 | 0.012146 |
| EFHB | 0.886529 | 0.012146 |
| LOC201651 | 0.887307 | 0.010796 |
| LINGO2 | 0.888144 | 0.005398 |
| CERKL | 0.890268 | 0.005398 |
| C20orf26 | 0.890279 | 0.018893 |
| RP1 | 0.89073 | 0.017544 |
| IL5RA | 0.891766 | 0.002699 |
| ALS2CR12 | 0.893117 | 0.026991 |
| GSTA2 | 0.893173 | 0.037787 |
| LOC100506124 | 0.893248 | 0.010796 |
| 10-Mar | 0.893611 | 0.02834 |
| LDLRAD4 | 0.897846 | 0.00135 |
| RGS22 | 0.898446 | 0.022942 |
| SLC23A1 | 0.898562 | 0.022942 |
| LEKR1 | 0.898766 | 0.006748 |
| LOC100129046 | 0.898932 | 0 |
| TTC18 | 0.899833 | 0.013495 |
| SPATA18 | 0.900262 | 0.002699 |
| DSCAML1 | 0.900868 | 0.031039 |

TABLE 2-continued

| Gene | dFC | dFC p |
|---|---|---|
| CCDC81 | 0.904414 | 0.021592 |
| DCDC5 | 0.90704 | 0.012146 |
| APOBEC4 | 0.907331 | 0.013495 |
| FLJ26850 | 0.910164 | 0.020243 |
| TTLL6 | 0.910466 | 0.025641 |
| PCDP1 | 0.912836 | 0.009447 |
| NWD1 | 0.91384 | 0.010796 |
| PODNL1 | 0.915513 | 0.004049 |
| WDR49 | 0.915818 | 0.005398 |
| WDR63 | 0.916241 | 0.009447 |
| C12orf56 | 0.916564 | 0.004049 |
| IGSF10 | 0.919509 | 0.005398 |
| HSD17B13 | 0.919523 | 0.004049 |
| SERPINI2 | 0.920904 | 0.012146 |
| C3orf30 | 0.923196 | 0.024291 |
| DNMBP-AS1 | 0.923703 | 0.002699 |
| HYDIN | 0.924701 | 0.012146 |
| CXorf30 | 0.926751 | 0.010796 |
| PNMAL1 | 0.927655 | 0.00135 |
| MDH1B | 0.930488 | 0.016194 |
| C2orf73 | 0.931176 | 0.020243 |
| CDHR3 | 0.936346 | 0.017544 |
| PTGER2 | 0.938073 | 0.004049 |
| MYLK3 | 0.93892 | 0.010796 |
| C10orf111 | 0.941304 | 0.010796 |
| SNURF | 0.941953 | 0.017544 |
| GRM7 | 0.943591 | 0.012146 |
| DUSP19 | 0.943934 | 0.00135 |
| NEK10 | 0.943943 | 0.005398 |
| VWA3B | 0.94481 | 0.010796 |
| ARMC3 | 0.945204 | 0.008097 |
| ABCD2 | 0.947039 | 0.005398 |
| ACSBG1 | 0.949202 | 0.017544 |
| ARMC2 | 0.950676 | 0.005398 |
| UNC79 | 0.95186 | 0.008097 |
| NELL2 | 0.952218 | 0.013495 |
| ANKUB1 | 0.954487 | 0.013495 |
| C11orf53 | 0.958001 | 0.012146 |
| SPATA4 | 0.960678 | 0.020243 |
| RPGRIP1L | 0.961152 | 0.00135 |
| DCDC1 | 0.962302 | 0.017544 |
| EFCAB10 | 0.966814 | 0.012146 |
| DNAH9 | 0.968475 | 0.013495 |
| TTLL7 | 0.968901 | 0.00135 |
| FAM182A | 0.971171 | 0.017544 |
| BC043205 | 0.971869 | 0.008097 |
| PPP1R42 | 0.972081 | 0.024291 |
| TCTEX1D1 | 0.974089 | 0.012146 |
| C6orf118 | 0.9771 | 0.008097 |
| EFCAB6 | 0.978745 | 0.005398 |
| DNAH11 | 0.980118 | 0.016194 |
| FAM154B | 0.980136 | 0.005398 |
| DNAH3 | 0.991559 | 0.004049 |
| DNAH10 | 0.998643 | 0.009447 |
| C6orf165 | 1.001436 | 0.009447 |
| ARHGEF33 | 1.003806 | 0.002699 |
| LOC157381 | 1.003953 | 0.013495 |
| ARHGEF26-AS1 | 1.004811 | 0.022942 |
| IQUB | 1.006529 | 0.004049 |
| WDR78 | 1.009707 | 0.005398 |
| CNTD1 | 1.009943 | 0.022942 |
| TEX21P | 1.019337 | 0.002699 |
| REEP1 | 1.020003 | 0.009447 |
| RBM24 | 1.021454 | 0.005398 |
| TMEM212 | 1.022746 | 0.012146 |
| TEX9 | 1.02687 | 0.00135 |
| DIO1 | 1.027586 | 0.013495 |
| ECT2L | 1.040185 | 0.016194 |
| GCNT4 | 1.044235 | 0 |
| FSD1L | 1.0449 | 0.008097 |
| MAMDC2 | 1.047457 | 0.002699 |
| LOC100499484-C9ORF174 | 1.049135 | 0 |
| ADH6 | 1.053445 | 0.017544 |
| LOC653501 | 1.054765 | 0.02834 |
| DNAH7 | 1.056027 | 0.002699 |
| DCDC2 | 1.06403 | 0.009447 |
| KLHL32 | 1.064365 | 0.010796 |
| PTGES3L | 1.066132 | 0.009447 |
| ADAM22 | 1.06762 | 0.006748 |
| AKAP6 | 1.069579 | 0.00135 |
| TEX26 | 1.072918 | 0.008097 |
| DPY19L2 | 1.074651 | 0.004049 |
| ZBBX | 1.075896 | 0.005398 |
| TXLNB | 1.076086 | 0.00135 |
| ANKFN1 | 1.081575 | 0.005398 |
| CHDC2 | 1.081988 | 0.006748 |
| CRISPLD1 | 1.082421 | 0.00135 |
| WDR96 | 1.082856 | 0.008097 |
| FAM216B | 1.090764 | 0.002699 |
| AK057689 | 1.092907 | 0.009447 |
| TSPAN19 | 1.096467 | 0.010796 |
| DTHD1 | 1.099107 | 0.002699 |
| PROS1 | 1.099654 | 0.008097 |
| DNAH5 | 1.102161 | 0.009447 |
| AX747851 | 1.111707 | 0.002699 |
| MYLK | 1.11338 | 0.004049 |
| AK090700 | 1.121972 | 0.005398 |
| SRD5A2 | 1.132639 | 0.005398 |
| ANGPTL5 | 1.154942 | 0.010796 |
| TMEM232 | 1.155885 | 0.006748 |
| CXorf22 | 1.164025 | 0.002699 |
| AK097702 | 1.166566 | 0.00135 |
| AK310634 | 1.169666 | 0.02834 |
| C1orf141 | 1.171093 | 0.004049 |
| BICC1 | 1.183205 | 0.014845 |
| FAM86B2 | 1.197834 | 0.017544 |
| AX747150 | 1.200255 | 0.036437 |
| PCDHB1 | 1.206511 | 0.002699 |
| CAPS2 | 1.212587 | 0.00135 |
| PTPN20B | 1.214769 | 0.002699 |
| TCP11X2 | 1.216188 | 0.008097 |
| GIPC2 | 1.221175 | 0.004049 |
| GRM5 | 1.223106 | 0.006748 |
| LOC100130451 | 1.231193 | 0.014845 |
| C12orf63 | 1.244937 | 0.00135 |
| FLJ00322 | 1.275442 | 0.010796 |
| MTTP | 1.286762 | 0.002699 |
| MROH9 | 1.288778 | 0.004049 |
| SLC16A12 | 1.300744 | 0.004049 |
| AK307870 | 1.306822 | 0.036437 |
| MYCT1 | 1.414562 | 0.009447 |
| AK094325 | 1.490331 | 0.008097 |
| AX747187 | 1.558281 | 0.00135 |
| FGF14 | 1.626259 | 0.010796 |
| PHOSPHO2-KLHL23 | 1.746327 | 0.022942 |
| CD200R1L | 1.751099 | 0.013495 |
| AK126334 | 1.813924 | 0.00135 |
| PALM2-AKAP2 | 1.927757 | 0.039136 |
| LY75-CD302 | 2.064397 | 0.024291 |

The NEC cat allergy gene signature was significantly reversed by REGN1908-1909 relative to placebo (NES=−2.48, p<0.001). A list of the top 76 genes associated with treatment using stricter thresholds (|FC|>2, p<0.05) is shown in Table 3.

TABLE 3

| Gene | dFC | dFC p |
|---|---|---|
| BC007880 | −3.34157 | 0.016194 |
| BC080587 | −2.65396 | 0.012146 |
| BX537909 | −1.44076 | 0.020243 |
| NGS-17 | −1.2322 | 0.006748 |
| LOC100862671 | −1.12885 | 0.025641 |
| AX747215 | −1.12384 | 0 |
| P2RX1 | −1.10492 | 0.041835 |
| SDS | −1.08107 | 0.005398 |
| S1PR4 | −1.06007 | 0.049933 |
| RPPH1 | −1.05422 | 0.021592 |
| ARPC4-TTLL3 | −1.05186 | 0.036437 |
| SERPING1 | −1.01 | 0.049933 |

TABLE 3-continued

| Gene | dFC | dFC p |
|---|---|---|
| C6orf165 | 1.001436 | 0.009447 |
| ARHGEF33 | 1.003806 | 0.002699 |
| LOC157381 | 1.003953 | 0.013495 |
| ARHGEF26-AS1 | 1.004811 | 0.022942 |
| IQUB | 1.006529 | 0.004049 |
| WDR78 | 1.009707 | 0.005398 |
| CNTD1 | 1.009943 | 0.022942 |
| TEX21P | 1.019337 | 0.002699 |
| REEP1 | 1.020003 | 0.009447 |
| RBM24 | 1.021454 | 0.005398 |
| TMEM212 | 1.022746 | 0.012146 |
| TEX9 | 1.02687 | 0.00135 |
| DIO1 | 1.027586 | 0.013495 |
| ECT2L | 1.040185 | 0.016194 |
| GCNT4 | 1.044235 | 0 |
| FSD1L | 1.0449 | 0.008097 |
| MAMDC2 | 1.047457 | 0.002699 |
| LOC100499484-C9ORF174 | 1.049135 | 0 |
| ADH6 | 1.053445 | 0.017544 |
| LOC653501 | 1.054765 | 0.02834 |
| DNAH7 | 1.056027 | 0.002699 |
| DCDC2 | 1.06403 | 0.009447 |
| KLHL32 | 1.064365 | 0.010796 |
| PTGES3L | 1.066132 | 0.009447 |
| ADAM22 | 1.06762 | 0.006748 |
| AKAP6 | 1.069579 | 0.00135 |
| TEX26 | 1.072918 | 0.008097 |
| DPY19L2 | 1.074651 | 0.004049 |
| ZBBX | 1.075896 | 0.005398 |
| TXLNB | 1.076086 | 0.00135 |
| ANKFN1 | 1.081575 | 0.005398 |
| CHDC2 | 1.081988 | 0.006748 |
| CRISPLD1 | 1.082421 | 0.00135 |
| WDR96 | 1.082856 | 0.008097 |
| FAM216B | 1.090764 | 0.002699 |
| AK057689 | 1.092907 | 0.009447 |
| TSPAN19 | 1.096467 | 0.010796 |
| DTHD1 | 1.099107 | 0.002699 |
| PROS1 | 1.099654 | 0.008097 |
| DNAH5 | 1.102161 | 0.009447 |
| AX747851 | 1.111707 | 0.002699 |
| MYLK | 1.11338 | 0.004049 |
| AK090700 | 1.121972 | 0.005398 |
| SRD5A2 | 1.132639 | 0.005398 |
| ANGPTL5 | 1.154942 | 0.010796 |
| TMEM232 | 1.155885 | 0.006748 |
| CXorf22 | 1.164025 | 0.002699 |
| AK097702 | 1.166566 | 0.00135 |
| AK310634 | 1.169666 | 0.02834 |
| C1orf141 | 1.171093 | 0.004049 |
| BICC1 | 1.183205 | 0.014845 |
| FAM86B2 | 1.197834 | 0.017544 |
| AX747150 | 1.200255 | 0.036437 |
| PCDHB1 | 1.206511 | 0.002699 |
| CAPS2 | 1.212587 | 0.00135 |
| PTPN20B | 1.214769 | 0.002699 |
| TCP11X2 | 1.216188 | 0.008097 |
| GIPC2 | 1.221175 | 0.004049 |
| GRM5 | 1.223106 | 0.006748 |
| LOC100130451 | 1.231193 | 0.014845 |
| C12orf63 | 1.244937 | 0.00135 |
| FLJ00322 | 1.275442 | 0.010796 |
| MTTP | 1.286762 | 0.002699 |
| MROH9 | 1.288778 | 0.004049 |
| SLC16A12 | 1.300744 | 0.004049 |
| AK307870 | 1.306822 | 0.036437 |
| MYCT1 | 1.414562 | 0.009447 |
| AK094325 | 1.490331 | 0.008097 |
| AX747187 | 1.558281 | 0.00135 |
| FGF14 | 1.626259 | 0.010796 |
| PHOSPHO2-KLHL23 | 1.746327 | 0.022942 |
| CD200R1L | 1.751099 | 0.013495 |
| AK126334 | 1.813924 | 0.00135 |
| PALM2-AKAP2 | 1.927757 | 0.039136 |
| LY75-CD302 | 2.064397 | 0.024291 |

Example 4: Fel d 1 Monoclonal Antibody Combination Modulates Asthma and Allergic Molecular Pathways in Nasal Mucosa Upon Cat Allergen Challenge in a Phase 2, Randomized, Double-Blind, Placebo-Controlled Study A single dose of Fel d 1 monoclonal antibodies (REGN1908/1909) was evaluated for the prevention of early asthma responses (EAR) by cat allergen in cat-allergic mild asthmatic subjects. FIG. 1, Panel A shows a representative overview of a validated EEU used as a challenge model to evaluate the effectiveness of REGN1908/1909 to inhibit cat allergen-provoked asthma exacerbations in cat-allergic mild asthmatics. In brief, cat-allergic subjects with mild asthma were randomized to single-dose s.c. REGN1908/1909 600 mg (n=29) or placebo (n=27) prior to cat-allergen exposure in a controlled EEU. Forced expiratory volume in 1 second (FEV1) was measured every 10 minutes up to 4 hours during cat-allergen exposures at baseline, and on Days 8, 29, 57, and 85. Subjects were exposed to cat allergen in the EEU for a maximum of 4 hours or until they reached an EAR, defined as ≥20% reduction in FEV1 from baseline. After each cat-allergen challenge in the EEU, participants left the site with a rescue treatment kit containing short acting beta 2 agonists, oral corticosteroids, and oral antihistamines. Nasal brushings were performed approximately 6 hours after the start of the EEU at two timepoints: once during the screening visit prior to study drug administration, and once on Day 29 after study drug administration. FIG. 1, Panel B shows a representative overview of a 1703 FelD1 study design and sample. Blocks designated A, B, C, and D represent patients at various states of the treatment process. FIG. 1, Panel C shows a representative integration of Blocks A, B, C, and D (from Panel B) into the representative overview of a validated EEU (from Panel A).

Figure 2:
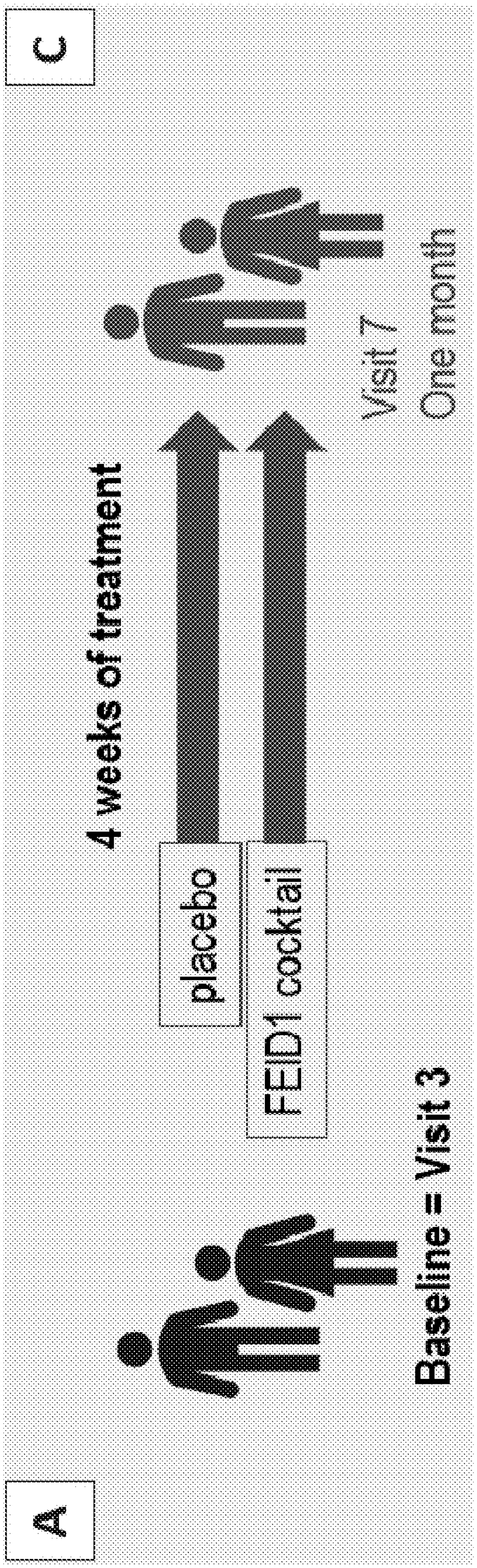
FIG. 2, Panel A shows a depiction of a first comparison between the transcriptomes from cat allergic subjects before allergen exposure and treatment (cat allergic patients without allergen exposure; Block A) vs. transcriptomes from cat allergic subjects on treatment after repeated exposures to allergen (Block C).
Figure 2:
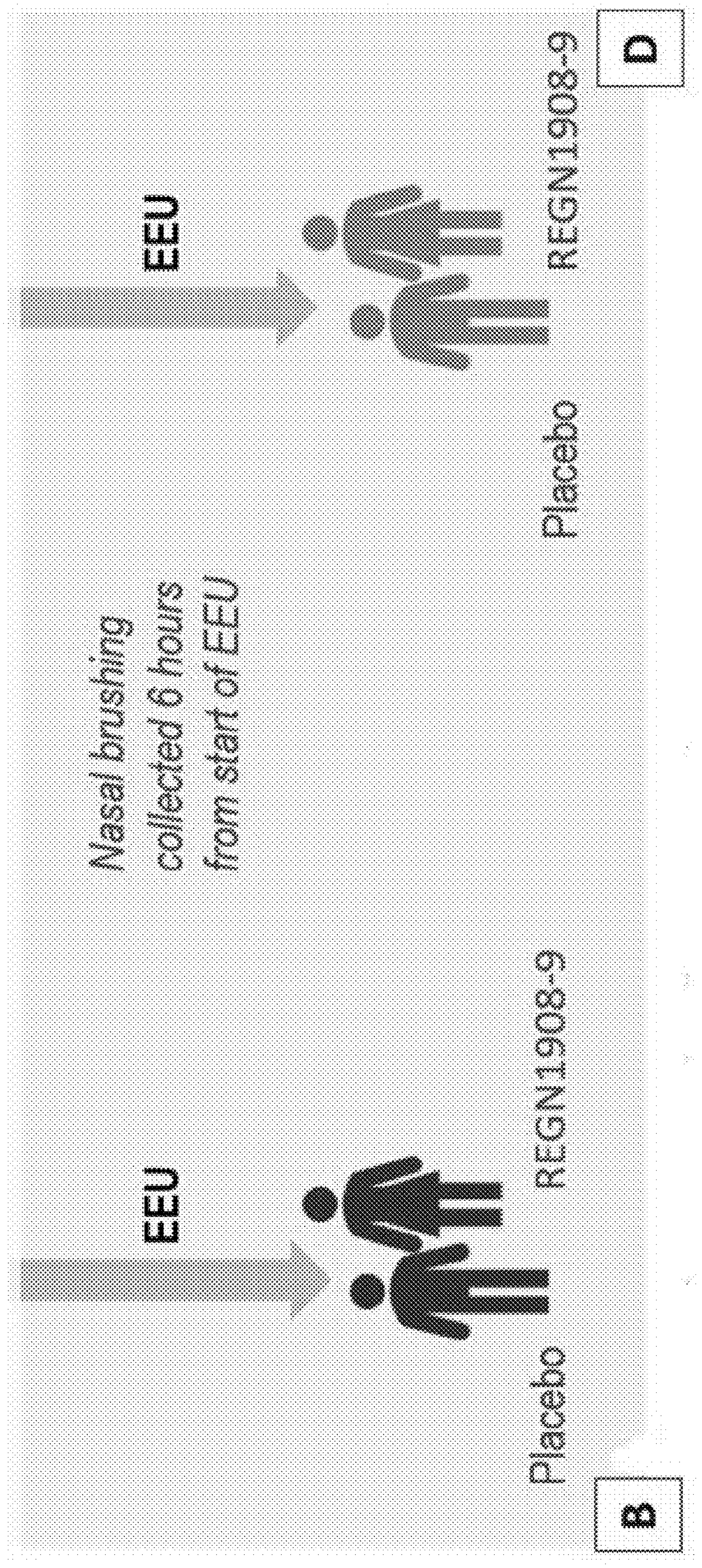

Of particular interest are two comparisons within the treatment procedure. The first comparison (Comparison #1—Block A vs Block C; see, FIG. 2, Panel A) involves a comparison between the transcriptomes from cat allergic subjects before allergen exposure and treatment (cat allergic patients without allergen exposure; Block A) vs. transcriptomes from cat allergic subjects on treatment after repeated exposures to allergen (Block C). For Block A (baseline), there has been no allergen exposure and no treatment. For Block C (one month), there have been two rounds of previous allergen exposure from weeks earlier (baseline, week 1) and 4 weeks of treatment. It was queried whether treatment normalizes the response to cat allergen. The second comparison (Comparison #2—Block B vs Block D; see, FIG. 2, Panel B) involves a comparison between the transcriptomes from subjects exposed to cat allergen before treatment (Block B) and after treatment (Block D). For Block B (baseline), there has been recent allergen exposure (sample taken 6 hrs after start of EEU) and no treatment. For Block D (one month), there have been two rounds of previous allergen exposure from weeks earlier (baseline, week 1) as well as recent allergen exposure (sample taken 6 hrs after start of EEU), and 4 weeks of treatment. It was queried whether treatment reduces immediate immune response to allergen exposure.

Comparison #1—Block A vs Block C

Figure 3:
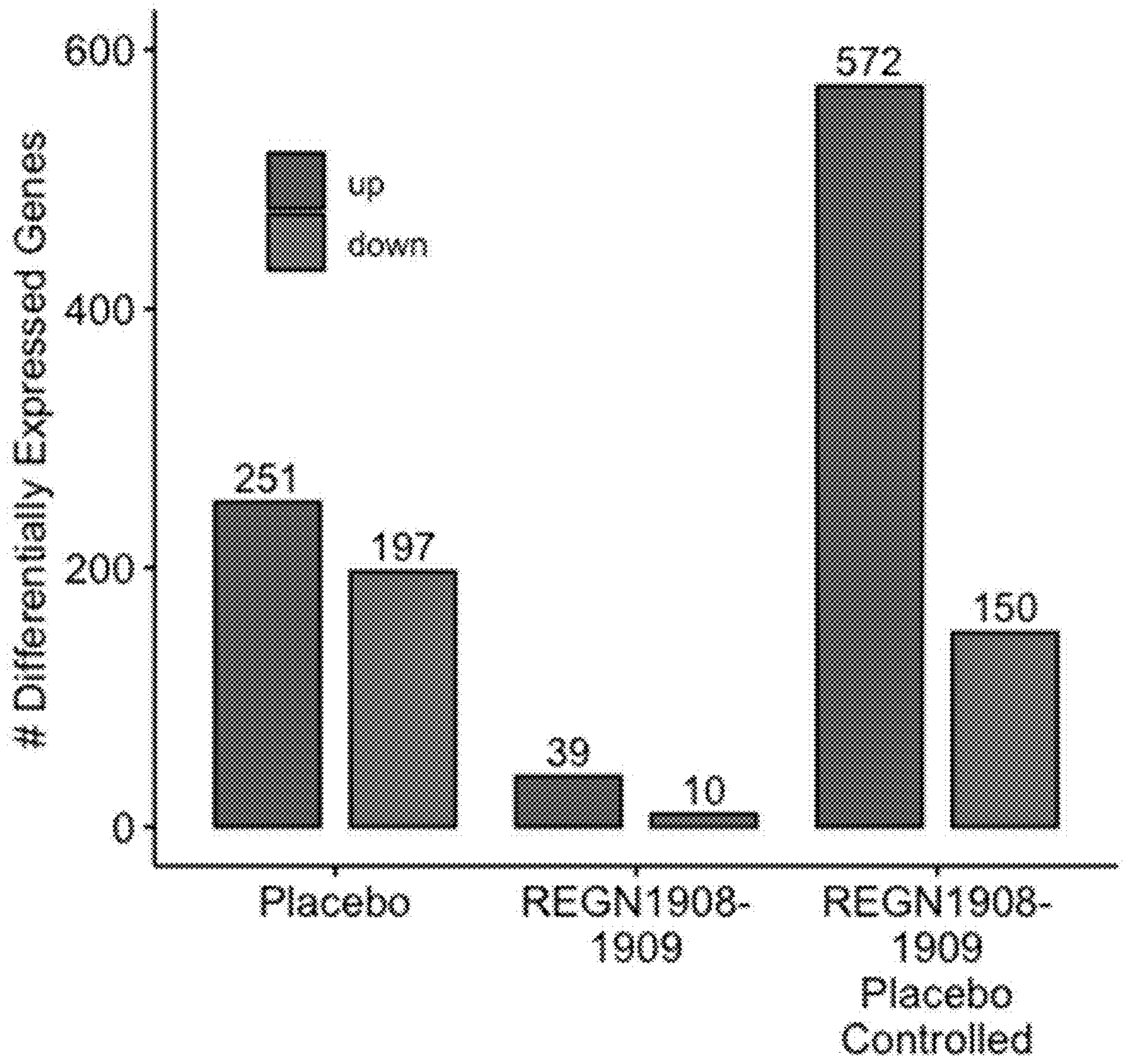
FIG. 3, Panel A, Panel B, and Panel C show results of the first comparison between the transcriptomes from cat allergic subjects before allergen exposure and treatment (cat allergic patients without allergen exposure; Block A) vs. transcriptomes from cat allergic subjects on treatment after repeated exposures to allergen (Block C).
Figure 3:
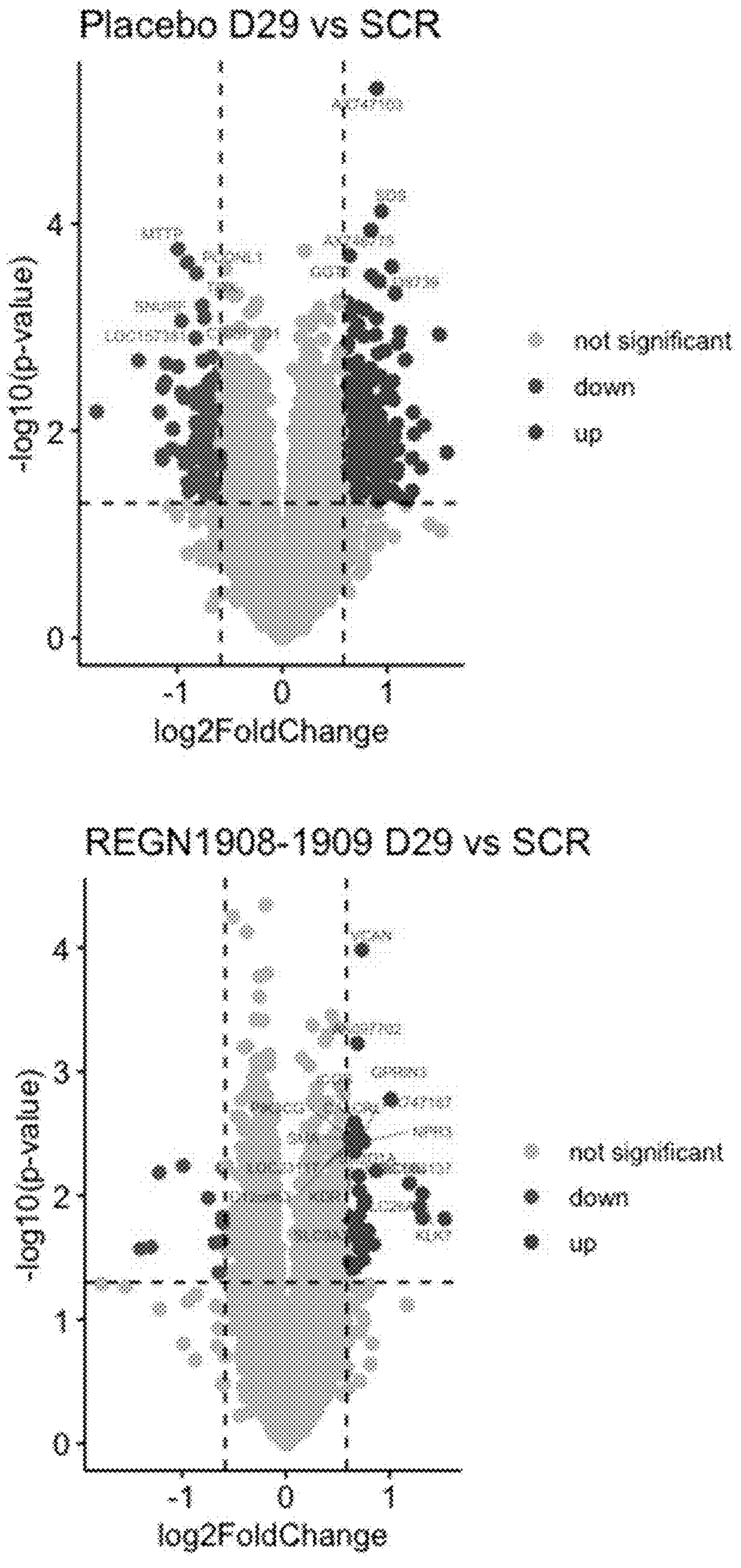
Figure 3:
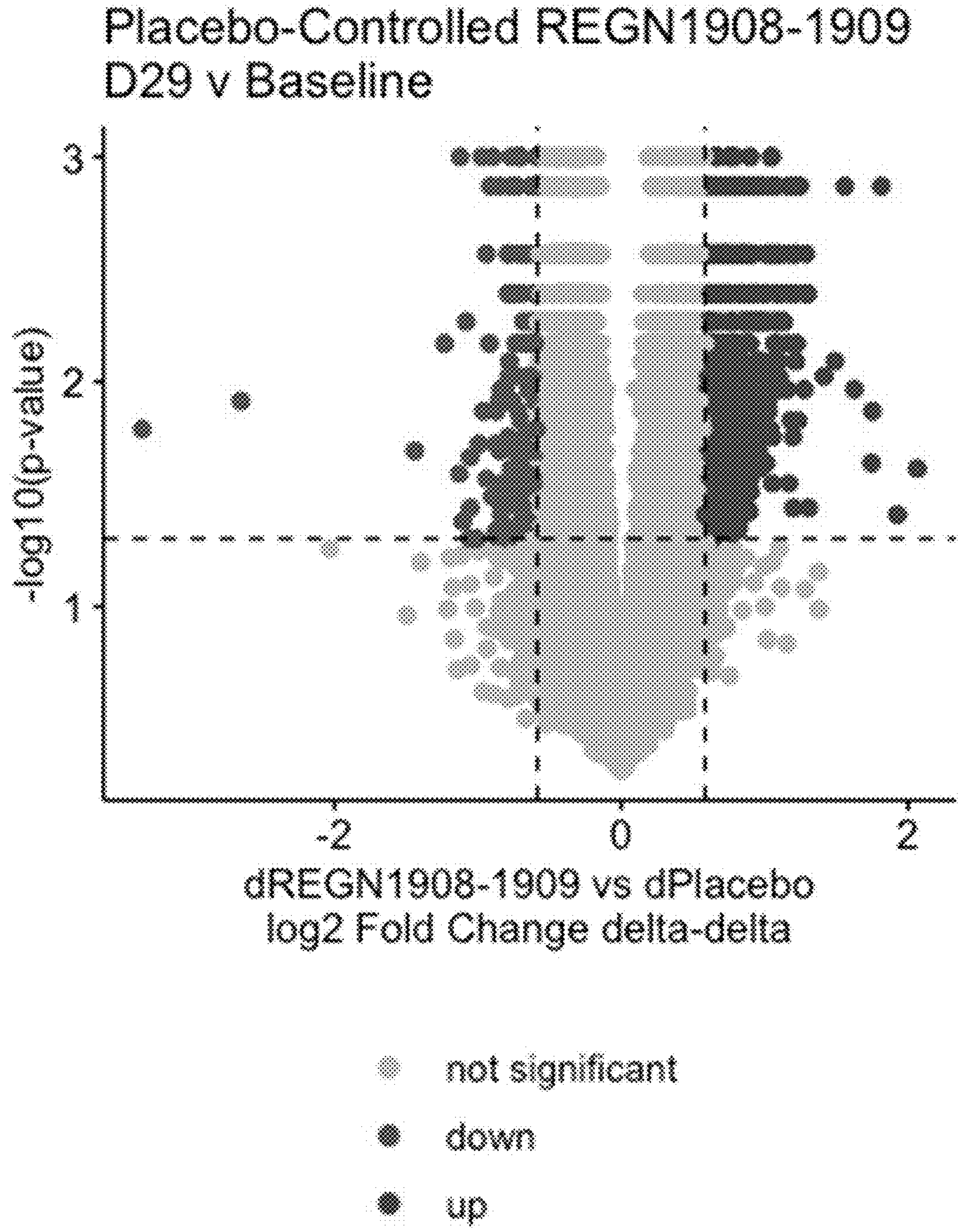

The results of the first comparison (Comparison #1—Block A vs Block C; see, FIG. 2, Panel A) are depicted in FIG. 3, Panel A, Panel B, and Panel C. Regarding differentially expressed genes, for treatment, placebo signatures, nominally significant genes are shown using $|FC|>1.5$, $p<0.05$. Placebo-controlled signature was identified using dFC analysis. REGN1908-1909 suppressed molecular transcriptional changes associated with allergy and asthma in the nasal tissue.

REGN1908/1909 significantly prevented EAR incidence versus placebo on days 8 (48.3% vs 81.5%), 29 (44.8% vs 88.0%), 57 (55.6% vs 76.9%) and 85 (50.0% vs 87.5%) ($P<0.05$ for all except day 57). REGN1908-1909 suppressed molecular transcriptional changes associated with allergy and asthma in the nasal tissue. At the molecular level, placebo-controlled changes in gene expression were observed relating to downregulation of key asthma and allergic pathways, including mast cell activation, type 1 and 2 inflammatory pathways, inflammatory cell migration, and epithelial cell integrity. Using placebo-controlled gene set enrichment analysis (GSEA), Fel d 1 treatment significantly downregulated nasal mucosal derived type 2 asthma signatures (NES=−1.67, q=0.003), in addition to an epithelial asthma gene signature (NES=−2.23, q<0.001). The data presented herein demonstrate: i) the NEC cat allergy gene signature is significantly suppressed by REGN1908-1909 relative to placebo; and ii) asthma signatures (such as, for example Type 2 asthma) are significantly reversed by REGN1908-1909 relative to placebo.

Comparison #2—Block B vs Block D

Figure 4:
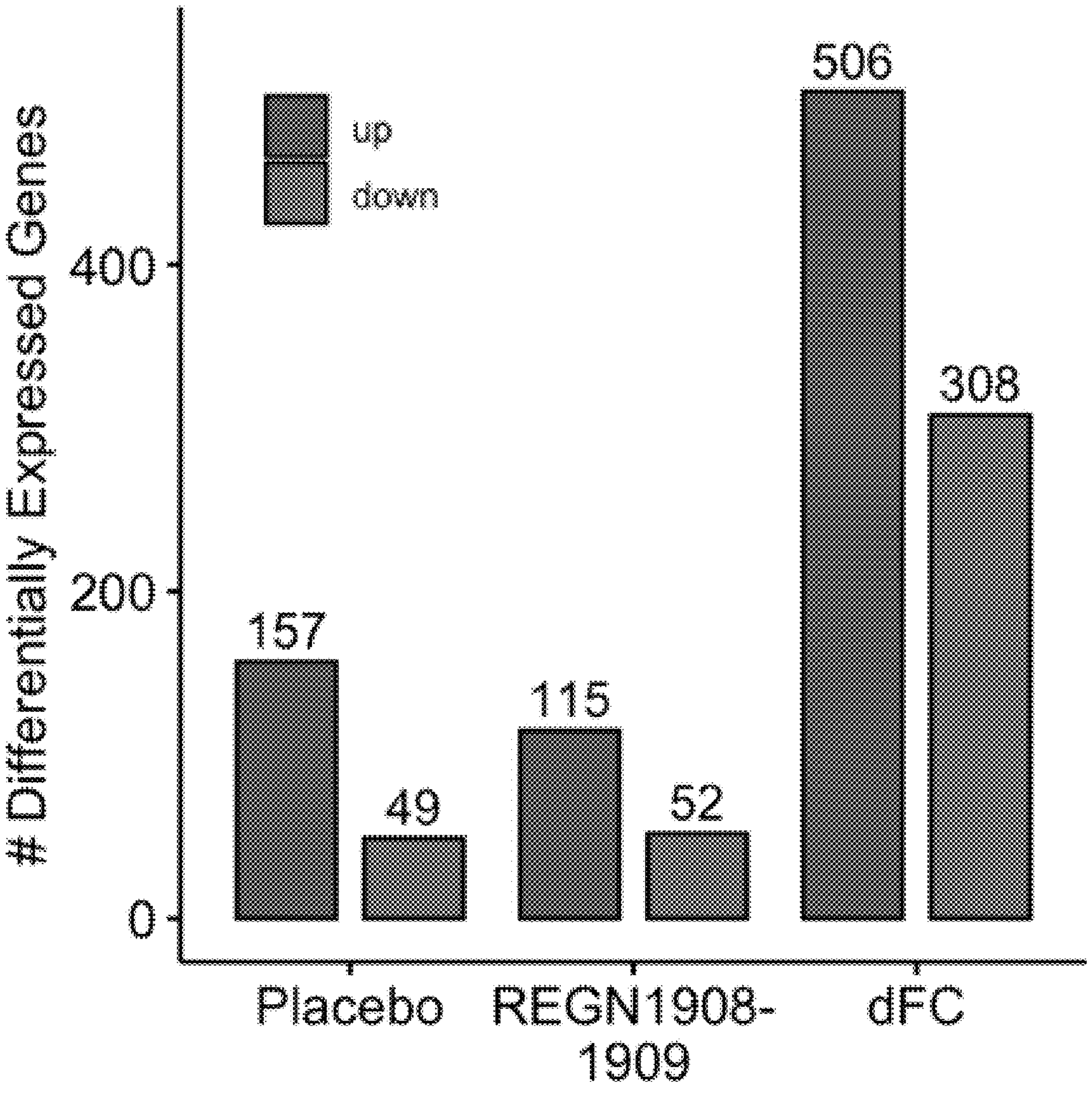
FIG. 4, Panel A, Panel B, and Panel C show results of the second comparison between the transcriptomes from subjects exposed to cat allergen before treatment (Block B) and after treatment (Block D).
Figure 4:
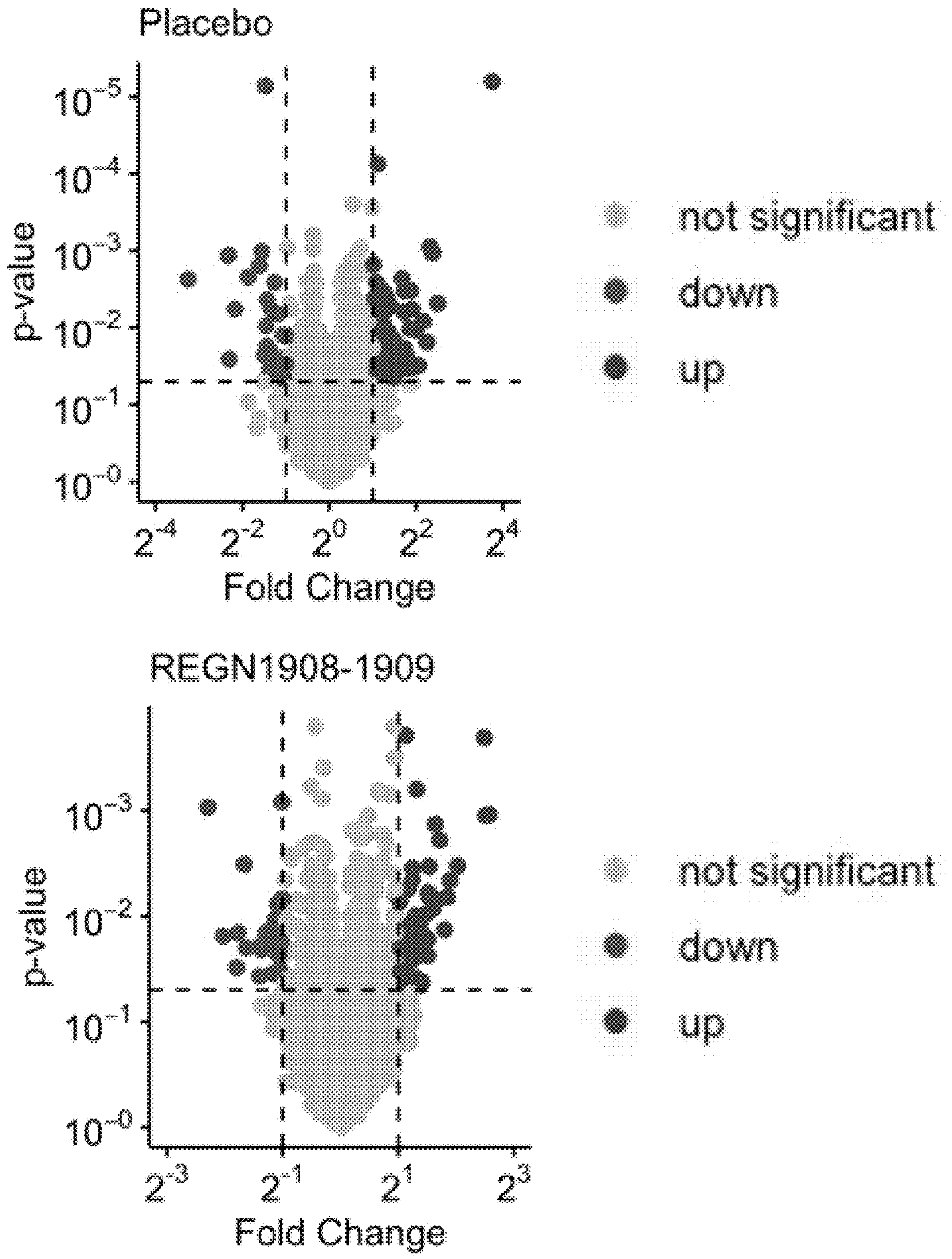
Figure 4:
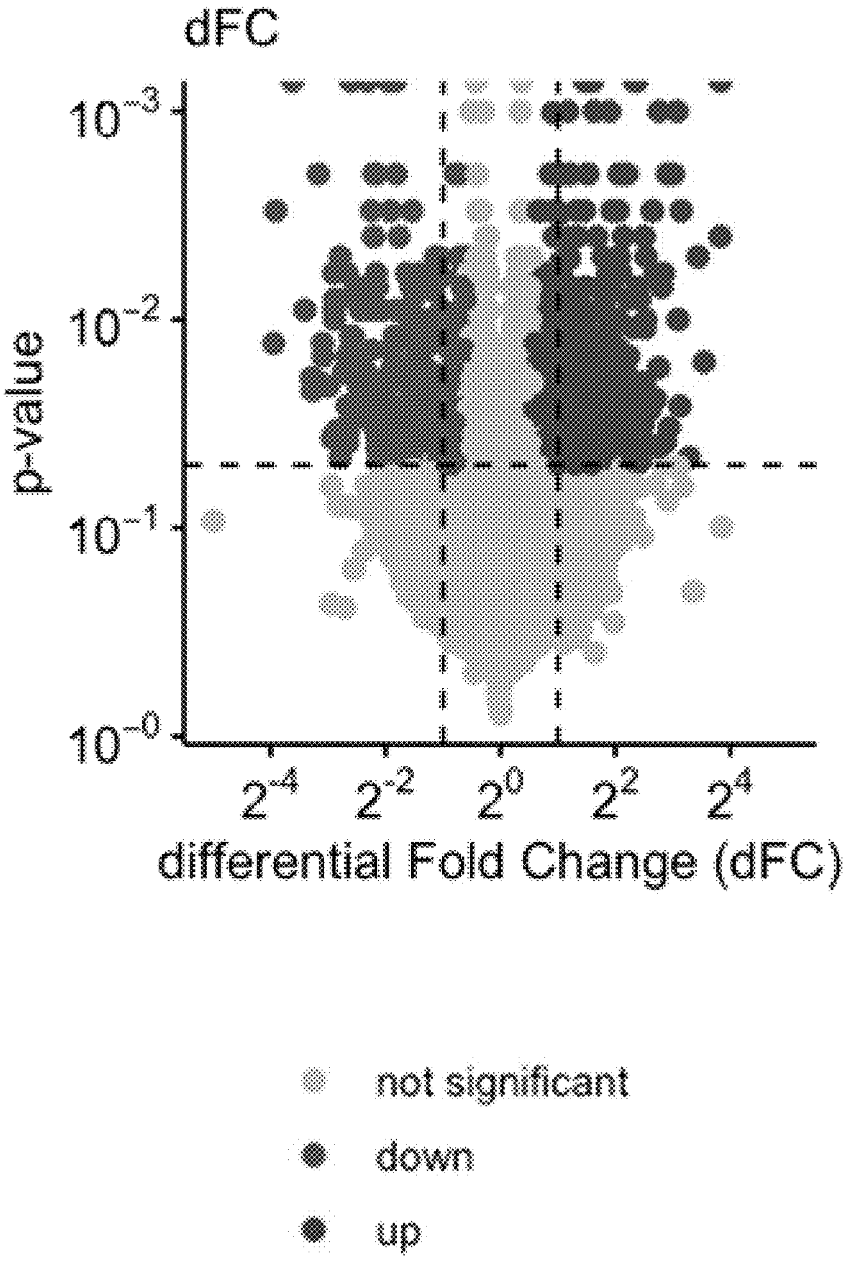

The results of the second comparison (Comparison #2—Block B vs Block D; see, FIG. 2, Panel B) are depicted in FIG. 4, Panel A, Panel B, and Panel C, and Table 4. Regarding differentially expressed genes, for treatment, placebo signatures, nominally significant genes are shown using $|FC|>1.5$, $p<0.05$. Placebo-controlled signature was identified using dFC analysis. REGN1908-1909 suppressed molecular transcriptional changes associated with allergy and asthma in the nasal tissue.

TABLE 4

| GeneID | log2FoldChange Placebo | log2FoldChange REGN1908-1909 | post EEU dFC | post EEU dFC p-value |
|---|---|---|---|---|
| LOC100132062 | 7.566896584 | −1.414190794 | −8.9810874 | 0.0065 |
| CCL8 | 7.554157362 | 0.611702177 | −6.9424552 | 0.0414 |
| AK128563 | 7.203544806 | 0.613784145 | −6.5897607 | 0.0418 |
| BC048201 | 2.008799269 | −1.935654512 | −3.9444538 | 0.0081 |
| LOC100133669 | 2.490131374 | −1.420221812 | −3.9103532 | 0.0026 |
| IL17D | 2.938274066 | −0.682068464 | −3.6203425 | 6.00E−04 |
| RGS13 | 2.096897249 | −1.307919248 | −3.4048165 | 0.0064 |
| DKFZp434J0226 | 1.505200296 | −1.778622361 | −3.2838227 | 0.016 |
| PMF1-BGLAP | 3.473197118 | 0.202166296 | −3.2710308 | 0.0218 |
| LOC643802 | 1.17088752 | −1.995427209 | −3.1663147 | 0.0021 |
| AK123177 | 1.561799414 | −1.586082674 | −3.1478821 | 0.022 |
| SPP1 | 2.867047926 | −0.22621339 | −3.0932613 | 0.0094 |
| BC041030 | 0.941153799 | −2.142782094 | −3.0839359 | 0.0129 |
| AK001975 | 1.252828062 | −1.737533421 | −2.9903615 | 0.0202 |
| THBS4 | 2.204025681 | −0.728736467 | −2.9327621 | 0.0272 |
| BC047364 | 0.630766106 | −2.270690592 | −2.9014567 | 0.006 |
| CNGB3 | 2.411908962 | −0.482257707 | −2.8941667 | 0.0048 |
| FAM27C | 1.921901783 | −0.966041171 | −2.887943 | 0.0075 |
| SRMS | 1.370404031 | −1.515404067 | −2.8858081 | 0.0042 |
| CXCL13 | 2.138645148 | −0.706107206 | −2.8447524 | 0.0325 |
| COL22A1 | 2.750949932 | −0.05414161 | −2.8050915 | 0.0072 |
| BC064137 | 2.116307381 | −0.673829292 | −2.7901367 | 0.0387 |
| AK055853 | 0.848395556 | −1.939165349 | −2.7875609 | 0.0039 |
| OCLM | 2.551967669 | −0.179719192 | −2.7316869 | 0.0144 |
| PSORS1C2 | 0.633859991 | −2.036083647 | −2.6699436 | 0.0209 |
| AX746492 | 1.263166323 | −1.406545848 | −2.6697122 | 0.0143 |
| KCNA7 | 1.136105293 | −1.531423388 | −2.6675287 | 0.0044 |
| EFCAB3 | 1.942922053 | −0.716682976 | −2.659605 | 0.0324 |
| NCAM1 | 3.029718496 | 0.372797333 | −2.6569212 | 0.0378 |
| PRR5-ARHGAP8 | 1.275203249 | −1.371750931 | −2.6469542 | 0.0305 |
| CNDP1 | 1.820682857 | −0.790901486 | −2.6115843 | 0.0162 |
| MSI1 | 1.714450432 | −0.89295588 | −2.6074063 | 0.0108 |
| BX648826 | 1.909529992 | −0.695369075 | −2.6048991 | 0.0014 |
| GFRA3 | 1.420278251 | −1.147233427 | −2.5675117 | 0.0171 |
| DACT1 | 2.295119948 | −0.229014991 | −2.5241349 | 0.0071 |
| AX748314 | 1.515790044 | −0.972800648 | −2.4885907 | 0.0158 |
| CNN1 | 1.575658383 | −0.891878993 | −2.4675374 | 0.0121 |
| BC107108 | 2.545058101 | 0.081666752 | −2.4633913 | 0.0056 |
| PCP2 | 1.636591223 | −0.822390389 | −2.4589816 | 0.028 |
| LRRC63 | 1.576181055 | −0.879885158 | −2.4560662 | 0.0208 |
| SNAP25-AS1 | 1.779522188 | −0.666675336 | −2.4461975 | 0.0091 |
| ESYT3 | 1.06837731 | −1.349006166 | −2.4173835 | 0.0129 |
| HIST1H1D | 0.63044886 | −1.727963063 | −2.3584119 | 0.0293 |
| AK129879 | 0.951807644 | −1.40568614 | −2.3574938 | 0.0242 |
| CASQ2 | 0.480426236 | −1.8661289 | −2.3465551 | 0.0207 |
| SLC16A10 | 0.573711535 | −1.760780852 | −2.3344924 | 0.0157 |
| CRISP3 | 0.470180391 | −1.859746377 | −2.3299268 | 0.036 |
| KIAA0931 | 1.479929385 | −0.836195542 | −2.3161249 | 0.0018 |
| DQ588114 | 0.432442806 | −1.874151683 | −2.3065945 | 0.012 |
| AX747628 | 0.602921009 | −1.682880537 | −2.2858015 | 0.0223 |
| AK022787 | 1.282994278 | −0.987400929 | −2.2703952 | 0.0187 |
| GFRA1 | 1.385089712 | −0.88339804 | −2.2684878 | 0.0215 |
| LIN7A | 1.290655936 | −0.954497156 | −2.2451531 | 0.0035 |
| OXER1 | 2.733406293 | 0.49218595 | −2.2412203 | 0.0153 |
| LILRA5 | 0.944705021 | −1.275190533 | −2.2198956 | 0.0209 |

TABLE 4-continued

| GeneID | log2FoldChange Placebo | log2FoldChange REGN1908-1909 | post EEU dFC | post EEU dFC p-value |
|---|---|---|---|---|
| AX748175 | 1.268221488 | −0.950004553 | −2.218226 | 0.0054 |
| AK125412 | 1.872627934 | −0.343369005 | −2.2159969 | 0.004 |
| LHFPL5 | 1.160047318 | −1.046854974 | −2.2069023 | 0.00190057 |
| PTPLA | 0.853487125 | −1.351980546 | −2.2054677 | 0.0051 |
| AX748417 | 1.235142387 | −0.95435767 | −2.1895001 | 0.0096 |
| AF119915 | 1.914322056 | −0.273324534 | −2.1876466 | 0.0242 |
| EMX2 | 1.18684566 | −0.978863902 | −2.1657096 | 0.0385 |
| PCDHGC4 | 1.246791217 | −0.912702132 | −2.1594933 | 0.006 |
| SEPT12 | 0.911887065 | −1.240347905 | −2.152235 | 0.0021 |
| BPIFB4 | 0.391994936 | −1.752046611 | −2.1440415 | 0.0448 |
| CILP | 1.240925433 | −0.901147069 | −2.1420725 | 0.0071 |
| ADAMTS1 | 0.763025027 | −1.37649549 | −2.1395205 | 0.0368 |
| BHMT2 | 2.389593791 | 0.250599735 | −2.1389941 | 0.039 |
| LINC00937 | 2.321453617 | 0.185751337 | −2.1357023 | 0.0339 |
| AX747864 | 1.769033821 | −0.345879513 | −2.1149133 | 0.0364 |
| TLDC2 | 1.337426732 | −0.772331466 | −2.1097582 | 0.0247 |
| BMP6 | 1.120194758 | −0.983369455 | −2.1035642 | 0.0426 |
| MMP9 | 1.772431722 | −0.293536816 | −2.0659685 | 0.0189 |
| MAP1LC3C | 1.630291874 | −0.43367465 | −2.0639665 | 0.0113 |
| MSRB3 | 1.5899018 | −0.467312182 | −2.057214 | 0.0103 |
| AK095583 | 1.928572401 | −0.116283442 | −2.0448558 | 0.0423 |
| LOC729444 | 1.277496685 | −0.747523722 | −2.0250204 | 0.0362 |
| DQ599872_2 | 1.912561089 | −0.107897123 | −2.0204582 | 0.0346 |
| MAGOH2 | 1.581881959 | −0.428532645 | −2.0104146 | 0.029 |
| BC041484 | 0.892818555 | −1.078834514 | −1.9716531 | 0.0199 |
| TTYH1 | 1.2183859 | −0.751296191 | −1.9696821 | 0.0191 |
| PLA2G4E | 1.173516119 | −0.782389059 | −1.9559052 | 0.0307 |
| PDE1B | 1.475409872 | −0.478001751 | −1.9534116 | 0.0018 |
| CCR3 | 1.007410775 | −0.943947812 | −1.9513586 | 0.0306 |
| C22orf26 | 0.952313938 | −0.996728868 | −1.9490428 | 0.0426 |
| NAT2 | 2.028669409 | 0.086170557 | −1.9424989 | 0.0341 |
| AK125288 | 0.400433807 | −1.531302517 | −1.9317363 | 0.0444 |
| DPEP3 | 0.939244183 | −0.97170299 | −1.9109472 | 0.0137 |
| EDA2R | 1.751114443 | −0.158342946 | −1.9094574 | 0.0041 |
| PYHIN1 | 1.731384423 | −0.174167352 | −1.9055518 | 0.0425 |
| CYSLTR2 | 1.389059453 | −0.513477125 | −1.9025366 | 0.0485 |
| GPR83 | 1.375379085 | −0.518130157 | −1.8935092 | 0.0207 |
| AX746564_2 | 0.483076725 | −1.40717364 | −1.8902504 | 0.0344 |
| SMIM1 | 0.864274773 | −1.02140796 | −1.8856827 | 0.0158 |
| AK311167 | 1.829392578 | −0.041358042 | −1.8707506 | 0.0347 |
| 7SK_25 | 1.645006219 | −0.225253243 | −1.8702595 | 0.0185 |
| LOC100288142 | 1.135078116 | −0.732646336 | −1.8677245 | 0.042 |
| PAI1 | 0.288334479 | −1.577332957 | −1.8656674 | 0.0165 |
| ANKS4B | 1.195545377 | −0.669413122 | −1.8649585 | 0.0118 |
| LMO3 | 1.634814698 | −0.218839387 | −1.8536541 | 0.0144 |
| AK097351 | 1.334352859 | −0.517485797 | −1.8518387 | 0.0403 |
| AK054921 | 1.867658952 | 0.023276441 | −1.8443825 | 0.0171 |
| PATE2 | 1.456663994 | −0.37569241 | −1.8323564 | 0.0362 |
| AK057519 | 1.375942192 | −0.450652945 | −1.8265951 | 0.0391 |
| KIAA0087 | 1.453192406 | −0.372680481 | −1.8258729 | 0.00020101 |
| AK310030 | 0.94692851 | −0.873997444 | −1.820926 | 0.0412 |
| CPXM2 | 0.980489476 | −0.838640546 | −1.81913 | 0.0104 |
| RUNX1T1 | 1.379281471 | −0.434087115 | −1.8133686 | 0.00160048 |
| LOC100506801 | 2.22708957 | 0.417009495 | −1.8100801 | 0.0409 |
| TMEM31 | 1.474613174 | −0.326504025 | −1.8011172 | 0.0312 |
| ZNF724P | 1.109620699 | −0.676937677 | −1.7865584 | 0.0447 |
| AK311374 | 1.175128959 | −0.591693956 | −1.7668229 | 0.010001 |
| GNGT2 | 1.478250941 | −0.283849824 | −1.7621008 | 0.029 |
| GRID1 | 1.450107689 | −0.303504274 | −1.753612 | 0.043 |
| PTCD1 | 0.867765657 | −0.876508984 | −1.7442746 | 0.0418 |
| AB209185 | 0.992432762 | −0.72480575 | −1.7172385 | 0.0256 |
| PPP1R27 | 1.284912712 | −0.420503666 | −1.7054164 | 0.01460438 |
| FUT7 | 1.202446913 | −0.493552076 | −1.695999 | 0.0408 |
| NXPH2 | 1.146842456 | −0.53591925 | −1.6827617 | 0.0421 |
| NECAB1 | 1.344474166 | −0.336361027 | −1.6808352 | 0.0428 |
| BC039386 | 0.665066388 | −1.013308845 | −1.6783752 | 0.0226 |
| S100A5 | 1.216385966 | −0.45911622 | −1.6755022 | 0.0101 |
| SFTPD | 1.210754579 | −0.463826745 | −1.6745813 | 0.0351 |
| KU-MEL-3 | 0.736667686 | −0.917946119 | −1.6546138 | 0.02 |
| SALL1 | 1.373486578 | −0.267567614 | −1.6410542 | 0.0093 |
| BC070322 | 0.570803359 | −1.069881966 | −1.6406853 | 0.038 |
| MYH6 | 0.808298187 | −0.829280891 | −1.6375791 | 0.0311 |
| AF086102 | 1.446707055 | −0.185570078 | −1.6322771 | 0.0353 |
| CLUL1 | 1.009188014 | −0.588179621 | −1.5973676 | 0.0198 |
| APOBEC2 | 1.570382716 | −0.024281114 | −1.5946638 | 0.0311 |
| RPL23P8 | 0.242015479 | −1.347761355 | −1.5897768 | 0.0431 |
| COL19A1 | 0.924083274 | −0.664934011 | −1.5890173 | 0.0094 |

TABLE 4-continued

| GeneID | log2FoldChange Placebo | log2FoldChange REGN1908-1909 | post EEU dFC | post EEU dFC p-value |
|---|---|---|---|---|
| LRFN2 | 0.955109537 | −0.630528595 | −1.5856381 | 0.0319 |
| RAB3A | 1.331484517 | −0.248542559 | −1.5800271 | 0.0191 |
| ANO3 | 1.58260987 | 0.010011197 | −1.5725987 | 0.0409 |
| RPS2P32 | 1.745479169 | 0.173185536 | −1.5722936 | 0.032 |
| FOLR2 | 1.724396616 | 0.153828828 | −1.5705678 | 0.0339 |
| AK055332 | 0.871354213 | −0.688636655 | −1.5599909 | 0.0241 |
| FBN3 | 1.028940549 | −0.530633146 | −1.5595737 | 0.0294 |
| MYOZ3 | 1.189512074 | −0.367075623 | −1.5565877 | 0.03760376 |
| NCRUPAR | 1.230399906 | −0.321436058 | −1.551836 | 0.0060024 |
| AX748230 | 1.428576439 | −0.121237592 | −1.549814 | 0.0356 |
| CCDC110 | 1.244087036 | −0.302000729 | −1.5460878 | 0.0257 |
| SLC13A1 | 0.869801824 | −0.674053522 | −1.5438553 | 0.0432 |
| LOC100270746 | 1.185805392 | −0.356843451 | −1.5426488 | 0.0047 |
| EPOR | 1.083322087 | −0.45199832 | −1.5353204 | 0.0055 |
| TMEM252 | 1.329869699 | −0.191016005 | −1.5208857 | 0.0299 |
| LRFN1 | 0.732731174 | −0.783135363 | −1.5158665 | 0.0397 |
| CES1P2 | 1.663109484 | 0.148330642 | −1.5147788 | 0.0075 |
| MAL | 0.600452351 | −0.908237672 | −1.50869 | 0.0401 |
| ADH1A | 0.968963228 | −0.529916914 | −1.4988801 | 0.0381 |
| ILDR2 | 1.181669807 | −0.315734911 | −1.4974047 | 0.0421 |
| CA10 | 1.335129592 | −0.159326644 | −1.4944562 | 0.0364 |
| SCHIP1 | 0.691814781 | −0.795339607 | −1.4871544 | 0.0436 |
| SND1-IT1 | 0.603133684 | −0.880263181 | −1.4833969 | 0.0146 |
| BC042024 | 0.36199709 | −1.089807233 | −1.4518043 | 0.029 |
| NHSL2 | 0.577762456 | −0.873772489 | −1.4515349 | 0.0243 |
| KLRF2 | 0.836760558 | −0.611849677 | −1.4486102 | 0.00510664 |
| PIEZO2 | 0.982849304 | −0.457703552 | −1.4405529 | 0.0093 |
| AL390170 | 1.183666391 | −0.246378989 | −1.4300454 | 0.02870287 |
| BC021693 | 1.332452242 | −0.091115363 | −1.4235676 | 0.0457 |
| FAM198B | 1.730215109 | 0.312018532 | −1.4181966 | 0.0393 |
| TIPARP-AS1 | 0.854593087 | −0.559997387 | −1.4145905 | 0.0047 |
| CD22 | 1.08127784 | −0.327691721 | −1.4089696 | 0.0278 |
| OLFM3 | 1.591207384 | 0.1825095 | −1.4086979 | 0.0399 |
| GNB3 | 0.680425065 | −0.727259077 | −1.4076841 | 0.0474 |
| BC042046 | 0.306253801 | −1.096113855 | −1.4023677 | 0.02320464 |
| BC041007 | 1.094256976 | −0.291401119 | −1.3856581 | 0.00930558 |
| DRD1 | 0.897872472 | −0.463873079 | −1.3617456 | 0.01192504 |
| PGLYRP4 | 0.274812181 | −1.078031714 | −1.3528439 | 0.0431 |
| IGSF9B | 0.897130957 | −0.448589387 | −1.3457203 | 0.01580158 |
| KIF5A | 1.051847126 | −0.287377149 | −1.3392243 | 0.01611128 |
| FKSG63 | 0.757530877 | −0.580809408 | −1.3383403 | 0.0248 |
| AK123947 | 1.231300574 | −0.102126743 | −1.3334273 | 0.01356375 |
| OR4F29 | 0.766351516 | −0.566305142 | −1.3326567 | 0.0357 |
| NKD2 | 1.081176075 | −0.250654732 | −1.3318308 | 0.0449 |
| PCDHA6 | 0.554880676 | −0.775777952 | −1.3306586 | 0.03043043 |
| FOSL1 | 0.878030389 | −0.443220144 | −1.3212505 | 0.0285 |
| LAMB2P1 | 0.826232834 | −0.49014042 | −1.3163733 | 0.037 |
| GBP1P1 | 1.479989715 | 0.164599933 | −1.3153898 | 0.0242 |
| AX746775 | 0.721078837 | −0.585273777 | −1.3063526 | 0.0415 |
| FRMD1 | 1.117190695 | −0.155961104 | −1.2731518 | 0.03163797 |
| PCDHB9 | 0.201074058 | −1.07173849 | −1.2728125 | 0.0395 |
| AK301549 | 0.568088205 | −0.691303916 | −1.2593921 | 0.02581291 |
| ALB | 0.698185519 | −0.545856265 | −1.2440418 | 0.0098 |
| Metazoa_SRP_39 | 0.550701349 | −0.686384461 | −1.2370858 | 0.01558102 |
| LOC100288911 | 0.82060407 | −0.41341315 | −1.2340172 | 0.0382 |
| ENTPD1-AS1 | 1.223860296 | −0.009434589 | −1.2332949 | 0.0443 |
| AX747405 | 0.666079223 | −0.565428712 | −1.2315079 | 0.025 |
| FAM180A | −0.226302806 | −1.456922687 | −1.2306199 | 0.01020612 |
| MI0003602 | 1.155039567 | −0.075467405 | −1.230507 | 0.0458 |
| ZNF891 | 0.66393582 | −0.564318695 | −1.2282545 | 0.017 |
| SPATA31D5P | 0.309808117 | −0.903498471 | −1.2133066 | 0.02561024 |
| LSMEM1 | 0.219228988 | −0.987669952 | −1.2068989 | 0.0278 |
| PMS2L14 | 0.86553972 | −0.33631136 | −1.2018511 | 0.0468 |
| AK093534 | 1.000328824 | −0.185149037 | −1.1854779 | 0.0237 |
| TEX40 | 1.040656941 | −0.143269576 | −1.1839265 | 0.0186093 |
| AK097590 | 0.222861266 | −0.958355385 | −1.1812167 | 0.0485 |
| SERPINB7 | 0.845464191 | −0.323203352 | −1.1686675 | 0.0073 |
| BC047540 | 0.892225564 | −0.272989202 | −1.1652148 | 0.00662663 |
| KRT73 | 1.432732707 | 0.272272651 | −1.1604601 | 0.03830766 |
| BC049825 | 0.7312263 | −0.407164577 | −1.1383909 | 0.0261 |
| TMPRSS6 | 0.48221649 | −0.654233415 | −1.1364499 | 0.03462424 |
| TMEM200B | 0.720080049 | −0.415050086 | −1.1351301 | 0.0065 |
| MAGEA2 | 0.649301799 | −0.465741312 | −1.1150431 | 0.0375413 |
| BC047723 | 1.113749186 | 0.002203867 | −1.1115453 | 0.02261712 |
| BMP2 | 0.701531199 | −0.402558274 | −1.1040895 | 0.0363 |
| HSD3B2 | 0.422430261 | −0.680850259 | −1.1032805 | 0.01587461 |
| AIPL1 | −0.22105041 | −1.321440252 | −1.1003898 | 0.0374 |

TABLE 4-continued

| GeneID | log2FoldChange Placebo | log2FoldChange REGN1908-1909 | post EEU dFC | post EEU dFC p-value |
|---|---|---|---|---|
| KCNA2 | 0.582042474 | −0.493998171 | −1.0760406 | 0.02177622 |
| BC029473 | 0.599398679 | −0.476160805 | −1.0755595 | 0.0445 |
| SCN4A | 0.613186307 | −0.459237511 | −1.0724238 | 0.04416625 |
| CCDC116 | 0.454252358 | −0.616971289 | −1.0712236 | 0.0467 |
| GGN | 0.892060782 | −0.174035254 | −1.066096 | 0.02740414 |
| KCNJ8 | 0.757036383 | −0.305850219 | −1.0628866 | 0.02177419 |
| MI0000285 | 0.441871606 | −0.620640065 | −1.0625117 | 0.03592515 |
| DDX4 | 0.607716805 | −0.448022418 | −1.0557392 | 0.0475 |
| LOC283177 | 0.638856868 | −0.416584421 | −1.0554413 | 0.03696284 |
| MMP7 | 0.747165116 | −0.307513909 | −1.054679 | 0.0059 |
| REM2 | 0.882788374 | −0.16801269 | −1.0508011 | 0.0377 |
| CYP17A1 | 0.583358172 | −0.465754845 | −1.049113 | 0.00797014 |
| NINJ2 | 0.641797889 | −0.394070499 | −1.0358684 | 0.0457 |
| LOC100506060 | 0.702254355 | −0.32940206 | −1.0316564 | 0.0339 |
| AX746750 | 0.787092163 | −0.239877608 | −1.0269698 | 0.0281 |
| ADAMTSL5 | 0.823616376 | −0.202961983 | −1.0265784 | 0.0345 |
| GPR143 | 0.83212059 | −0.19177992 | −1.0239005 | 0.0113 |
| WASH6P | 0.303162933 | −0.71848454 | −1.0216475 | 0.0097 |
| CD2 | 0.712675295 | −0.307636814 | −1.0203121 | 0.02 |
| SPDYE6 | 0.595464963 | −0.423966243 | −1.0194312 | 0.00893228 |
| U4_5 | 0.886776523 | −0.124689548 | −1.0114661 | 0.04166247 |
| MKRN3 | 0.523305765 | −0.484985192 | −1.008291 | 0.0152 |
| IGFBPL1 | 0.600040657 | −0.393800172 | −0.9938408 | 0.0438 |
| LINC00299 | 0.954567324 | −0.030187408 | −0.9847547 | 0.02870861 |
| ZNF699 | 0.787737526 | −0.196716272 | −0.9844538 | 0.0389 |
| ENTPD2 | 0.569873835 | −0.411500552 | −0.9813744 | 0.0485 |
| MTCP1 | 0.450677513 | −0.524245465 | −0.974923 | 0.036 |
| HAS1 | 0.339263009 | −0.628287518 | −0.9675505 | 0.04379269 |
| SLC6A11 | 0.613349975 | −0.354180315 | −0.9675303 | 0.03257819 |
| BTNL3 | 0.473504461 | −0.492569509 | −0.966074 | 0.0424078 |
| AX747756 | 0.799310753 | −0.16664251 | −0.9659533 | 0.0307 |
| OASL | 0.725075899 | −0.23247285 | −0.9575487 | 0.0491 |
| LOC254099 | 0.766327352 | −0.172201971 | −0.9385293 | 0.03887776 |
| GABRB3 | 0.540685038 | −0.39609247 | −0.9367775 | 0.0477 |
| MFAP2 | 0.578500197 | −0.346581341 | −0.9250815 | 0.028 |
| OR4F21 | 0.506655963 | −0.417392854 | −0.9240488 | 0.0488293 |
| TCRBV13S1 | 0.523381824 | −0.398776579 | −0.9221584 | 0.01232777 |
| LOC100287225 | 1.037870977 | 0.118957008 | −0.918914 | 0.01786827 |
| CTXN2 | 0.127409173 | −0.788693267 | −0.9161024 | 0.04110966 |
| SNORA11 2 | 0.679649889 | −0.233883485 | −0.9135334 | 0.03610722 |
| HIC1 | 0.887433497 | −0.025639013 | −0.9130725 | 0.0487 |
| GAMT | 0.084131267 | −0.818747734 | −0.902879 | 0.0238 |
| AK124056 | 0.771316601 | −0.128530658 | −0.8998473 | 0.03516461 |
| LOC100287879 | 0.757065073 | −0.141275352 | −0.8983404 | 0.02453925 |
| C1orf65 | 0.14485434 | −0.748876691 | −0.893731 | 0.04409242 |
| PRTFDC1 | 0.561391571 | −0.328247842 | −0.8896394 | 0.0199 |
| MYZAP | 0.436522952 | −0.452491647 | −0.8890146 | 0.0144 |
| AX746826 | 0.74911126 | −0.122394038 | −0.8715053 | 0.03696264 |
| APOC1 | 0.695576813 | −0.171949637 | −0.8675265 | 0.0485 |
| PRKCB | 0.842607463 | −0.015038569 | −0.857646 | 0.0391 |
| LOC286367 | 0.821784942 | −0.035416791 | −0.8572017 | 0.0497 |
| ZCCHC12 | 0.563715265 | −0.291212191 | −0.8549275 | 0.040143 |
| SGCG | 0.401571353 | −0.448253324 | −0.8498247 | 0.01562166 |
| BC131773 | 0.486210571 | −0.350881299 | −0.8370919 | 0.033 |
| BC016143_6 | 0.506460678 | −0.320356683 | −0.8268174 | 0.0338 |
| ATOH8 | 0.464946746 | −0.360134692 | −0.8250814 | 0.0478 |
| ZNF670-ZNF695 | 0.592140007 | −0.232119939 | −0.8242599 | 0.04018311 |
| HAUS7 | 0.385807499 | −0.438172875 | −0.8239804 | 0.0147 |
| WDFY4 | 0.667739241 | −0.155518562 | −0.8232578 | 0.0362 |
| IFI44L | 0.75695908 | −0.065412116 | −0.8223712 | 0.0479 |
| HCN3 | 0.471155851 | −0.346789114 | −0.817945 | 0.0117 |
| FRRS1L | 0.340066049 | −0.476815105 | −0.8168812 | 0.02455264 |
| ZNF628 | 0.667836999 | −0.141714417 | −0.8095514 | 0.0329 |
| PPP4R1L | 0.597225105 | −0.20277746 | −0.8000026 | 0.0174 |
| SH3TC1 | 0.528966568 | −0.264499919 | −0.7934665 | 0.0017 |
| FABP12 | −0.121624904 | −0.910754689 | −0.7891298 | 0.01071429 |
| ANKRD34A | 0.368815217 | −0.415176018 | −0.7839912 | 0.0482 |
| GPR89C | 0.381451239 | −0.399821402 | −0.7812726 | 0.0461 |
| Em:AC005003.4 | 0.494219902 | −0.28607992 | −0.7802998 | 0.0499 |
| FLI1 | 0.622647152 | −0.153835534 | −0.7764827 | 0.0472 |
| BC073928 | 0.536363676 | −0.23263116 | −0.7689948 | 0.0392 |
| BC035381 | 0.496698103 | −0.260748321 | −0.7574464 | 0.02307857 |
| LIMD2 | 0.429628609 | −0.319023055 | −0.7486517 | 0.0315 |
| PILRA | 0.404823749 | −0.340566044 | −0.7453898 | 0.023 |
| TRAV3J15 | 0.805198097 | 0.062306004 | −0.7428921 | 0.04617706 |
| CXCR4 | 0.410540578 | −0.326034934 | −0.7365755 | 0.0279 |
| LOC100133445 | 0.676079307 | −0.05853115 | −0.7346105 | 0.0452 |

TABLE 4-continued

| GeneID | log2FoldChange Placebo | log2FoldChange REGN1908-1909 | post EEU dFC | post EEU dFC p-value |
|---|---|---|---|---|
| NFKBID | 0.486094693 | −0.238960941 | −0.7250556 | 0.0048 |
| PABPN1 | 0.271699373 | −0.452479072 | −0.7241784 | 0.0166 |
| V alpha immunoglobulin | 0.284631822 | −0.434395344 | −0.7190272 | 0.02904298 |
| MDP1 | 0.053736666 | −0.660018182 | −0.7137548 | 0.0043 |
| FHL3 | 0.652364125 | −0.057205076 | −0.7095692 | 0.0241 |
| TMED8 | 0.546174943 | −0.148264053 | −0.694439 | 0.041 |
| MYL5 | 0.505304372 | −0.188821846 | −0.6941262 | 0.007 |
| RASGRP3 | 0.665233351 | −0.026091095 | −0.6913244 | 0.0297 |
| KIAA1932 | 0.463128913 | −0.220434395 | −0.6835633 | 0.0117 |
| AK310013 | 0.398275075 | −0.28126563 | −0.6795407 | 0.04454621 |
| HCG26 | 0.530307331 | −0.148795563 | −0.6791029 | 0.0272 |
| BMS1P6 | 0.494771359 | −0.17937434 | −0.6741457 | 0.0324 |
| KLHL25 | 0.567130372 | −0.106404077 | −0.6735344 | 0.0428 |
| BCORL1 | 0.4802166 | −0.191161754 | −0.6713784 | 0.0261 |
| AK125727 | 0.408405596 | −0.252743244 | −0.6611488 | 0.0092 |
| ZBTB45 | 0.34496441 | −0.315842406 | −0.6608068 | 0.0085 |
| CTSL2 | 0.298419395 | −0.362002232 | −0.6604216 | 0.0293 |
| MMD | 0.528103311 | −0.130353135 | −0.6584564 | 0.0462 |
| TCEANC | 0.569708878 | −0.079182267 | −0.6488911 | 0.0221 |
| LOC338799 | 0.400692515 | −0.243735417 | −0.6444279 | 0.0172 |
| SOX1 | 0.398941721 | −0.237685687 | −0.6366274 | 0.03135065 |
| TM4SF5 | 0.388168025 | −0.246058841 | −0.6342269 | 0.0345146 |
| ISL1 | 0.521648958 | −0.110572033 | −0.632221 | 0.0465 |
| MAPK11 | 0.571767596 | −0.059316991 | −0.6310846 | 0.0325 |
| COL18A1 | 0.661999497 | 0.03122833 | −0.6307712 | 0.0345 |
| NETO2 | 0.52172147 | −0.106736898 | −0.6284584 | 0.0154 |
| CBLC | 0.349812472 | −0.271842 | −0.6216545 | 0.0313 |
| ZNF250 | 0.370432846 | −0.247894864 | −0.6183277 | 0.0075 |
| IL17RD | 0.550435209 | −0.064808586 | −0.6152438 | 0.0056 |
| SPINK5 | 0.221578286 | −0.386969284 | −0.6085476 | 0.0212 |
| PIDD | 0.370767714 | −0.236788548 | −0.6075563 | 0.011 |
| HLA-DQB2 | −0.290434603 | 0.297214033 | 0.58764864 | 0.0252 |
| SLC38A6 | −0.263604504 | 0.325108273 | 0.58871278 | 0.0133 |
| ZFP30 | −0.36382236 | 0.226600172 | 0.59042253 | 0.0255 |
| ANKRD20A5P | −0.302711992 | 0.287942081 | 0.59065407 | 0.0424 |
| LCA5L | −0.121534914 | 0.469954717 | 0.59148963 | 0.0485 |
| LOC100652758 | −0.120911226 | 0.474286078 | 0.5951973 | 0.037 |
| TCRBV12S2 | −0.468525508 | 0.128497085 | 0.59702259 | 0.03456253 |
| ZNF283 | −0.415146715 | 0.186315518 | 0.60146223 | 0.0286 |
| AK131224 | −0.471918628 | 0.130597637 | 0.60251626 | 0.03247103 |
| BC047600 | −0.47744322 | 0.126544833 | 0.60398805 | 0.04930599 |
| VGF | −0.256635975 | 0.348333004 | 0.60496898 | 0.03810549 |
| IGSF23 | −0.24334394 | 0.363071103 | 0.60641504 | 0.03133372 |
| PRRX1 | −0.326126262 | 0.280365972 | 0.60649223 | 0.0212 |
| ZNF571 | 0.077208687 | 0.686732741 | 0.60952405 | 0.0083 |
| FADS3 | −0.415323708 | 0.194241912 | 0.60956562 | 0.0237 |
| STATH | −0.368124923 | 0.245529704 | 0.61365463 | 0.0339 |
| LINC00698 | −0.235620506 | 0.379533676 | 0.61515418 | 0.03375187 |
| SCARNA14 | −0.210215944 | 0.40581909 | 0.61603503 | 0.03145886 |
| PMS2P3 | −0.48536063 | 0.131265419 | 0.61662605 | 0.0439 |
| LINC00271 | −0.49714624 | 0.119965651 | 0.61711189 | 0.0495 |
| BC148242 | −0.073647052 | 0.544902849 | 0.6185499 | 0.04760917 |
| LPAR1 | −0.400289533 | 0.22018684 | 0.62047637 | 0.008 |
| PAPLN | −0.273403323 | 0.354454133 | 0.62785746 | 0.0307 |
| PTGS1 | −0.577362337 | 0.051473696 | 0.62883603 | 0.0251 |
| GPR39 | −0.405889983 | 0.223005088 | 0.62889507 | 0.0319 |
| SNAP25 | −0.221506534 | 0.407615938 | 0.62912247 | 0.00785582 |
| FCER1A | −0.439596534 | 0.190681755 | 0.63027829 | 0.0415 |
| DKFZP434L187 | −0.237053493 | 0.396473064 | 0.63352656 | 0.02836305 |
| MROH8 | −0.397718592 | 0.236734099 | 0.63445269 | 0.0458 |
| ADARB2 | −0.389576164 | 0.245606495 | 0.63518266 | 0.0337 |
| GLMN | −0.35334244 | 0.288017272 | 0.64135971 | 0.0142 |
| BC079832 | −0.227052524 | 0.422285979 | 0.6493385 | 0.01973456 |
| PNMA5 | −0.254882141 | 0.395567275 | 0.65044942 | 0.02318339 |
| ZNF460 | −0.387509087 | 0.269371016 | 0.6568801 | 0.0413 |
| MI0016006 | −0.510322408 | 0.147169255 | 0.65749166 | 0.00813118 |
| AX747189 | −0.257826688 | 0.401899558 | 0.65972625 | 0.0198248 |
| OTUD6B | −0.380119873 | 0.281207492 | 0.66132736 | 0.003 |
| ZNF624 | −0.442188268 | 0.21954314 | 0.66173141 | 0.0216 |
| RELT | −0.677045304 | −0.012511137 | 0.66453417 | 0.0348 |
| SLC35G6 | −0.396330203 | 0.268955951 | 0.66528615 | 0.02101651 |
| PSMG3-AS1 | −0.279319936 | 0.386679123 | 0.66599906 | 0.0233 |
| MI0000439 | −0.239165096 | 0.427567004 | 0.6667321 | 0.02424662 |
| TRIM17 | −0.358602422 | 0.310115116 | 0.66871754 | 0.0203 |
| DUSP28 | −0.554062021 | 0.118012056 | 0.67207408 | 0.0077 |
| ACOT4 | −0.123395074 | 0.54941911 | 0.67281418 | 0.0274 |
| MYRF | −0.585080856 | 0.088068242 | 0.6731491 | 0.0226 |

TABLE 4-continued

| GeneID | log2FoldChange Placebo | log2FoldChange REGN1908-1909 | post EEU dFC | post EEU dFC p-value |
|---|---|---|---|---|
| SHANK3 | −0.63663502 | 0.037802082 | 0.6744371 | 0.0196 |
| SYT5 | −0.338127265 | 0.338970455 | 0.67709772 | 0.0263 |
| C9orf153 | −0.254318563 | 0.426637142 | 0.6809557 | 0.01023928 |
| CAV1 | −0.373114185 | 0.310227771 | 0.68334196 | 0.0361 |
| DLX1 | −0.395137084 | 0.288417058 | 0.68355414 | 0.01745121 |
| LOC100499489 | −0.454452763 | 0.23133436 | 0.68578712 | 0.0423 |
| MARK2P9 | −0.417576286 | 0.270978409 | 0.6885547 | 0.02445213 |
| SNORD79 | −0.548253607 | 0.148673958 | 0.69692757 | 0.02614238 |
| MSTO2P | −0.46206033 | 0.234977657 | 0.69703799 | 0.0342 |
| ABCA12 | −0.605764157 | 0.091585879 | 0.69735004 | 0.004 |
| HTR7P1 | −0.406653377 | 0.292516077 | 0.69916945 | 0.0473 |
| AKAP6 | −0.321683253 | 0.377632421 | 0.69931567 | 0.0356 |
| COX412 | −0.455498288 | 0.244868648 | 0.70036694 | 0.02509541 |
| LY6G5C | −0.471876016 | 0.229193529 | 0.70106954 | 0.0269 |
| TMEM200A | −0.042476659 | 0.65973422 | 0.70221088 | 0.046 |
| 5S__rRNA__34 | −0.684922192 | 0.01878496 | 0.70370715 | 0.04753219 |
| HV452684 | −0.574283934 | 0.129618053 | 0.70390199 | 0.0163725 |
| LETM2 | −0.266033747 | 0.438551213 | 0.70458496 | 0.0307 |
| SLC12A8 | −0.605849166 | 0.099278148 | 0.70512731 | 0.01 |
| BC033281 | −0.175510611 | 0.530301281 | 0.70581189 | 0.0187 |
| Metazoa__SRP__67 | −0.589259499 | 0.119299348 | 0.70855885 | 0.02289282 |
| PWRN1 | −0.447584243 | 0.263411714 | 0.71099596 | 0.02344923 |
| AK096314 | −0.56445057 | 0.150585268 | 0.71503584 | 0.0388 |
| SH3RF3-AS1 | −0.449188477 | 0.269054147 | 0.71824262 | 0.02570013 |
| BC020917 | −0.324688701 | 0.39598579 | 0.72067449 | 0.04017023 |
| ELK2AP | −0.604289075 | 0.118726011 | 0.72301509 | 0.03422634 |
| TCRVb7.2-Jb1.2 | −0.432137565 | 0.292406641 | 0.72454421 | 0.01129683 |
| AGMAT | −0.740838852 | −0.012011151 | 0.7288277 | 0.0395 |
| WASH1 | −0.235507532 | 0.494373243 | 0.72988077 | 0.0395 |
| SLC6A15 | −0.340659515 | 0.389891472 | 0.73055099 | 0.0397 |
| BC053951 | −0.670990868 | 0.060720383 | 0.73171125 | 0.02426591 |
| TNN | −0.215427521 | 0.517988804 | 0.73341633 | 0.03642283 |
| C1orf56 | −0.327650602 | 0.418314 | 0.7459646 | 0.0131 |
| DLG4 | −0.27785601 | 0.468639931 | 0.74649594 | 0.0403 |
| BC045725 | −0.420083649 | 0.327306496 | 0.74739015 | 0.0386 |
| MCMDC2 | −0.236413248 | 0.513790848 | 0.7502041 | 0.0482 |
| CLDN16 | −0.241183732 | 0.51107595 | 0.75225968 | 0.0324 |
| DGCR9 | −0.491060016 | 0.26249179 | 0.75355181 | 0.03095238 |
| SNORD14 | −0.438199868 | 0.317330881 | 0.75553075 | 0.04915149 |
| AK310237 | −0.455455438 | 0.301009342 | 0.75646478 | 0.0492826 |
| ESR1 | −0.607113709 | 0.153076395 | 0.7601901 | 0.0285 |
| C1orf101 | −0.521371504 | 0.23915725 | 0.76052875 | 0.0327 |
| PRR7-AS1 | −0.064109868 | 0.701186888 | 0.76529676 | 0.04088398 |
| C21orf67 | −0.59720022 | 0.169414066 | 0.76661429 | 0.0483 |
| HIST2H2BF | −0.273669902 | 0.496152232 | 0.76982213 | 0.0415 |
| CCDC140 | −0.598937304 | 0.171130551 | 0.77006786 | 0.0261 |
| ADAMTS17 | −0.779415775 | −0.007259378 | 0.7721564 | 0.0074 |
| SMG1P1 | −0.494409961 | 0.278424346 | 0.77283431 | 0.0392 |
| ACVRL1 | −0.633931002 | 0.14016265 | 0.77409365 | 0.0104 |
| GJB7 | −0.581545597 | 0.193227531 | 0.77477313 | 0.037 |
| ABCB11 | −0.372014142 | 0.408196866 | 0.78021101 | 0.0232 |
| ADORA3 | −0.724715519 | 0.071547379 | 0.7962629 | 0.0484 |
| MZT2A | −0.778934773 | 0.019448818 | 0.79838359 | 0.0198 |
| BC085014 | −0.501341721 | 0.3157404 | 0.81708212 | 0.04688918 |
| BARX2 | −0.540806578 | 0.277017517 | 0.8178241 | 0.0481 |
| STX1A | −0.680551945 | 0.138071397 | 0.81862334 | 0.0059 |
| DIO2-AS1 | −0.687108916 | 0.131599654 | 0.81870857 | 0.01845058 |
| DNER | −0.384332699 | 0.435448604 | 0.8197813 | 0.0239 |
| SPINK8 | −0.237053493 | 0.584970032 | 0.82202353 | 0.01563679 |
| OR7E2P | −0.532302979 | 0.294032717 | 0.8263357 | 0.03058444 |
| BC036404 | −0.827933926 | −0.001340462 | 0.82659346 | 0.02599689 |
| C10orf25 | −0.253475752 | 0.574860594 | 0.82833635 | 0.0422 |
| LOC100129924 | 0.102666608 | 0.932101174 | 0.82943457 | 0.04328178 |
| AX748339 | −0.108039219 | 0.729007618 | 0.83704684 | 0.045 |
| MRC1 | −0.48384599 | 0.353464447 | 0.83731044 | 0.0064 |
| BC037972 | −0.516210057 | 0.321473623 | 0.83768368 | 0.0486 |
| SRP14-AS1 | −0.25581749 | 0.585359297 | 0.84117679 | 0.026 |
| OMG | −0.696938464 | 0.145193194 | 0.84213166 | 0.0371492 |
| AK057513 | −0.260710479 | 0.582224221 | 0.8429347 | 0.03809621 |
| KIAA1586 | −0.215028618 | 0.63710268 | 0.8521313 | 0.0117 |
| LINC00858 | −0.733780248 | 0.118992387 | 0.85277263 | 0.01834577 |
| AK127339 | −0.156948296 | 0.698532516 | 0.85548081 | 0.0227 |
| ADAM21P1 | −0.435359483 | 0.420655543 | 0.85601503 | 0.03720268 |
| CR627148 | −0.504851323 | 0.352037674 | 0.856889 | 0.0396 |
| CCR6 | −0.61564039 | 0.2436017 | 0.85924209 | 0.015 |
| SH3TC2 | −0.444468139 | 0.416365386 | 0.86083352 | 0.0294 |
| LINC00160 | −0.45547627 | 0.406493773 | 0.86197004 | 0.00730084 |

TABLE 4-continued

| GeneID | log2FoldChange Placebo | log2FoldChange REGN1908-1909 | post EEU dFC | post EEU dFC p-value |
|---|---|---|---|---|
| AX747742 | −0.303928785 | 0.560020723 | 0.86394951 | 0.0452 |
| EIF1AY | −0.595468782 | 0.269093122 | 0.8645619 | 0.0054 |
| KIR2DL1 | −0.391585397 | 0.473156481 | 0.86474188 | 0.02443763 |
| LOC100288198 | −0.789303558 | 0.075677195 | 0.86498075 | 0.0079 |
| FAM86EP | −0.286129633 | 0.580356344 | 0.86648598 | 0.001 |
| LY86 | −0.222859726 | 0.646174267 | 0.86903399 | 0.0485 |
| AK094156 | −0.623769918 | 0.250036456 | 0.87380637 | 0.026 |
| TAS2R43 | −0.442011647 | 0.433074051 | 0.8750857 | 0.03206107 |
| LOC100506810 | −0.831446341 | 0.047660396 | 0.87910674 | 0.0178 |
| FLJ16779 | −0.236043166 | 0.646456866 | 0.88250003 | 0.01804254 |
| WTIP | −0.443836269 | 0.447088385 | 0.89092465 | 0.0223 |
| LOC100128822 | −0.522569754 | 0.371420554 | 0.89399031 | 0.0215 |
| CALHM3 | −0.252699333 | 0.646234634 | 0.89893397 | 0.03985544 |
| ZNF501 | −0.12841367 | 0.772910528 | 0.9013242 | 0.0034 |
| COL2A1 | −0.472481229 | 0.432947791 | 0.90542902 | 0.02613648 |
| LINC00663 | −0.469723874 | 0.437108985 | 0.90683286 | 0.0109 |
| LINC00954 | −0.405731554 | 0.50200301 | 0.90773456 | 0.0131 |
| AK056228 | −0.062047376 | 0.848009532 | 0.91005691 | 0.00255258 |
| BC041470 | −0.664839979 | 0.248675748 | 0.91351573 | 0.04220128 |
| LOC440900 | −0.326301991 | 0.587494029 | 0.91379602 | 0.02453306 |
| KLLN | −0.200716228 | 0.719670094 | 0.92038632 | 0.0215 |
| COL16A1 | −0.477543823 | 0.443927872 | 0.9214717 | 0.0124 |
| SLC28A2 | −0.196792917 | 0.729512187 | 0.9263051 | 0.0352 |
| AK126225 | −0.789885329 | 0.142765277 | 0.93265061 | 0.0386 |
| COL6A6 | −1.008619011 | −0.075830093 | 0.93278892 | 0.0093 |
| C10orf99 | −1.07077773 | −0.136214088 | 0.93456364 | 0.03939792 |
| NT5C1B-RDH14 | −0.263236423 | 0.672531135 | 0.93576756 | 0.02389426 |
| FBN1 | −0.204250138 | 0.739843341 | 0.94409348 | 0.0196 |
| HOXA9 | −0.45980349 | 0.486014846 | 0.94581834 | 0.0352953 |
| FLJ46481 | −0.819186153 | 0.13074209 | 0.94992824 | 0.03532856 |
| CHDC2 | −0.282228084 | 0.67050774 | 0.95273582 | 0.021 |
| Metazoa_SRP_58 | −0.691622443 | 0.261584884 | 0.95320733 | 0.0236086 |
| QRICH2 | −0.503232535 | 0.450642275 | 0.95387481 | 0.0244 |
| PCDHAC1 | −0.559866023 | 0.403244937 | 0.96311096 | 0.0251 |
| AF279780 | −0.45077506 | 0.512613247 | 0.96338831 | 0.0418 |
| DGKG | −0.276565813 | 0.689524798 | 0.96609061 | 0.0313 |
| CLEC4G | −0.945947198 | 0.020226207 | 0.9661734 | 0.04932331 |
| AK127697 | −0.399058829 | 0.572028011 | 0.97108684 | 0.03535303 |
| PDE1A | −0.641020579 | 0.335666781 | 0.97668736 | 0.0029 |
| LINC00948 | −0.570378765 | 0.411380719 | 0.98175948 | 0.028 |
| TM4SF19-TCTEX1D2 | −0.61516718 | 0.373666887 | 0.98883407 | 0.01754562 |
| DCTN1-AS1 | −0.705103023 | 0.291708722 | 0.99681174 | 0.02697476 |
| AK307275 | −0.450620049 | 0.547109347 | 0.9977294 | 0.0468797 |
| D28390 | −0.716920412 | 0.280938223 | 0.99785863 | 0.0244848 |
| ITGA9 | −0.564539085 | 0.450562134 | 1.01510122 | 0.0095 |
| RAB40AL | −0.531595077 | 0.486510173 | 1.01810525 | 0.03608403 |
| APLN | −0.439662399 | 0.578793766 | 1.01845617 | 0.00528881 |
| DCSTAMP | −0.708137062 | 0.319729212 | 1.02786627 | 0.01311806 |
| COL8A1 | −0.509479815 | 0.519249433 | 1.02872925 | 0.02380952 |
| VRTN | −0.505277721 | 0.527391728 | 1.03266945 | 0.02542886 |
| SSMEM1 | −1.033279288 | −0.000120005 | 1.03315928 | 0.0234563 |
| ALDH1L1-AS1 | −0.615853445 | 0.420690999 | 1.03654444 | 0.02722049 |
| HNF1A | −0.680007491 | 0.358394231 | 1.03840172 | 0.04481652 |
| TOB2P1 | −1.143604074 | −0.104989534 | 1.03861454 | 0.0479 |
| INO80B | −0.689893621 | 0.351317774 | 1.0412114 | 0.0072 |
| Metazoa_SRP_17 | −0.419831267 | 0.62217018 | 1.04200145 | 0.02470988 |
| COL4A4 | −0.333164866 | 0.71659456 | 1.04975943 | 0.0429 |
| LINC00112 | −0.792838223 | 0.258901655 | 1.05173988 | 0.01980497 |
| UGT2B28 | −0.646280418 | 0.407317489 | 1.05359791 | 0.01182774 |
| VAX2 | −0.38713375 | 0.669358241 | 1.05649199 | 0.00603076 |
| GAD1 | −0.520320798 | 0.537687262 | 1.05800806 | 0.0419 |
| CAPNS2 | −0.743052579 | 0.315507595 | 1.05856017 | 0.0072 |
| TUSC5 | −0.652090122 | 0.406618378 | 1.0587085 | 0.00487299 |
| RBM46 | −1.183840845 | −0.12473675 | 1.0591041 | 0.0313533 |
| LOC728739 | −0.98850459 | 0.071870251 | 1.06037484 | 0.02363398 |
| LGSN | −0.494332444 | 0.572706473 | 1.06703892 | 0.0397 |
| DQ574505 | −0.81429372 | 0.253027612 | 1.06732133 | 0.0205 |
| HYAL4 | −0.717663719 | 0.350003318 | 1.06766704 | 0.0293 |
| LOC100505474 | −0.80881322 | 0.259627108 | 1.06844033 | 0.04095734 |
| TCRBV13S6A2T | −0.419030109 | 0.650490906 | 1.06952102 | 0.00873757 |
| C3orf70 | −0.80098903 | 0.271934737 | 1.07292377 | 0.0492 |
| UNC5D | 0.088836404 | 1.16178956 | 1.07295316 | 0.0406 |
| TRAV20 | −0.758343621 | 0.316250144 | 1.07459377 | 0.01448684 |
| CDKN3 | −0.858557629 | 0.220757387 | 1.07931502 | 0.0134 |
| ZNF774 | −0.863536299 | 0.224362241 | 1.08789854 | 0.0195 |
| RBM11 | −0.489879594 | 0.598105842 | 1.08798544 | 0.0465 |
| SHISA3 | −0.503108195 | 0.58770063 | 1.09080882 | 0.01573056 |

TABLE 4-continued

| GeneID | log2FoldChange Placebo | log2FoldChange REGN1908-1909 | post EEU dFC | post EEU dFC p-value |
|---|---|---|---|---|
| C9orf170 | −0.032527448 | 1.058724041 | 1.09125149 | 0.04007614 |
| RBP5 | −0.269142028 | 0.822895707 | 1.09203773 | 0.02240224 |
| NPAS1 | −0.791595814 | 0.304536576 | 1.09613239 | 0.0256 |
| CDY2A | −0.522390163 | 0.582076675 | 1.10446684 | 0.01331465 |
| STBD1 | −0.418273564 | 0.687367701 | 1.10564126 | 0.0459 |
| LOC441081 | −0.541449559 | 0.564533717 | 1.10598328 | 0.024 |
| BC019672 | −1.014591863 | 0.093799017 | 1.10839088 | 0.04791437 |
| CST9 | −0.81811834 | 0.292019338 | 1.11013768 | 0.03764141 |
| P2RY4 | −0.430998751 | 0.685325078 | 1.11632383 | 0.01194659 |
| CNBD1 | −0.402616721 | 0.718878022 | 1.12149474 | 0.01952343 |
| DL490887 | −0.570607128 | 0.559261865 | 1.12986899 | 0.00842021 |
| PCDHGA10 | −0.76705227 | 0.364473593 | 1.13152586 | 0.0052 |
| ZNF382 | −0.658604573 | 0.474542994 | 1.13314757 | 0.0106 |
| LDLRAD2 | −0.880515431 | 0.260009131 | 1.14052456 | 0.0127 |
| SLAMF9 | −0.224833469 | 0.923184673 | 1.14801814 | 0.0425 |
| CCNA2 | −0.26128531 | 0.897239393 | 1.1585247 | 0.0107 |
| AWAT2 | −0.669782102 | 0.490397396 | 1.1601795 | 0.0422761 |
| AB586698 | −0.574829965 | 0.589065256 | 1.16389522 | 0.04112467 |
| SLC25A21-AS1 | −0.316437654 | 0.849828435 | 1.16626609 | 3.00E−04 |
| MT1IP | −0.896157424 | 0.27184857 | 1.16800599 | 0.0114217 |
| OCA2 | −0.342382701 | 0.826298127 | 1.16868083 | 0.0443 |
| SFTA1P | −1.158559007 | 0.016600225 | 1.17515923 | 0.04132479 |
| AK057259 | −1.166637841 | 0.008681865 | 1.17531971 | 0.04090409 |
| ATP1A1OS | −0.640698861 | 0.541992382 | 1.18269124 | 0.0022 |
| GCSAML-AS1 | −0.538889896 | 0.645153161 | 1.18404306 | 0.0247495 |
| LOC100130557 | −0.434125951 | 0.750401541 | 1.18452749 | 0.0047 |
| NXNL2 | −0.925056633 | 0.260589699 | 1.18564633 | 0.01109878 |
| HSF2BP | −0.832716755 | 0.356848048 | 1.1895648 | 0.0067 |
| CYP4Z2P | −0.855380414 | 0.335179073 | 1.19055949 | 0.04851455 |
| FLJ41941 | −0.970824875 | 0.224053452 | 1.19487833 | 0.02934696 |
| SNORA66 | −0.651570525 | 0.548935459 | 1.20050598 | 0.00315457 |
| CD1A | −0.772872414 | 0.42857439 | 1.2014468 | 0.0436 |
| AK301968 | −1.192991177 | 0.011362897 | 1.20435407 | 0.01659459 |
| ROR2 | −1.057023298 | 0.147684199 | 1.2047075 | 0.0259 |
| LOC339290 | −1.054840422 | 0.158533158 | 1.21337358 | 0.04710942 |
| ITIH1 | −1.127022163 | 0.089261968 | 1.21628413 | 0.03641092 |
| AK300656 | −0.383456331 | 0.833921591 | 1.21737792 | 0.0032 |
| QRFPR | −0.361708788 | 0.861717962 | 1.22342675 | 0.0463 |
| TCP11 | −0.246100966 | 0.977425109 | 1.22352608 | 0.0271 |
| SLC35F1 | −0.781136007 | 0.443292352 | 1.22442836 | 0.03460346 |
| ASCL1 | −1.020008652 | 0.227705617 | 1.24771427 | 0.0092873 |
| TCRBV9S1A1T | −0.680146121 | 0.567723874 | 1.24786999 | 0.0430043 |
| TRPM2 | −1.07794892 | 0.17058115 | 1.24853007 | 0.0411 |
| DCC | −0.406888867 | 0.855590329 | 1.2624792 | 0.0196 |
| SIRPD | −0.618718575 | 0.647343896 | 1.26606247 | 0.01890756 |
| KRTAP5-2 | −0.813363139 | 0.45771553 | 1.27107867 | 0.00713783 |
| LOC100133050 | −0.52938474 | 0.745644343 | 1.27502908 | 0.0244 |
| MB21D2 | −0.007501575 | 1.268980713 | 1.27648229 | 0.02 |
| POLN | −0.206784771 | 1.07685095 | 1.28363572 | 0.0349 |
| CARD9 | −1.043314923 | 0.24348888 | 1.2868038 | 0.0215 |
| ZNF556 | −0.895399554 | 0.392401366 | 1.28780092 | 0.0124 |
| LOC148709 | −1.130099444 | 0.173518378 | 1.30361782 | 0.041 |
| MEP1A | −0.817276752 | 0.499415079 | 1.31669183 | 0.0019 |
| STAU2-AS1 | −0.831234574 | 0.485618097 | 1.31685267 | 0.0124 |
| BSN | 0.156088343 | 1.473072273 | 1.31698393 | 0.0112 |
| DQ658414 | −1.238671038 | 0.079309171 | 1.31798021 | 0.0269 |
| SLC2A14 | −1.145778693 | 0.177529624 | 1.32330832 | 0.00560112 |
| SPESP1 | −0.709653304 | 0.615728142 | 1.32538145 | 0.0019 |
| BLOC1S5 | −0.532148754 | 0.799462842 | 1.3316116 | 0.0261 |
| F2RL3 | −0.551224144 | 0.781627108 | 1.33285125 | 0.0093177 |
| AHSG | −0.766119723 | 0.567621401 | 1.33374112 | 0.02990299 |
| LOC100505841 | −0.066920648 | 1.272553587 | 1.33947423 | 0.0445 |
| IQGAP3 | −0.410987779 | 0.92927427 | 1.34026205 | 0.0382 |
| AK127124 | −1.007697337 | 0.333095276 | 1.34079261 | 0.0296 |
| FAM182B | −0.553108744 | 0.790349147 | 1.34345789 | 0.0055 |
| BC030152 | −0.689578723 | 0.660618692 | 1.35019741 | 0.0153 |
| TEX21P | −0.273622766 | 1.077037343 | 1.35066011 | 0.0375 |
| PABPC1P2 | −0.635878321 | 0.721193564 | 1.35707189 | 0.01650165 |
| UMODL1 | −0.189686802 | 1.171451452 | 1.36113825 | 0.0224 |
| TCRBV3S1 | −0.30047763 | 1.071201976 | 1.37167961 | 0.0187 |
| FMO9P | −1.072149455 | 0.302868929 | 1.37501838 | 0.0236 |
| BC033983 | −0.768028514 | 0.609261004 | 1.37728952 | 0.0184 |
| KRTAP5-10 | −0.892427957 | 0.495292262 | 1.38772022 | 0.0339 |
| RASAL2-AS1 | −1.021238673 | 0.372378383 | 1.39361706 | 0.0172 |
| AJ606331 | −0.649828161 | 0.748399534 | 1.39822769 | 0.0405 |
| SH2D6 | −0.639879134 | 0.759918174 | 1.39979731 | 0.0475 |
| DSG1 | −1.242426186 | 0.160644932 | 1.40307112 | 0.00858152 |

TABLE 4-continued

| GeneID | log2FoldChange Placebo | log2FoldChange REGN1908-1909 | post EEU dFC | post EEU dFC p-value |
|---|---|---|---|---|
| LEMD1 | 0.016686808 | 1.426898713 | 1.4102119 | 0.0281 |
| NKAIN2 | −0.631053507 | 0.779465624 | 1.41051913 | 0.0227 |
| CR933665 | −0.399371807 | 1.01335322 | 1.41272503 | 0.0366 |
| BX648502 | −0.215599578 | 1.198810816 | 1.41441039 | 0.04530453 |
| LOC286297 | −1.026211327 | 0.388876318 | 1.41508764 | 0.0230069 |
| LOC647859 | −1.338564864 | 0.077761806 | 1.41632667 | 0.0452 |
| BC053679 | −1.097879691 | 0.319008034 | 1.41688773 | 0.0187 |
| VWCE | −1.124666155 | 0.305671784 | 1.43033794 | 0.0183 |
| JN120857 | −1.106758418 | 0.33646778 | 1.4432262 | 0.0229 |
| ALPPL2 | −0.528622048 | 0.916804608 | 1.44542666 | 0.01170117 |
| ALX4 | −0.560184052 | 0.890225835 | 1.45040989 | 0.0247 |
| Metazoa_SRP_66 | −0.990754486 | 0.461898865 | 1.45265335 | 0.02950295 |
| WEE2 | −0.84014808 | 0.613393809 | 1.45354189 | 0.0387 |
| SPARC | −0.248135944 | 1.205498169 | 1.45363411 | 0.0417 |
| SPTB | −0.830339119 | 0.631252246 | 1.46159137 | 0.00430258 |
| SLC22A13 | −0.658006892 | 0.805061559 | 1.46306845 | 0.0082115 |
| GPR37 | −1.23238739 | 0.230839097 | 1.46322649 | 8.00E−04 |
| POU6F2 | −1.128718221 | 0.34288367 | 1.47160189 | 0.00690345 |
| F12 | −0.583507375 | 0.888560478 | 1.47206785 | 0.0057 |
| PDGFRA | −0.459919416 | 1.012282108 | 1.47220152 | 0.0248 |
| TPPP2 | −0.928411215 | 0.545229513 | 1.47364073 | 0.0445 |
| RPL13AP20 | −0.861685716 | 0.616570633 | 1.47825635 | 0.0113 |
| KNCN | −0.140725931 | 1.341703195 | 1.48242913 | 0.0312 |
| FLJ30838 | −0.575653714 | 0.914212637 | 1.48986635 | 0.00690069 |
| AIFM3 | −0.652566986 | 0.841665245 | 1.49423223 | 0.0072 |
| BLOC1S1-RDH5 | −0.422928649 | 1.075428533 | 1.49835718 | 0.0301 |
| ZNF177 | −1.242230314 | 0.263500584 | 1.5057309 | 0.0145 |
| RAB9B | 0.010660002 | 1.516772402 | 1.5061124 | 0.0438 |
| ZNF815P | −0.616990103 | 0.894135129 | 1.51112523 | 0.0155 |
| TRAV12-1 | −0.21498268 | 1.301315031 | 1.51629771 | 0.0335 |
| LOC339047 | −0.463939414 | 1.052639289 | 1.5165787 | 0.0033 |
| BC070061 | −1.561706481 | −0.031285959 | 1.53042052 | 0.0154 |
| SLC2A5 | −0.468107543 | 1.065527069 | 1.53363461 | 0.0427 |
| BC046483 | −1.151667658 | 0.39804192 | 1.54970958 | 0.0153 |
| ATOH7 | −0.562165634 | 0.987766134 | 1.54993177 | 0.0132 |
| UTS2B | −0.454503087 | 1.103491978 | 1.55799507 | 0.04340434 |
| LOC100289388 | −0.980718222 | 0.582828586 | 1.56354681 | 0.0398 |
| MCF2L2 | −0.672818785 | 0.898981375 | 1.57180016 | 0.0122 |
| COL9A1 | −1.143510053 | 0.428951443 | 1.5724615 | 0.0218 |
| CXorf57 | −0.214819637 | 1.361454789 | 1.57627443 | 0.0284 |
| BC017910 | −0.655186114 | 0.931689609 | 1.58687572 | 0.0427 |
| SUMO1P3 | −0.053999953 | 1.534948358 | 1.58894831 | 0.0328 |
| MATN1-AS1 | −0.562864402 | 1.027478203 | 1.5903426 | 0.0246 |
| IGLL5 | −0.390087326 | 1.207824114 | 1.59791144 | 0.0283 |
| DQ577420 | −0.908076288 | 0.690758441 | 1.59883473 | 0.0005011 |
| CCDC73 | −0.712681334 | 0.888769359 | 1.60145069 | 0.0266 |
| FAM95B1 | −0.66729313 | 0.934674316 | 1.60196745 | 0.046 |
| LOC100289092 | −1.390225901 | 0.217762428 | 1.60798833 | 0.0381 |
| PNMA2 | −0.615614163 | 1.003844866 | 1.61945903 | 0.0155 |
| AK125437 | −1.149691533 | 0.474229094 | 1.62392063 | 0.0449 |
| SLC7A5P2 | −1.327921662 | 0.2982561 | 1.62617776 | 0.0487 |
| ZNF367 | −0.709451074 | 0.919972664 | 1.62942374 | 0.0023 |
| LOC100131060 | −0.447556149 | 1.183546676 | 1.63110283 | 0.0478 |
| C11orf53 | −0.617564375 | 1.019533001 | 1.63709738 | 0.0215 |
| MRVI1-AS1 | −0.11632539 | 1.522235144 | 1.63856053 | 0.0145 |
| RUSC1-AS1 | −1.265570936 | 0.382193771 | 1.64776471 | 0.0295 |
| LOC51326 | −1.652903041 | −0.003710659 | 1.64919238 | 0.0334 |
| DSCR9 | −1.701807721 | −0.045290277 | 1.65651744 | 0.0217 |
| TRGC2 | −0.667496097 | 0.99356103 | 1.66105713 | 0.0405 |
| NPSR1-AS1 | −0.620342443 | 1.046183373 | 1.66652582 | 0.0080016 |
| ABCB4 | −0.634925718 | 1.034990376 | 1.66991609 | 0.0424 |
| AX746969 | −2.032606808 | −0.3593406 | 1.67326621 | 0.0402 |
| CRB2 | −1.168039941 | 0.507438871 | 1.67547881 | 0.00270243 |
| ESM1 | −0.765795107 | 0.931357849 | 1.69715296 | 0.0302 |
| ADAMTS15 | −0.608390195 | 1.093672847 | 1.70206304 | 0.0314 |
| GPR25 | −0.240749725 | 1.473946262 | 1.71469599 | 0.035 |
| CDH17 | −0.903796224 | 0.817155486 | 1.72095171 | 0.0099 |
| NIM1 | 0.397717713 | 2.121701926 | 1.72398421 | 0.0208 |
| FLJ38723 | −0.194304414 | 1.540203953 | 1.73450837 | 0.0314 |
| LOC100129138 | −0.085230442 | 1.662658734 | 1.74788918 | 0.0215 |
| LIN7B | −0.953971261 | 0.795909855 | 1.74988112 | 0.0036 |
| SLC47A2 | −1.058353845 | 0.69902827 | 1.75738211 | 0.0132 |
| IL36G | −2.252245213 | −0.492371664 | 1.75987355 | 0.0496 |
| GOLGA8T | −0.428431992 | 1.332199051 | 1.76063104 | 0.0284 |
| WFDC1 | −0.248807528 | 1.513426523 | 1.76223405 | 0.0412 |
| FOXD2-AS1 | −1.076337453 | 0.695605394 | 1.77194285 | 0.0156 |
| OR7D2 | −0.543465094 | 1.231693664 | 1.77515876 | 0.0375 |

TABLE 4-continued

| GeneID | log2FoldChange Placebo | log2FoldChange REGN1908-1909 | post EEU dFC | post EEU dFC p-value |
|---|---|---|---|---|
| GPR63 | −0.338015236 | 1.437520519 | 1.77553576 | 0.0257 |
| FOXD4L1 | −0.233364756 | 1.54427799 | 1.77764275 | 0.0056 |
| LOC100507537 | −1.002632551 | 0.780042446 | 1.782675 | 0.0159 |
| BC036361 | −1.00634796 | 0.792705358 | 1.79905332 | 0.007 |
| BC070106 | −0.858764214 | 0.942780844 | 1.80154506 | 0.0408 |
| BEND4 | −0.706160022 | 1.096134797 | 1.80229482 | 0.0059 |
| CYS1 | −0.941776779 | 0.869330843 | 1.81110762 | 0.0163 |
| FLJ23584 | −1.445475774 | 0.365759809 | 1.81123558 | 0.0117 |
| GRIP2 | −1.63160158 | 0.194848558 | 1.82645014 | 0.038 |
| CKLF-CMTM1 | −0.118377838 | 1.717203493 | 1.83558133 | 0.039 |
| SPINK6 | −1.669515427 | 0.188202513 | 1.85771794 | 0.0252 |
| SARDH | 0.147801481 | 2.011019229 | 1.86321775 | 0.0079 |
| HS3ST3B1 | −1.469144885 | 0.400978475 | 1.87012336 | 0.0469 |
| LOC643723 | −1.598677661 | 0.272574374 | 1.87125203 | 0.0315 |
| DJ031142 | −0.620653542 | 1.250636752 | 1.87129029 | 0.0166 |
| SMAD5-AS1 | −1.409224446 | 0.465688027 | 1.87491247 | 0.0257 |
| AJ420489 | −0.790757681 | 1.087319715 | 1.8780774 | 0.0328 |
| PDE2A | −1.045413276 | 0.834407189 | 1.87982046 | 0.0163 |
| EIF5AL1 | −1.198966324 | 0.690352249 | 1.88931857 | 0.0068 |
| UCN | −0.266505898 | 1.629566013 | 1.89607191 | 0.00110011 |
| SNPH | −1.12953611 | 0.76915978 | 1.89869589 | 0.0087 |
| ANO7 | −1.07122971 | 0.829658066 | 1.90088778 | 0.0121 |
| SPC25 | −0.309473222 | 1.601405034 | 1.91087826 | 0.0221 |
| AX747264 | −0.923829895 | 0.992188618 | 1.91601851 | 0.0342 |
| SNORA6 | −0.335280579 | 1.582476328 | 1.91775691 | 0.0458 |
| SEC14L4 | −1.205680719 | 0.713939715 | 1.91962043 | 0.0238 |
| HLA-DPB2 | −0.466305898 | 1.453766533 | 1.92007243 | 0.0271 |
| C2orf27A | −1.318497617 | 0.612334836 | 1.93083245 | 0.0301 |
| AX747125 | −1.038262598 | 0.895489953 | 1.93375255 | 0.0061 |
| SSR4P1 | −1.120921349 | 0.815326311 | 1.93624766 | 9.00E−04 |
| TFAP2B | −1.37715722 | 0.566583454 | 1.94374067 | 0.0189 |
| BC045163 | −0.587162006 | 1.362571203 | 1.94973321 | 0.0295 |
| KIF18B | −0.331476302 | 1.618612604 | 1.95008891 | 0.0106 |
| LOC644145 | −1.495778641 | 0.466883176 | 1.96266182 | 0.0414 |
| RFPL1S | −0.790717894 | 1.178302695 | 1.96902059 | 0.0279 |
| IL9R | −1.1812216 | 0.791681617 | 1.97290322 | 0.0215 |
| SNORA52 | −1.661024988 | 0.319984925 | 1.98100991 | 0.0411 |
| DPRXP4 | −0.650718154 | 1.333217894 | 1.98393605 | 0.0438 |
| LOC285768 | −0.819459182 | 1.165635891 | 1.98509507 | 0.0191 |
| CHKB-AS1 | −0.952717525 | 1.033816061 | 1.98653359 | 0.0204 |
| BCL2L2-PABPN1 | −0.402868173 | 1.585051334 | 1.98791951 | 0.0297 |
| STXBP5L | −1.031533194 | 0.959606816 | 1.99114001 | 0.0283 |
| AK309988 | −1.004211617 | 0.997166358 | 2.00137798 | 0.0042 |
| DLEU7 | −0.7234487 | 1.281834469 | 2.00528317 | 0.0255 |
| SLFNL1-AS1 | −1.436210737 | 0.569900699 | 2.00611144 | 0.042 |
| GABRR1 | −1.85569355 | 0.153295462 | 2.00898901 | 0.0324 |
| C10orf55 | −0.899427023 | 1.121644471 | 2.02107149 | 0.0329 |
| LOC100131655 | −0.518893394 | 1.516140786 | 2.03503418 | 0.0281 |
| NR5A2 | −0.0524041 | 1.986138976 | 2.03854308 | 0.039 |
| OLFM2 | −0.709427893 | 1.332288898 | 2.04171679 | 0.0206 |
| DL492607 | −1.03989866 | 1.004579738 | 2.0444784 | 0.0046 |
| ADAM12 | −1.121442661 | 0.926297985 | 2.04774065 | 0.0213 |
| TDRD9 | −0.108858005 | 1.938924751 | 2.04778276 | 0.0127 |
| FAM74A4 | −1.025961372 | 1.023304489 | 2.04926586 | 0.0349 |
| BC062769 | −1.2880197 | 0.76737426 | 2.05539396 | 0.0265 |
| SLC30A4 | −0.976913421 | 1.082981323 | 2.05989474 | 0.0029 |
| LOC339874 | −0.60617604 | 1.460480873 | 2.06665691 | 0.0137 |
| LOC100128531 | −1.299189379 | 0.769976061 | 2.06916544 | 0.0052 |
| AK097190 | −1.137734863 | 0.945358216 | 2.08309308 | 0.0186 |
| BC080653 | −1.460264065 | 0.635335381 | 2.09559945 | 0.0061 |
| PEG3 | −0.344619743 | 1.767540581 | 2.11216032 | 0.0213 |
| RBFADN | −0.090010605 | 2.026930218 | 2.11694082 | 0.0133 |
| FAM64A | 0.417415288 | 2.544956735 | 2.12754145 | 0.0303 |
| CR627206 | −1.363230547 | 0.775998216 | 2.13922876 | 0.0048 |
| ETV2 | −0.354440628 | 1.78930385 | 2.14374448 | 0.0303 |
| GPSM1 | −0.825805234 | 1.320358173 | 2.14616341 | 0.0014 |
| PKNOX2 | −1.681560432 | 0.47092632 | 2.15248675 | 0.0163 |
| AK309255 | −0.423543452 | 1.748895415 | 2.17243887 | 0.0198 |
| PI16 | −0.466378197 | 1.714123296 | 2.18050149 | 0.0498 |
| SLC4A10 | −2.041018751 | 0.144112456 | 2.18513121 | 0.0419 |
| TUBB4A | −1.038420644 | 1.161410911 | 2.19983155 | 0.0021 |
| AKR1C4 | −1.265594773 | 0.940276248 | 2.20587102 | 0.0388 |
| C17orf67 | −1.536894291 | 0.669592132 | 2.20648642 | 0.0302 |
| AX746484 | −0.421531742 | 1.797300851 | 2.21883259 | 0.0379 |
| SLC7A9 | −1.125439852 | 1.097618878 | 2.22305873 | 0.0083 |
| LOC643355 | −0.300075411 | 1.928918101 | 2.22899351 | 0.0166 |
| LOC645166 | −0.571406639 | 1.65916356 | 2.2305702 | 0.0275 |

TABLE 4-continued

| GeneID | log2FoldChange Placebo | log2FoldChange REGN1908-1909 | post EEU dFC | post EEU dFC p-value |
|---|---|---|---|---|
| SLC28A1 | −0.431504162 | 1.833785075 | 2.26528924 | 0.0309 |
| FAM225B | −1.140719364 | 1.140086826 | 2.28080619 | 0.0217 |
| ZNF663 | 0.26010414 | 2.54689479 | 2.28679065 | 0.0444 |
| GLB1L3 | −1.19813146 | 1.089920821 | 2.28805228 | 0.0372 |
| AK055272 | −2.061577427 | 0.227095975 | 2.2886734 | 0.0213 |
| ASGR2 | −0.488345913 | 1.810956298 | 2.29930221 | 0.0074 |
| ZCCHC18 | −0.645504979 | 1.654636925 | 2.3001419 | 0.0293 |
| LINC00312 | −1.509835045 | 0.793083417 | 2.30291846 | 0.031 |
| BMPER | −1.448834428 | 0.876513553 | 2.32534798 | 0.0347 |
| SYT2 | −1.050179155 | 1.275595239 | 2.32577439 | 0.0014 |
| CAMK2A | −0.524164276 | 1.809820034 | 2.33398431 | 0.0497 |
| GRK7 | −1.900962272 | 0.43390692 | 2.33486919 | 0.0298 |
| HEATR4 | −0.457729358 | 1.911201102 | 2.36893046 | 0.0016 |
| BC023651 | −1.564770366 | 0.80952026 | 2.37429063 | 0.023 |
| AK095633 | −1.854990885 | 0.529075113 | 2.384066 | 0.0076 |
| CSPG4 | −0.737026156 | 1.684951223 | 2.42197738 | 0.0047 |
| SNORA81 | −0.967920132 | 1.455884688 | 2.42380482 | 0.0153 |
| U1_10 | −0.030976774 | 2.399967219 | 2.43094399 | 0.0477 |
| BC065373 | −1.482450812 | 0.959759189 | 2.44221 | 0.0153 |
| AK056432 | −0.305812294 | 2.156899391 | 2.46271169 | 0.0257 |
| BC040572 | −0.5086352 | 1.967480331 | 2.47611553 | 0.0254 |
| RAB40A | −0.698770133 | 1.798673383 | 2.49744352 | 0.0038 |
| BC040208 | −1.92831469 | 0.579945457 | 2.50826015 | 0.0179 |
| HABP2 | −1.052054126 | 1.462226684 | 2.51428081 | 0.0079 |
| MGC16142 | −1.247465261 | 1.280087585 | 2.52755285 | 0.013 |
| PEBP4 | −1.730813444 | 0.799982681 | 2.53079612 | 0.0047 |
| CCDC154 | −1.379488231 | 1.181901516 | 2.56138975 | 0.0272 |
| LOC440934 | −1.639077701 | 0.953511571 | 2.59258927 | 0.0444 |
| AK128837 | −1.520295209 | 1.078776005 | 2.59907121 | 0.0359 |
| BVES | −1.014961257 | 1.626170464 | 2.64113172 | 0.0053 |
| IGSF1 | −1.644677685 | 1.000130805 | 2.64480849 | 0.0051 |
| AX746944 | −0.513068189 | 2.169664563 | 2.68273275 | 0.0064 |
| AB075492 | −0.735273767 | 1.963219504 | 2.69849327 | 0.0201 |
| MYH16 | −2.282063729 | 0.465983161 | 2.74804689 | 0.0403 |
| RFTN2 | −2.171393282 | 0.580112873 | 2.75150615 | 0.0183 |
| LOC100130015 | −1.777477934 | 0.980214404 | 2.75769234 | 0.0026 |
| TLE6 | −0.603367351 | 2.197160003 | 2.80052735 | 0.008 |
| AX746627 | −1.640954524 | 1.175439442 | 2.81639397 | 0.0387 |
| MUC3B | −2.558438057 | 0.276519347 | 2.8349574 | 0.0131 |
| CABC1 | −1.215747748 | 1.650616789 | 2.86636454 | 0.0385 |
| LOC285972 | −1.962934642 | 0.940715834 | 2.90365048 | 0.003 |
| BC024248 | −2.426990135 | 0.506358513 | 2.93334865 | 0.027 |
| COL5A3 | −1.930052701 | 1.077828107 | 3.00788081 | 0.0016 |
| NSFP1 | −2.281782525 | 0.738846193 | 3.02062872 | 0.0407 |
| ANKRD55 | −1.462338299 | 1.610163614 | 3.07250191 | 0.0023 |
| TRA@ | −2.082680075 | 1.005962325 | 3.0886424 | 0.0154 |
| PRSS30P | −0.845107958 | 2.253957514 | 3.09906547 | 0.047 |
| ZNF385D | −1.014767327 | 2.105770876 | 3.1205382 | 0.0233 |
| AK098783 | −2.644308148 | 0.49985305 | 3.1441612 | 0.0041 |
| CORT | −2.097080892 | 1.3377838 | 3.43486469 | 0.0089 |
| TLR9 | −1.359944763 | 2.178696367 | 3.53864113 | 0.0176 |
| KCND2 | −2.02170529 | 1.799792594 | 3.82149788 | 0.0024 |
| AK095546 | −1.625649314 | 2.203991971 | 3.82964129 | 1.00E−04 |
| FAM35BP | −2.842188066 | 2.215622851 | 5.05781092 | 0.0061 |
| ATP5J2-PTCD1 | −8.208101085 | 1.796598344 | 10.0046994 | 0.002 |
| RAD51L3-RFFL | 0.112967286 | 12.06139153 | 11.9484242 | 0.0194 |
| LOC727751 | 0.328794222 | 14.48792372 | 14.1591295 | 0.00530424 |

The NEC cat allergy gene signature was significantly reversed by REGN1908-1909 relative to placebo (NES=−1.65, p=0.001).

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A method of identifying a subject as suitable for the treatment or prevention of asthma exacerbation induced by a cat allergen with at least one antibody to the cat allergen, the method comprising:

a) generating or having generated a first transcriptome for the subject;

b) exposing the subject to at least one cat allergen;

c) generating or having generated a second transcriptome for the subject after exposure to the at least one cat allergen; and d) screening the second transcriptome against the first transcriptome to generate a cat allergen exposure transcriptome;

wherein the subject is suitable for the treatment or prevention of asthma exacerbation induced by a cat allergen with at least one antibody to the cat allergen when the cat allergen exposure transcriptome comprises:

a downregulation of at least any ten of the following genes: CCDC33, ADH6, IFLTD1, DLGAP1-AS5, DNAJB13, C2orf62, CCDC81, PIH1D3, NHLRC4, TMEM190, AK090700, KIF6, BBOX1, PTGFR, SEC14L3, BC022056, CASC2, PPP1R36, CNTN5, KLHDC8A, FHOD3, CAPS, UBD, TP73, BC023516, IFI44L, FAM86B1, CX3CL1, ACY3, MPDZ, IGFBP5, AK097288, IFI6, ABCC6, GAS1, and PLCH1; and an upregulation of at least any twenty of the following genes: ESPL1, NMU, CTSL2, CLIC3, CRABP2, AX746775, TMPRSS11A, NCCRP1, MSX2, HSP90AB4P, AIMIL, SERPINB2, ILIRN, KLK10, PXDN, HSPB8, CLCA4, KRT10, ZBED2, DSC2, LY6G6C, ADAMTSL4, OTOP3, FGFBP1, GPR115, TRPV3, CRISP3, SPRR3, PRSS3, A2ML1, SPINK7, LYPD3, RHCG, SPRRIA, MAP2, S100A8, RPTN, PRSS27, KRT6B, PPP2R2C, ILIRL1, CAMK2N1, CPA4, KLK13, SERPINB13, ALOX12, SLC39A2, KRT4, HOPX, FAM25A, EMP1, CNFN, KLK12, APOBEC3A, CAPN14, IVL, KLK8, SPRRIB, IGFBP6, IL36G, KLK7, EGR3, KRT78, CRNN, MAL, LINC00707, KRT24, KRT6A, TMPRSS11B, KRT14, PRB3, KRT13, LOC731424, and BCL2L2-PABPN1.

2. The method according to claim 1, wherein generating or having generated a first transcriptome for the subject comprises a first quantification of expression of at least one RNA derived from the gene.

3. The method according to claim 1, wherein exposing the subject to at least one cat allergen comprises exposing the subject to at least one cat for at least one hour.

4. The method according to claim 3, wherein exposing the subject to at least one cat occurs in a naturalistic exposure chamber (NEC).

5. The method according to claim 1, wherein exposing the subject to at least one cat allergen comprises administering or having administered to the subject cat dander or the at least one cat allergen to the skin of the subject.

6. The method according to claim 1, wherein the at least one cat allergen comprises Fel d 1, Fel d 2, Fel d 3, Fel d 4, Fel d 5, Fel d 6, Fel d 7, or Fel d 8, or any combination thereof.

7. The method according to claim 1, wherein generating or having generated a second transcriptome for the subject comprises a second quantification of expression of at least one RNA derived from the gene.

8. The method according to claim 1, wherein the screening the second transcriptome against the first transcriptome to generate the cat allergen exposure transcriptome comprises determining or having determined the differential gene expression in the second transcriptome with respect to the first transcriptome.

9. The method according to claim 1, wherein the screening of the second transcriptome against the first transcriptome comprises:

i) transforming the first transcriptome into z-scores;

ii) ranking the z-scores; and ii) generating a gene expression signature (GES) for all ranked z-scores using at least one gene which is differentially expressed and is in the first transcriptome, thereby representing at least one change in the second transcriptome with respect to the first transcriptome.

10. The method according to claim 1, wherein the at least one antibody to the cat allergen comprises at least one antibody to Fel d 1.

* * * * *